United States Patent [19]

Tsuji et al.

[11] Patent Number: 5,270,794
[45] Date of Patent: Dec. 14, 1993

[54] FINE STRUCTURE EVALUATION APPARATUS AND METHOD

[75] Inventors: Toshihiko Tsuji, Atsugi; Kenji Saito, Yokohama, both of Japan

[73] Assignee: Canon Kabushiki Kaisha, Tokyo, Japan

[21] Appl. No.: 905,409

[22] Filed: Jun. 29, 1992

[30] Foreign Application Priority Data

Jul. 9, 1991 [JP] Japan .................................. 3-195864
Sep. 20, 1991 [JP] Japan .................................. 3-270281
May 15, 1992 [JP] Japan .................................. 3-148569

[51] Int. Cl.$^5$ .......................................... G01B 11/02
[52] U.S. Cl. ................................... 356/371; 356/386; 356/237; 356/446
[58] Field of Search ............... 356/371, 446, 237, 384, 356/386

[56] References Cited

U.S. PATENT DOCUMENTS

| | | | |
|---|---|---|---|
| 3,782,834 | 1/1974 | Fujimori et al. | 356/167 |
| 4,479,717 | 10/1984 | Cornillault | 356/375 |
| 4,579,453 | 4/1986 | Makita | 356/375 |
| 4,632,557 | 12/1986 | Thompson | 356/401 |
| 4,728,196 | 3/1988 | Gerstorfer | 356/446 |
| 4,827,141 | 5/1989 | Zwirn | 250/560 |
| 4,859,062 | 8/1989 | Thurn et al. | 356/371 |

FOREIGN PATENT DOCUMENTS 2508160 12/1982 France .
62-118206 5/1987 Japan .
2144537 3/1985 United Kingdom .

OTHER PUBLICATIONS

Patent Abstracts of Japan, Kokai No. 58-033107, vol. 7, No. 113, May 1983.
Patent Abstracts of Japan, Kokai No. 63-225110, vol. 13, No. 27, Jan. 1989.
"Method For Microscopic Edge Detection," IBM Technical Disclosure Bulletin, vol. 32, No. 3B, Aug. 1989, pp. 209 and 210.

*Primary Examiner*—Richard A. Rosenberger
*Attorney, Agent, or Firm*—Fitzpatrick, Cella, Harper & Scinto

[57] ABSTRACT

In an apparatus and a method for evaluating the pattern structure of a fine structure, the presence of foreign particles, or the like, an object having a fine structure is scanned with a light beam, or the spot size of the light beam projected onto the object is changed, and extreme values in light scattered by the object are detected. The fine structure is evaluated according to changes in the positions, the number, the intensities or the like of the extreme values, that is, according to distribution characteristics of the extreme values caused by the scanning or the changes in the spot size of the light beam.

21 Claims, 40 Drawing Sheets

EDGE HEIGHT : 1/8 * λ

EDGE HEIGHT : 2/8 * λ

EDGE HEIGHT : 3/8 * λ

EDGE HEIGHT : 4/8 * λ

EDGE HEIGHT: 5/8 * λ

EDGE HEIGHT: 6/8 * λ

EDGE HEIGHT: 7/8 * λ

EDGE HEIGHT: 8/8 * λ

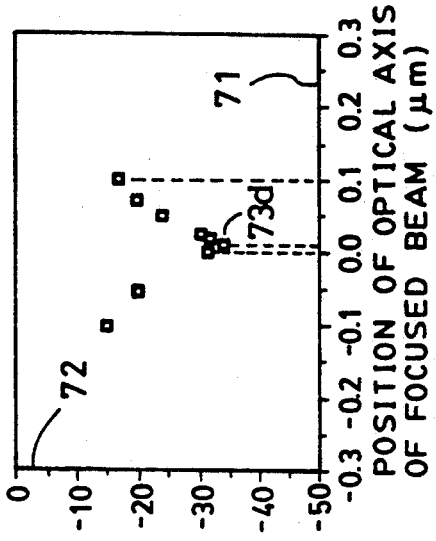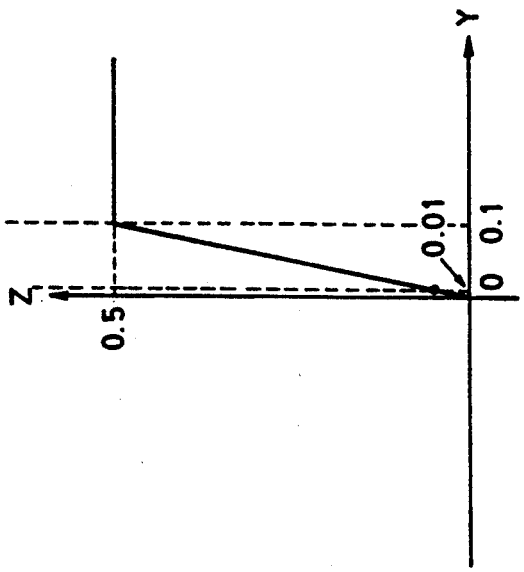
FIG. 10(A)
FIG. 10(B)
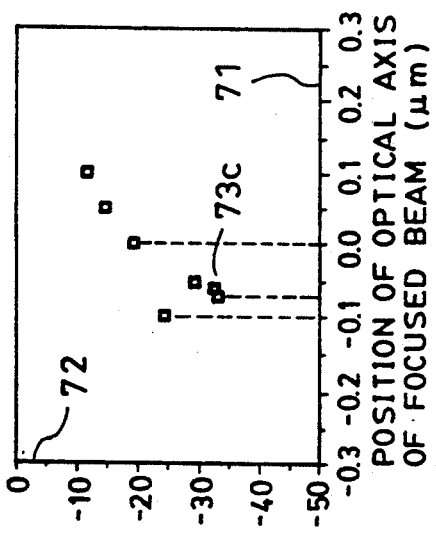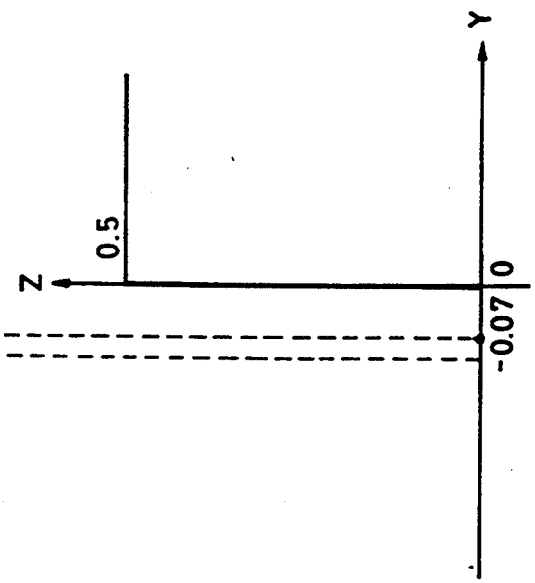

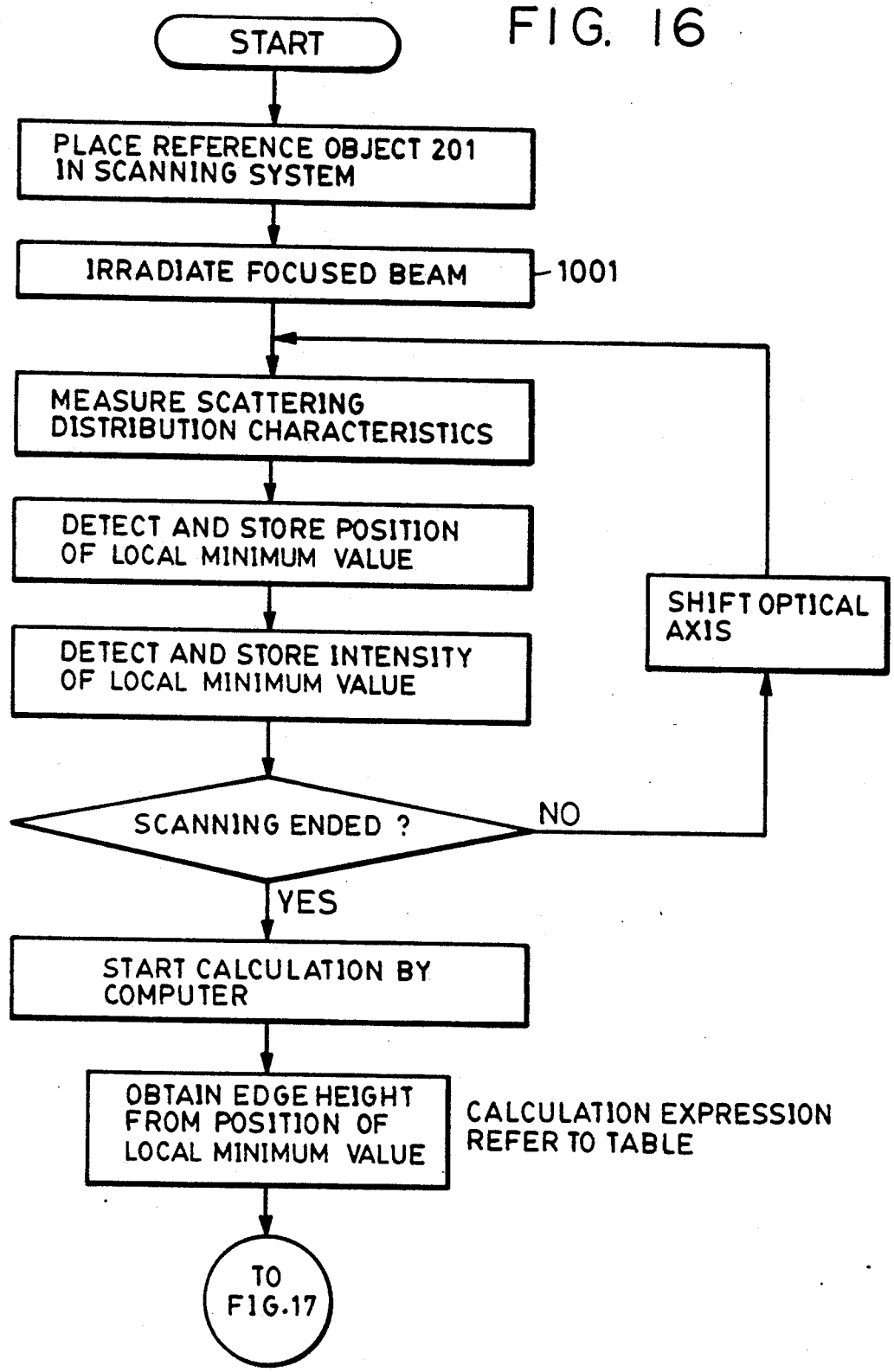

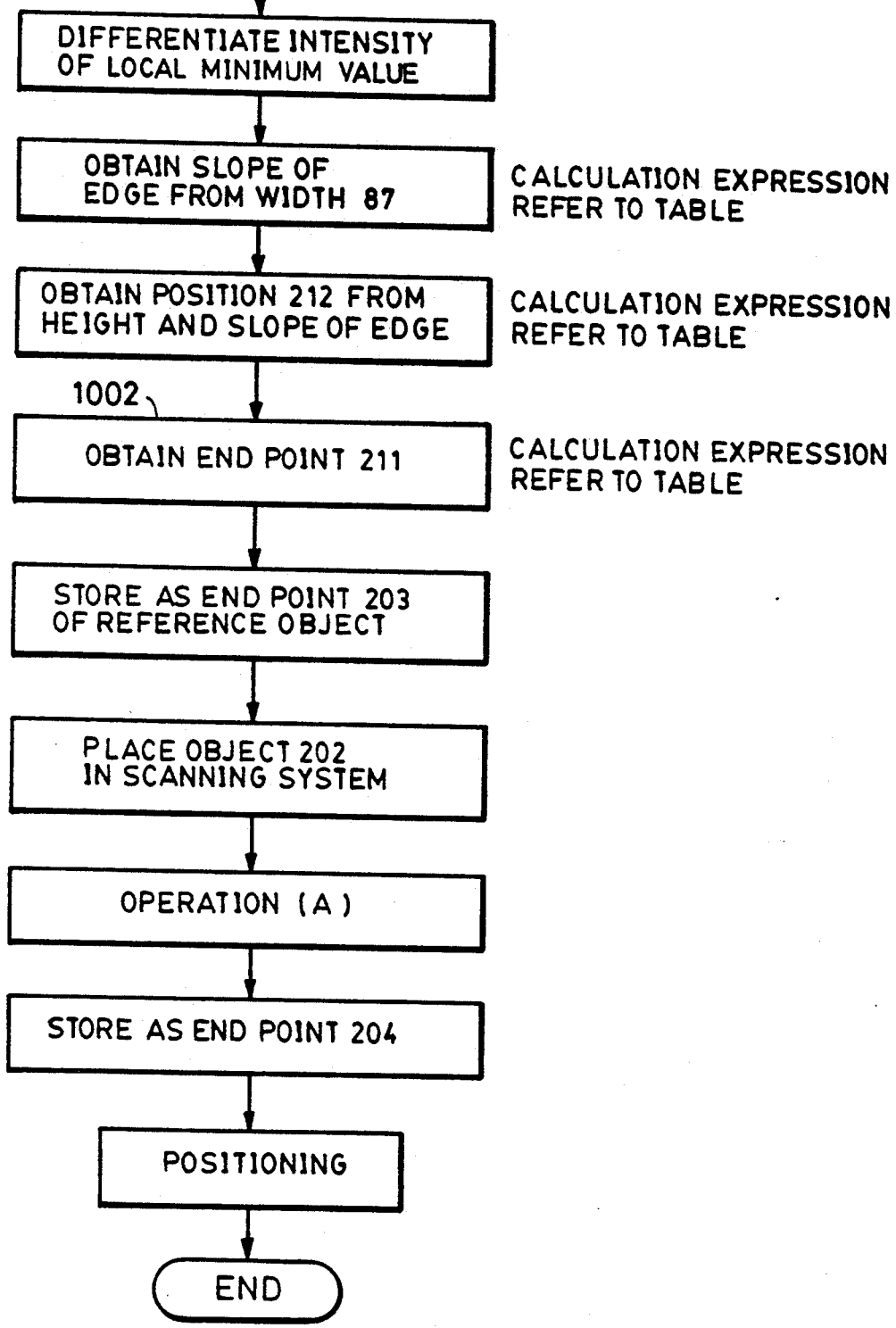

FINE STRUCTURE EVALUATION APPARATUS AND METHOD

BACKGROUND OF THE INVENTION

1. Field of the Invention

This invention relates to a fine structure evaluation apparatus and a fine structure evaluation method. The present invention is suitable for, for example, edge evaluation apparatuses, positioning apparatuses, pattern line width measuring apparatuses, foreign particle inspection apparatuses and the like, which perform optical evaluation of a fine structure, detection of foreign particles, and the like by irradiating light from a light source means onto a minute region on an object to be measured, photoelectrically detecting light scattered by a fine structure of the object or a foreign particle on the object by a detecting system, and analyzing and evaluating signals from the detecting system.

2. Description of the Related Art

Various kinds of fine structure evaluation apparatuses for detecting and evaluating an outer shape, such as an edge, a line width or the like, of a fine pattern, have been proposed. For example, there have been known edge detection apparatuses for detecting an edge portion of a pattern on the surface of a wafer as a fine structure, and positioning a reticle with the wafer.

FIG. 1 is a schematic diagram of a principal part of an optical system of a known edge detection apparatus. In this apparatus, the beam size of laser light from a laser light source 2a is expanded by a beam expander 3a, and is adjusted by a slit 4a, from which the light beam emanates. The light beam is focused by a focusing lens 6a to illuminate an edge region 10a of a pattern 10 on a wafer surface 8a. In FIG. 1, curves A and B on the x and y coordinate axes schematically represent the intensity distributions of the light beam.

A greater amount of scattered light is generated from the edge portion 10a of the pattern 10 than from other portions. Accordingly, the presence or the intensity of the scattered light is detected by photoelectric detectors 14, and the position of the edge portion 10a of the pattern 10 is detected utilizing signals from the photoelectric detectors 14. That is, positional information with respect to the pattern 10 is detected.

The edge detection apparatus shown in FIG. 1 scans the object 10 while focusing the laser light into a minute spot, and photoelectrically detects the presence or the intensity distribution of the light scattered by the edge portion 10a by the photoelectric detectors 14 disposed at an angle with respect to the optical axis of the focused light beam, whereby the position of the edge portion 10a is detected. At that time, light beam deforming means 4a comprising the slit for deforming the shape of the projected spot of the laser light into the shape of an ellipse is provided, whereby the width of the spot in the direction of the minor axis of the ellipse is reduced to increase resolution in detection.

FIG. 2 is a schematic diagram of a principal part of a pattern line size measuring apparatus proposed in Japanese Patent Application Public Disclosure (Kokai) No. 62-118206 (1987).

In FIG. 2, a laser light beam 160 from a laser light source 156 passing through a half-mirror 157 is focused by an objective lens 155 to illuminate a pattern 153 on the surface of an object 152 to be inspected mounted on a vibrating stage 151. Light scattered by the pattern 153 and a reflected light beam 161 are focused by the objective lens 155, and the pattern 153 is imaged onto the surface of a photosensor 158. At that time, the vibrating stage 151 is vibrated in the same direction as the measuring direction of the pattern 153 by a vibrator 154. A signal 162 obtained from the photosensor 158 is processed by a signal processor 159 to obtain the size of the pattern 153.

As apparatuses for detecting foreign particles on an object to be inspected, foreign particle inspection apparatuses have been proposed in which laser light is obliquely projected onto an object, and light scattered by a foreign particle is detected by photosensors disposed at certain positions.

In the edge detection apparatus shown in FIG. 1, since light scattered by the fine structure is detected by the photoelectric detectors 14 fixedly disposed at a predetermined angle with respect to the focused light, the following problems are present:

(1-1) Since the presence of scattered light, or a change in the intensity distribution of only a part of scattered light is detected, only an approximate position of the border of the edge portion can be detected.

(1-2) Since analysis processing of fine structure information included in scattering distribution characteristics of scattered light in a manner to be described later is not performed, the shape of the fine structure cannot be evaluated.

(1-3) It is difficult to optically evaluate the fine structure of the object with a high resolution.

In the conventional pattern line size measuring apparatus shown in FIG. 2, the photosensor 158 is disposed at a position optically conjugate to the pattern 153 on the object 152, and a signal representing light reflected and scattered by the pattern 153 is detected by the photosensor 158, whereby the size of the pattern 153 is measured. Accordingly, in the conventional pattern line size measuring apparatus, the spot size of the light beam obtained by the illuminating optical system is on the order of about one wavelength of the illuminating light beam. Hence, if the line width of the pattern is smaller than the spot size, it is impossible to measure the line width and the height of the pattern line from a reference surface.

Furthermore, in the conventional foreign particle inspection apparatus, it is difficult to discriminate between light scattered by a fine structure of an object and light scattered by a foreign particle, and therefore to optically inspect a fine foreign particle with a high resolution.

SUMMARY OF THE INVENTION

It is an object of the present invention to provide a fine structure evaluation apparatus and a fine structure evaluation method which can perform optical evaluation of an outer shape of a fine structure, and the like, with a high resolution exceeding the resolution of a conventional optical microscope, and which can easily detect a fine foreign particle.

To achieve the above-noted objects, the present invention provides an apparatus for evaluating a fine structure of an object to be inspected. The apparatus includes illumination means for irradiating the object with a light beam, irradiating state changing means for changing an irradiating state of the light beam irradiating the object by the illumination means, detection means for detecting those portions having extreme intensity values of light scattered by the illuminated object, and for producing a detection output and calculation means for receiving the detection output from the detection means, and for evaluating the fine structure of the object according to changes in distribution characteristics of those portions having the extreme intensity values, while changing the irradiating state of the light beam by the irradiating state changing means.

The present invention also provides a method of evaluating a fine structure of an object to be inspected. The method includes the steps of irradiating a light beam onto the object, changing an irradiating state of the light beam, detecting those portions of light scattered by the irradiated object having extreme intensity values and evaluating the fine structure of the object according to changes in distribution characteristics of those detected portions having the extreme values, while changing the irradiating state of the light beam.

The present invention also provides an apparatus for evaluating a fine structure of an object to be inspected. The apparatus includes a light source for emitting a light beam, an illuminating optical system for receiving the light beam emitted from the light source and for irradiating a predetermined position of the object, the illuminating optical system being capable of changing an irradiating state of the light beam onto the object, a photoelectric transducer for detecting those portions of light scattered by the irradiated object having extreme intensity values and a signal processing system for evaluating the fine structure of the object according to changes in distribution characteristics of those portions having the extreme values, while changing the irradiating state of the light beam by the illuminating optical system.

The foregoing and other objects, advantages and features of the present invention will become more apparent from the following description of the preferred embodiments taken in connection with the accompanying drawings.

BRIEF DESCRIPTION OF THE DRAWINGS

FIGS. 10(A) and 10(B) are diagrams illustrating changes in the intensities of the local minimum values in accordance with the scanning positions of edges;

FIGS. 16 and 17 are flowcharts of the positioning operation shown in FIGS. 15(A) through 15(C);

DESCRIPTION OF THE PREFERRED EMBODIMENTS

Figure 1:
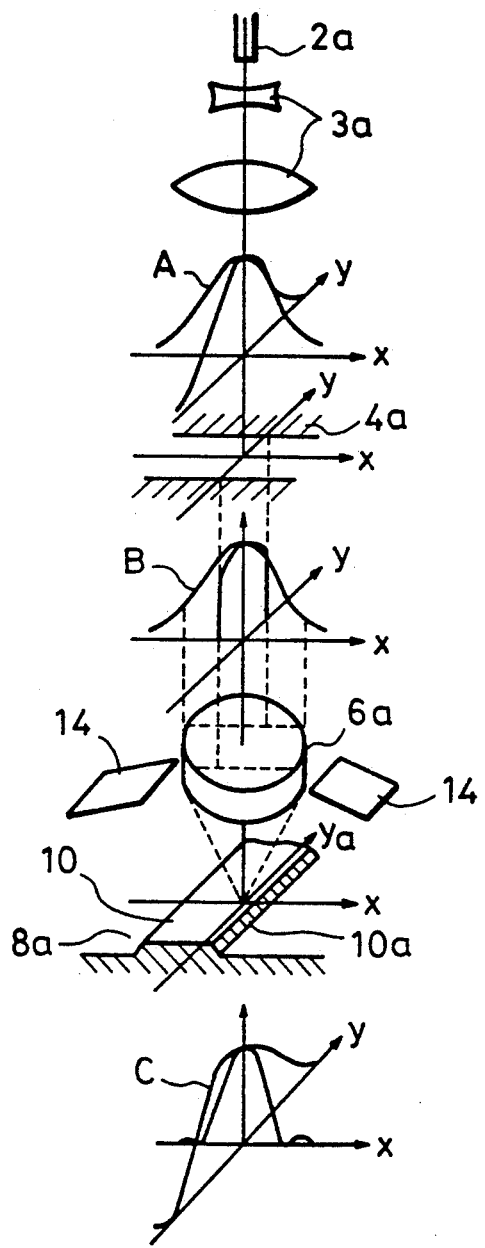
FIG. 1 is a schematic diagram of a principal part of a conventional fine structure evaluation apparatus.
Figure 2:
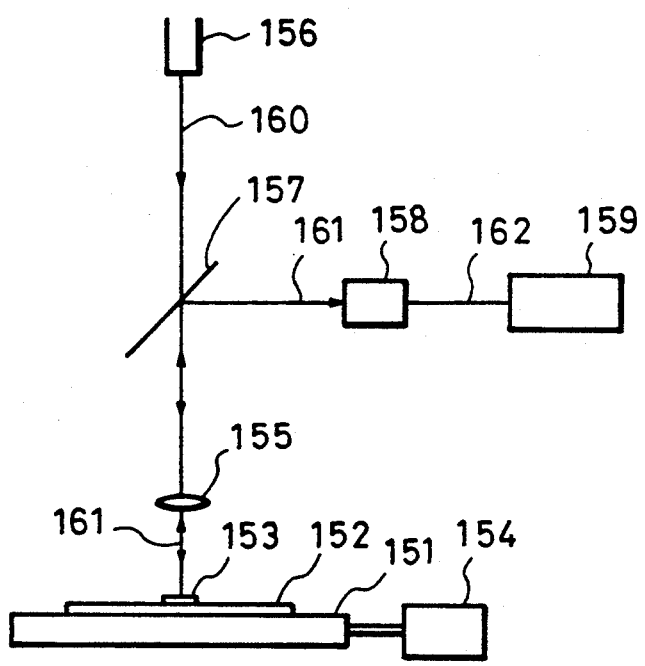
FIG. 2 is a schematic diagram of a principal part of another conventional fine structure evaluation apparatus.

A fine structure evaluation apparatus which will be described below is characterized in that a light beam from a light source means is projected upon an object having a fine structure via an illuminating optical system, scattering distribution characteristics of light scattered by the fine structure of the object are detected by a detection system, and scattering signals representing the positions, the number, changes, the intensities, and the like of the extreme values in the scattering distribution characteristics obtained by the detection system are processed by a signal processing system to evaluate the fine structure.

Another fine structure evaluation apparatus which will be described below is characterized in that a light beam from a light source means is guided and optically scanned onto an object having a fine structure, scattering distribution characteristics of light scattered by the fine structure of the object are detected by a detection system, and scattering signals representing the positions, the number, changes, the intensities, and the like of the extreme values in the scattering distribution characteristics obtained by the detection system are processed by a signal processing system to evaluate the fine structure.

The signal processing system is characterized in that, for example, the outer shape of the fine structure of the object is evaluated, positional information of the fine structure of the object is detected, and the object is driven to a predetermined position by means of a driving means using a signal from the signal processing system.

A fine structure evaluation method which will be described below is characterized in that it includes means for irradiating a light beam onto an object having a fine structure, detecting distribution characteristics of light scattered by the object, and evaluating the fine structure using at least one of the positions, the number, changes and the intensities of the extreme values in the distribution characteristics of the scattered light. The method is also characterized in that, for example, it scans an object having a fine structure with a light beam, detects distribution characteristics of light scattered by the object, and evaluates the fine structure according to changes in at least one of the positions, the number, changes and the intensities in extreme values in the distribution characteristics of the scattered light as a result of the scanning.

A foreign particle inspection apparatus, which will be described below, comprising a light source, an optical system for irradiating a light beam from the light source onto an object, a scanning system for relatively scanning the irradiated region and the object, and a detection system for detecting scattering distribution characteristics of light scattered by the object to perform foreign particle inspection by analyzing the detected distribution signals, is characterized in that the detection system detects the presence of foreign particles on the object by analyzing the number or the positions of the extreme values in the detected scattering distribution characteristics.

Preferred embodiments of the present invention will now be explained in detail with reference to the drawings.

Figure 3A:
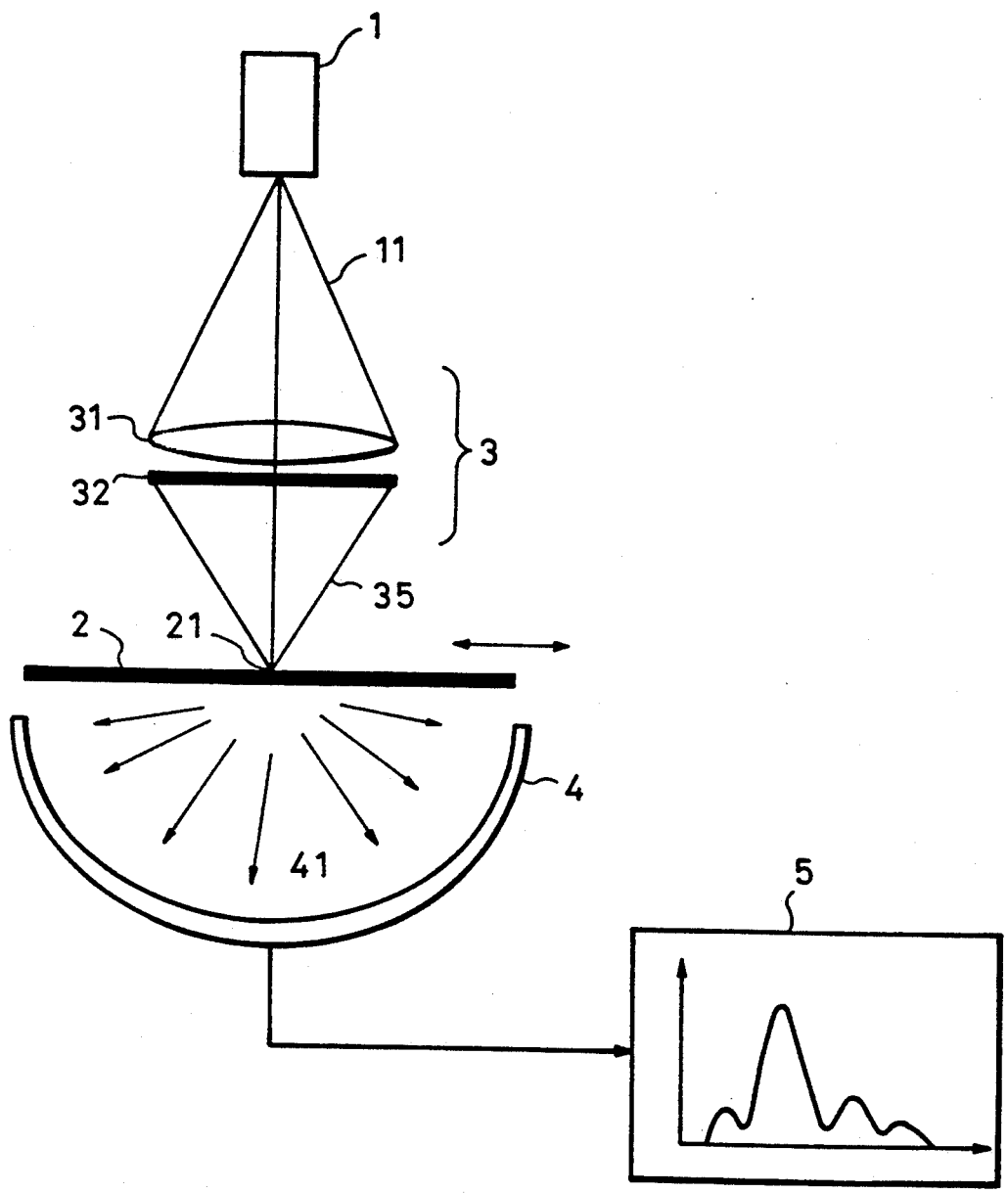
FIG. 3A is a schematic diagram of a principal part of a first embodiment of the present invention.

FIG. 3A is a schematic diagram of a principal part of a first embodiment of the present invention. In FIG. 1, there are shown a light source means 1, and an object 2 to be inspected having a fine structure. An illuminating optical system 3 illuminates a minute region 21 on the surface of the object 2 by focusing light 11 from the light source means 1 thereon, and comprises a lens system 31, and a filter system 32 for passing only a light beam having predetermined spectral characteristics. A detection system 4 includes a photoelectric transducer comprising an array of photosensors, whose photosensing surfaces are directed toward the object side, for detecting scattering distribution characteristics of light 41 scattered by the fine structure of the object 2. A signal processing system 5 analyzes the fine structure from signals representing the scattering distribution characteristics detected by the detection system 4. As indicated by the two-head arrow, the object 2 is moved relative to the apparatus by a driving means (not shown).

In the present embodiment, for example, a semiconductor laser, a light source for emitting a coherent light beam, such as a He-Ne laser, an Ar laser or the like, a light source for emitting an incoherent light beam such as a light-emitting diode, a halogen lamp or the like may be used as the light source means 1. A light source which is suitable for a fine structure to be evaluated is selected on every occasion.

In the present embodiment, the light 11 emitted from the light source means 1 is made to be a focused light beam 35 by the illuminating optical system 3, and the light beam 35 is focused onto the minute region 21 on the object 2 (such as a mask or the like, the same principle holds even for a nontransparent object, such as a wafer or the like). The light beam 35 focused onto the object 2 is scattered with scattering distribution characteristics which depend upon the fine structure (such as a pattern or the like) within the minute region 21. The scattered light 41 is received by the detection system 4, and the scattering distribution characteristics of the scattered light 41 are detected while being subjected to photoelectric conversion. The detection system 4 detects transmitted scattered light and reflected scattered light. From the detected scattering distribution characteristics, information with respect to the fine structure is extracted and analyzed by the signal processing system 5 with an excellent S/N ratio, and optical evaluation of the fine structure is performed with a high resolution.

A typical example of extracting information on the fine structure of the object 2 from the scattering distribution characteristics at that time will now be shown.

Figure 3B:
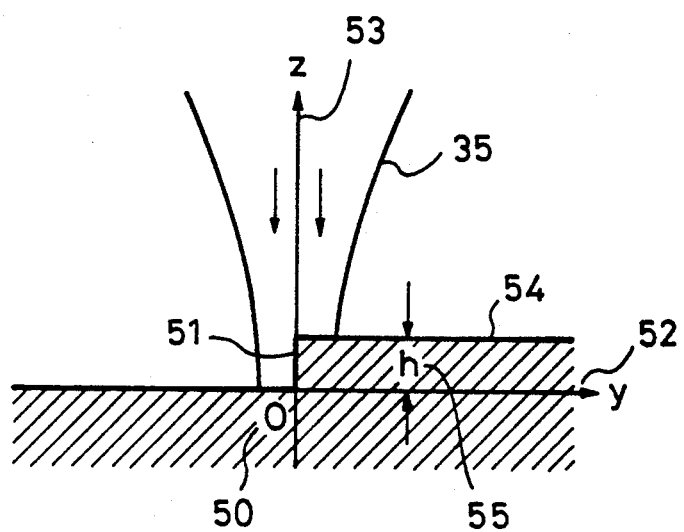
FIG. 3B is a diagram illustrating an edge portion of the object shown in FIG. 3A.
Figure 4A:
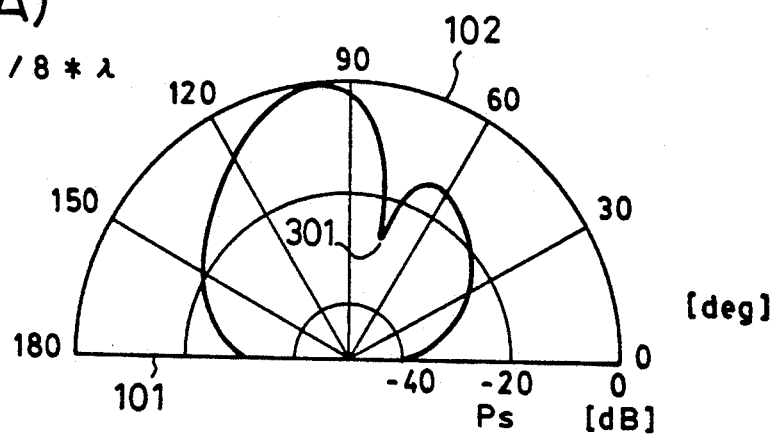
FIGS. 4A(A) through 4A(D) are diagrams illustrating scattering distribution characteristics caused by edges.
Figure 4A:
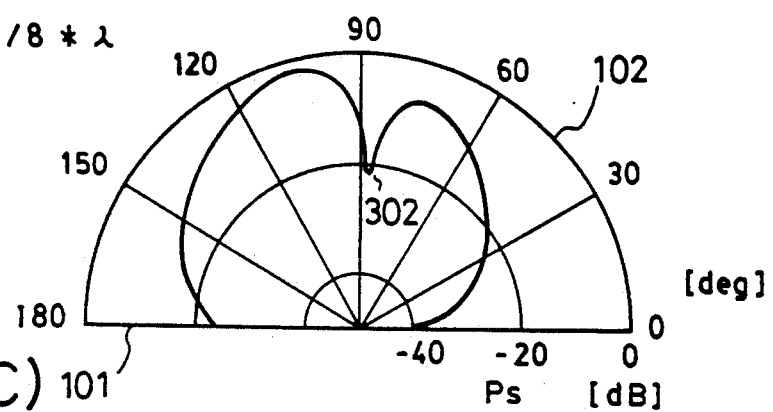
Figure 4A:
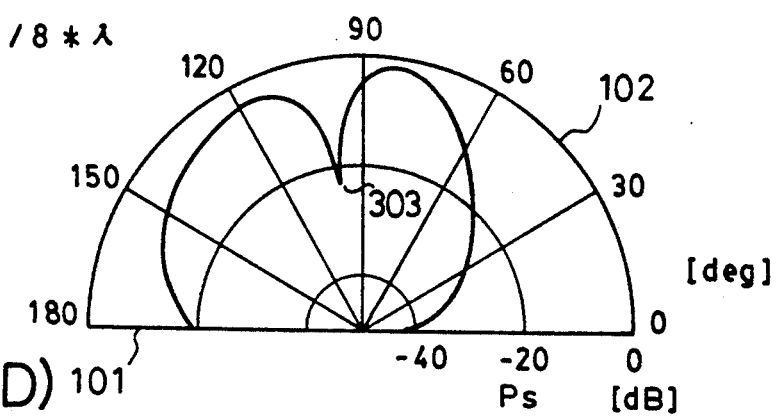
Figure 4A:
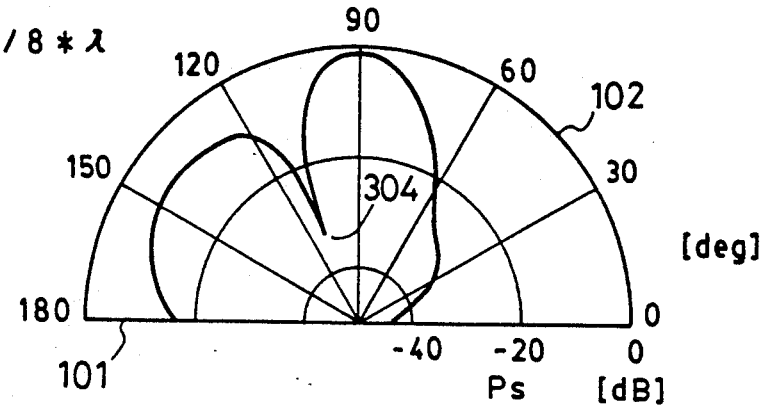
Figure 4B:
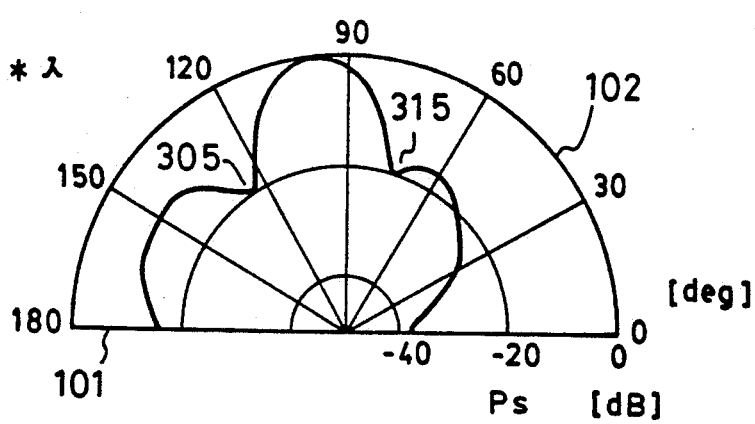
FIGS. 4B(A) through 4B(D) are diagrams illustrating scattering distribution characteristics caused by edges.
Figure 4B:
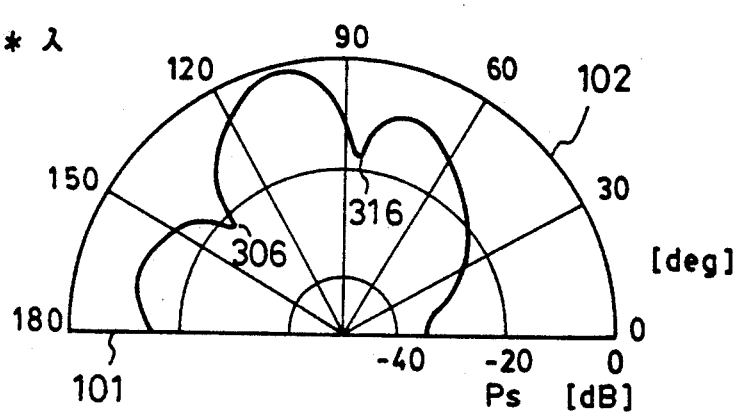
Figure 4B:
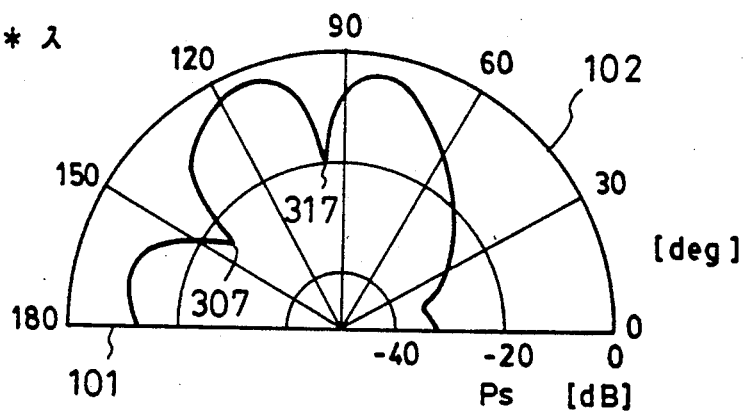
Figure 4B:
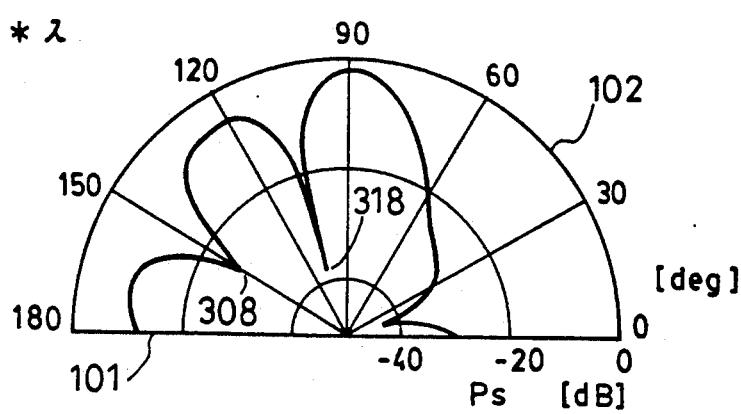

FIG. 3B is a schematic diagram including the coordinate system shown when a focused light beam is projected onto an object having a fine edge (a step having a fine difference in height, a border between a transparent portion and an opaque portion, a border between adjacent different substances, or the like in the object 2 will be hereinafter termed an "edge"). A boundary surface (an edge) 51 of the object 2 is uniform in the direction perpendicular to the plane of FIG. 3B (the x direction), and comprises a perfect conductor. The origin, the y axis and the z axis of the coordinate system of the edge 51 are set as indicated by reference numerals 50, 52 and 53, respectively. If the focused light beam 35 is projected onto the edge 51 so that the optical axis of the focused light beam 35 coincides with the z axis 53, the focused light beam 35 is scattered with certain scattering distribution characteristics. The scattering distribution characteristics are measured in a far field region separated from the origin 50 by about 1,000 multiples of the wavelength of the light. FIGS. 4A(A) through 4A(D) and 4B(A) through 4B(D) show the scattering distribution characteristics when a Gaussian beam having a wavelength $\lambda$ of 0.6328 $\mu$m and a beam-spot diameter of 1.2 $\mu$m, with the focal plane arranged on the y axis 52 is used as the focused light beam 35, and the height 55 of the edge 51 is sequentially changed by $\lambda/8$.

Before explaining the scattering distribution characteristics shown in FIGS. 4A(A) through 4B(D), an explanation will be provided of the basic method of evaluating scattering distribution characteristics according to the present invention.

Figure 4C:
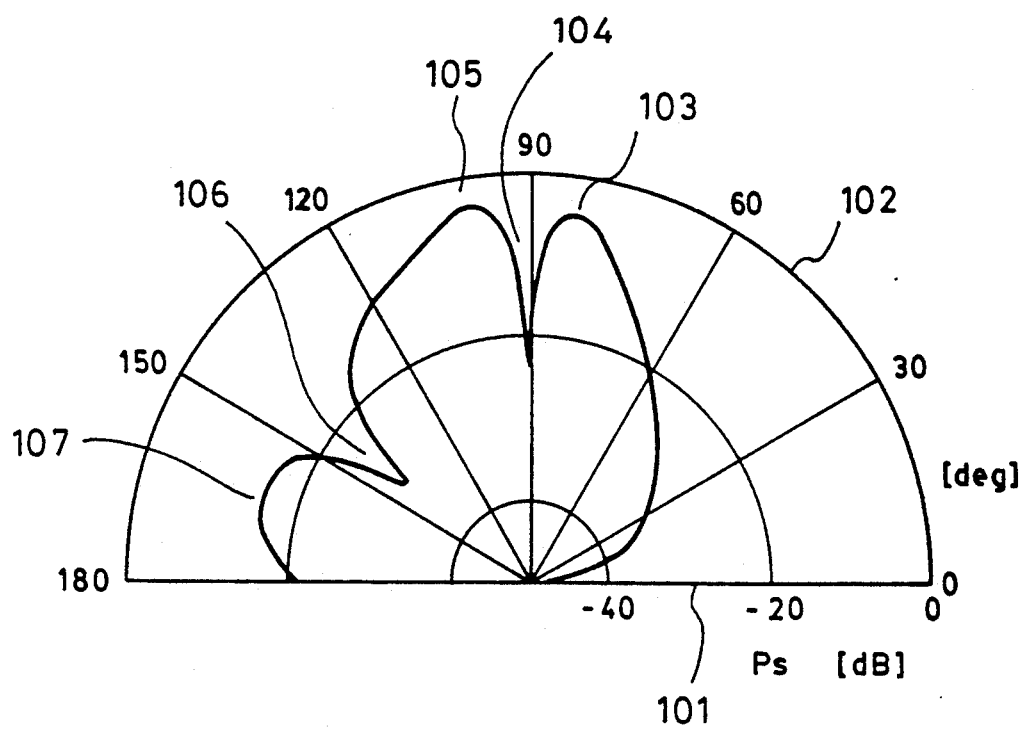
FIG. 4C is a diagram illustrating scattering distribution characteristics.

Scattering distribution characteristics produced when a light beam is projected onto a minute region having a fine edge structure on an object are assumed to be as shown in FIG. 4C. In FIG. 4C, the radial-direction axis 101 represents the intensity of scattered light, and the circumferential-direction axis 102 represents the scattering angle. In general, extreme values of the intensity of scattered light are present in scattering distribution characteristics. In the case of FIG. 4C, such extreme values are represented by reference numerals 103, 104, 105, 106 and 107. The scattering distribution characteristics include information on the structure of the minute region illuminated by the light, and the number, the positions and the intensities of the extreme values in the scattering distribution characteristics reflect the fine structure of the edge 51, such as the height, the slope, and the like of the edge 51. Hence, if the conditions of the illuminating light are the same, the scattering distribution characteristics are uniquely determined by the fine structure. The following methods of evaluating a fine structure from scattering distribution characteristics are present:

(2-1) A method of evaluating a fine structure by scanning an object to be evaluated with illuminating light while performing analysis from the conditions of the illuminating light projected onto a minute region on the object, and the number, the positions and the intensities of extreme values in detected scattering distribution characteristics by referring to a previously-calculated correspondence table or using a previously-obtained relational expression.

(2-2) A method of evaluating a fine structure by detecting scattering distribution characteristics while scanning an object to be evaluated with illuminating light projected onto a minute region on the object, and analyzing the number, the positions and the intensities of extreme values in the detected scattering distribution characteristics.

Next, the scattering distribution characteristics shown in FIGS. 4A(A) through 4B(D) obtained in the present embodiment will be explained.

The radial-direction axis 101 shown in FIGS. 4A(A) through 4B(D) represents the intensity of scattered light. The unit of the intensity is a decibel, and 0 dB corresponds to the maximum value of the intensity of scattered light when the boundary surface 51 comprises a perfect conductor. The semicircumferential-direction axis 102 shown in FIGS. 4A(A) through 4B(D) represents the scattering angle, in which the counterclockwise direction from the y axis 52 shown in FIG. 3B is assumed to be the positive direction. The center of the semicircle corresponds to the origin 50 shown in FIG. 3B.

Figure 5:
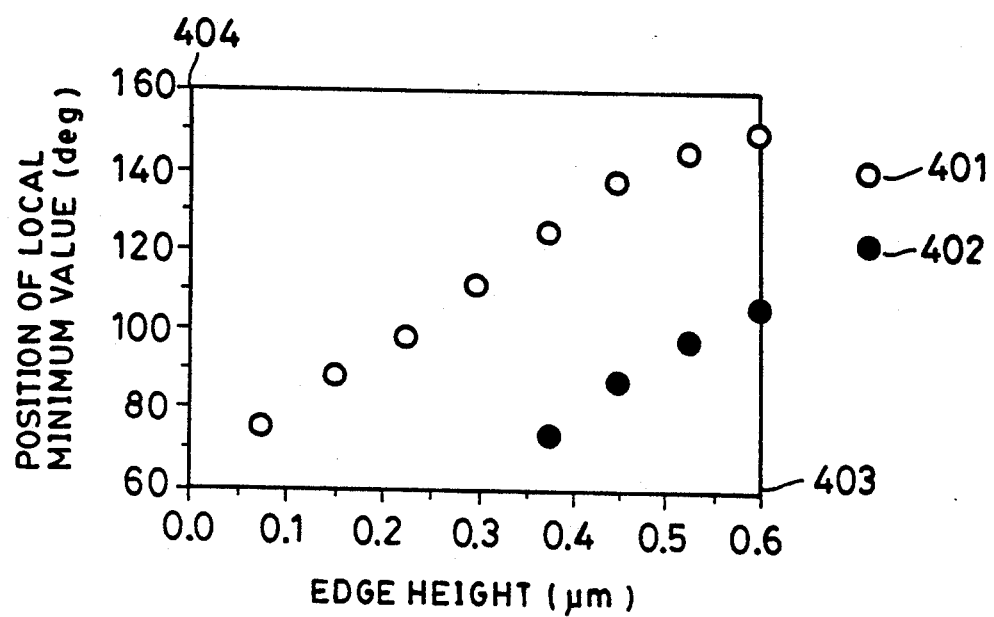
FIG. 5 is a graph illustrating the relationship between the edge height and the position of the local minimum value in scattering distribution characteristics.

In checking the scattering distribution characteristics shown in FIGS. 4A(A) through 4B(D) in the sequence of the edge height, it can be understood that the positions and the number of the local maximum values and the local minimum values in the scattering distribution characteristics greatly change in accordance with minute changes in the edge height (h) 55. As an example, FIG. 5 shows the relationship between the position of the local minimum value and the edge height obtained from FIGS. 4A(A) through 4B(D). In FIG. 5, the abscissa 403 represents the edge height, and the ordinate 404 represents the position of the local minimum value (the scattering angle). White circles 401 represent the angles of the local minimum values 301, 302, 303, 304, 305, 306, 307 and 308 in FIGS. 4A(A) through 4B(D), and black circles represent the angles of the local minimum values 315, 316, 317 and 318 shown in FIGS. 4A(A) through 4B(D).

Although scattering distribution characteristics as shown in FIGS. 4A(A) through 4B(D) differ in accordance with the shape of the edge and incident conditions (the wavelength, the position of the optical axis, the incident angle, the position of the focal plane, the beam-spot size, and the like) of the illuminating light, it can be understood that the positions, the number, the intensities, changes, and the like of the extreme values include information on the fine structure.

Accordingly, in the present embodiment, the height of the fine edge on the object is obtained by analyzing the positions and the number of the local minimum values in the scattering distribution characteristics by the signal processing system while previously providing a correspondence table using the relationship shown in FIG. 5, or providing a relational expression between the edge height and the position of the local minimum value. Such processing is performed for a predetermined region while moving the object, and fine structures in the entire region can be measured from changes in the scattering distribution characteristics during the processing.

Figure 6:
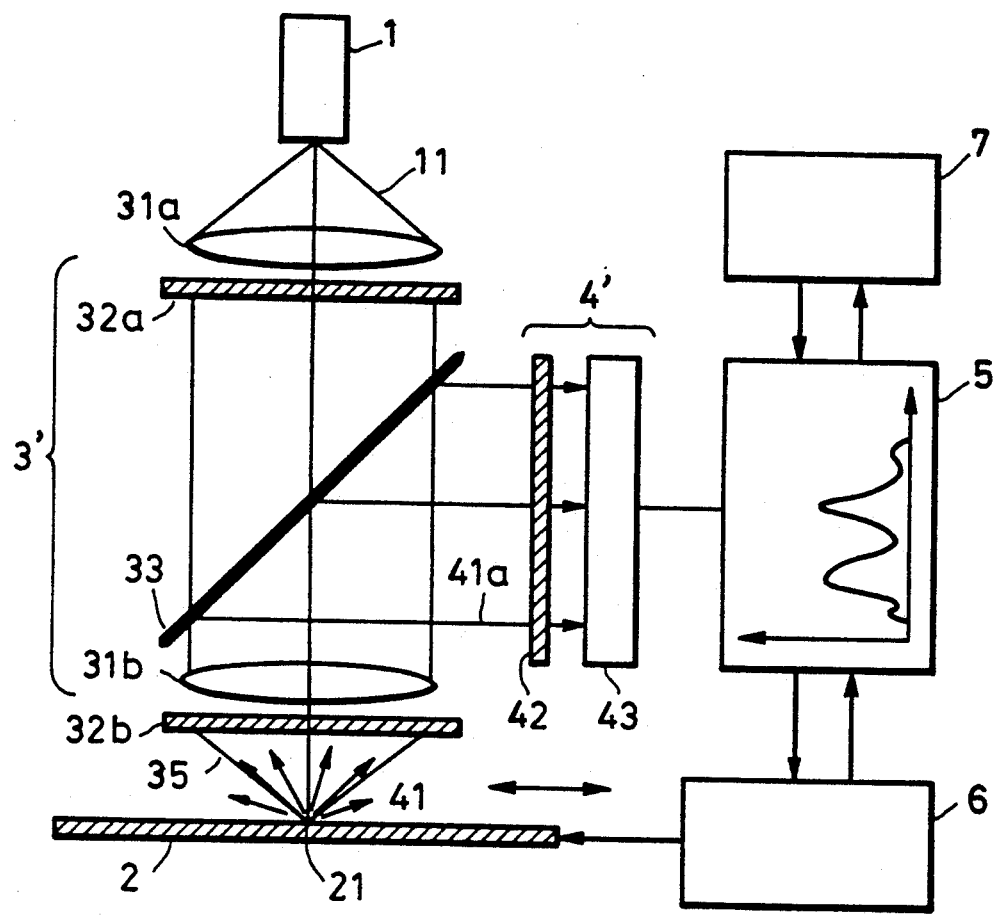
FIG. 6 is a schematic diagram of a principal part of a second embodiment of the present invention.

FIG. 6 is a schematic diagram of a principal part of a second embodiment of the present invention. In the present embodiment, the invention is applied to an edge evaluation apparatus for detecting an edge portion of a fine structure.

In FIG. 6, there are shown a light source means 1, and an object 2 having a fine structure. An illuminating optical system 3' focuses light from the light source means 1 to illuminate a minute region 21 on the object 2. The illuminating optical system 3' includes a lens system 31$a$ and a filter system 32$a$ at the side of the light source means 1, a lens system 31$b$ and a filter system 32$b$ at the side of the object 2, and a beam splitter 33 for introducing scattered light from the object 2 to a detection system 4' between the filter system 32a and the lens system 31b. The detection system 4' includes a filter system 42 for detecting scattering distribution characteristics of light 41 scattered by the fine structure of the object 2, and a photoelectric detector 43, such as a one-dimensional CCD (charged-coupled device), a two-dimensional CCD or the like. A signal processing system 5 analyzes the fine structure of the object 2 from signals representing the scattering distribution characteristics detected by the detection system 4'. A scanning system 6 relatively scans the object 2 with the focused light beam 35. A computer 7 performs calculation processing of data processed by the signal processing system 5 to obtain the outer shape of the fine structure of the object 2.

As in the first embodiment, in the present embodiment, for example, a semiconductor laser, a light source for emitting a coherent light beam, such as a He-Ne laser, an Ar laser or the like, a light source for emitting an incoherent light beam such as a light-emitting diode, a halogen lamp or the like may be used as the light source means 1. A light source which is suitable for a fine structure to be evaluated is selected on every occasion.

In the present embodiment, light 11 emitted from the light source means 1 is first focused onto the minute region 21 on the object 2 having a fine edge structure by means of the illuminating optical system 3'. The light beam focused on the object 2 is scattered with scattering distribution characteristics which depend upon the edge structure within the minute region 21. The scattered light 41 is reflected by the beam splitter 33 after passing through the filter system 32b and the lens system 31b provided at the side of the object 2 to be separated as scattered light 41a, which is introduced into the detection system 4'. When the scattered light 41a is parallel light, the minute region 21 and the detection surface of the detection system 4' are in the relationship of a Fourier transform. The scattering distribution characteristics of the scattered light 41a introduced in the detection system 4' are detected by the photoelectric detector 43 of the detection system 4' while being subjected to photoelectric conversion. The detected scattering distribution characteristics are analyzed by the signal processing system 5. The result of the analysis is processed by the computer 7, and the evaluation of the outer shape, such as the shape of the edge or the like, is performed. At that time, by relatively scanning the object 2 with the focused light beam 35 by means of the scanning system 6, the position of the illuminated minute region 21 on the edge portion of the object 2 changes, whereby the scattering distribution characteristics change. The changes in the scattering distribution characteristics are sequentially analyzed and processed by the signal processing system 5 and the computer 7.

Next, the method of signal processing in the present embodiment will be explained. FIGS. 7 and 8(A) through 8(C) are diagrams illustrating the principle of the method of analyzing scattering distribution characteristics in the present embodiment.

Figure 7:
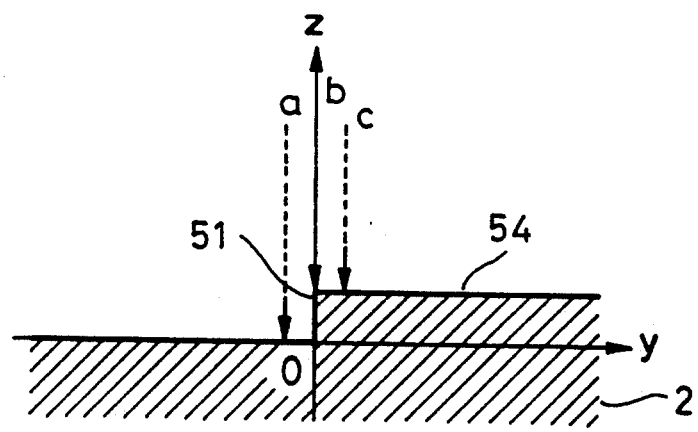
FIG. 7 is a diagram illustrating the relationship between the scanning position and an edge.
Figure 8A:
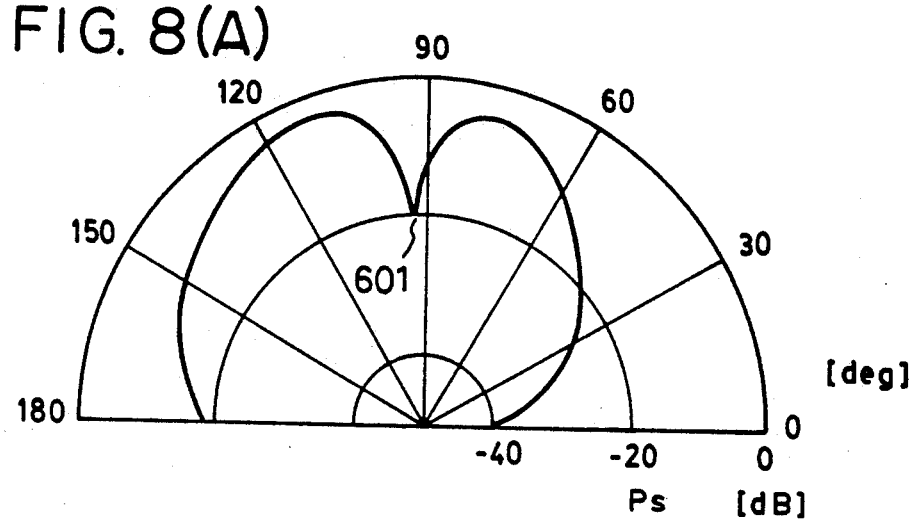
FIGS. 8(A) through 8(C) are diagrams illustrating scattering distribution characteristics caused by the edge shown in FIG. 7.
Figure 8B:
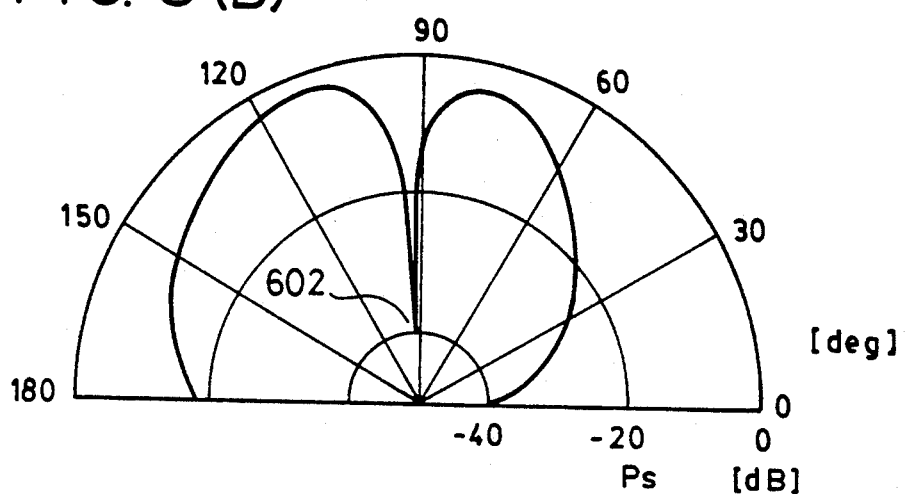
Figure 8C:
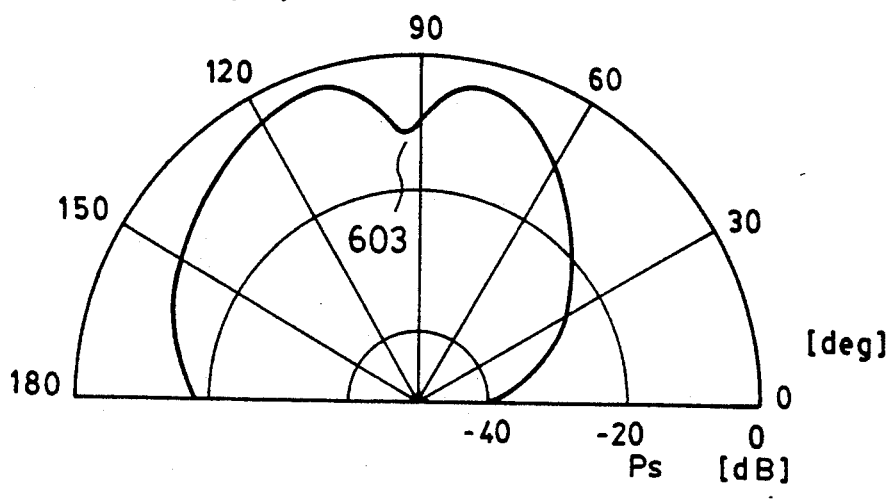
Figure 9B:
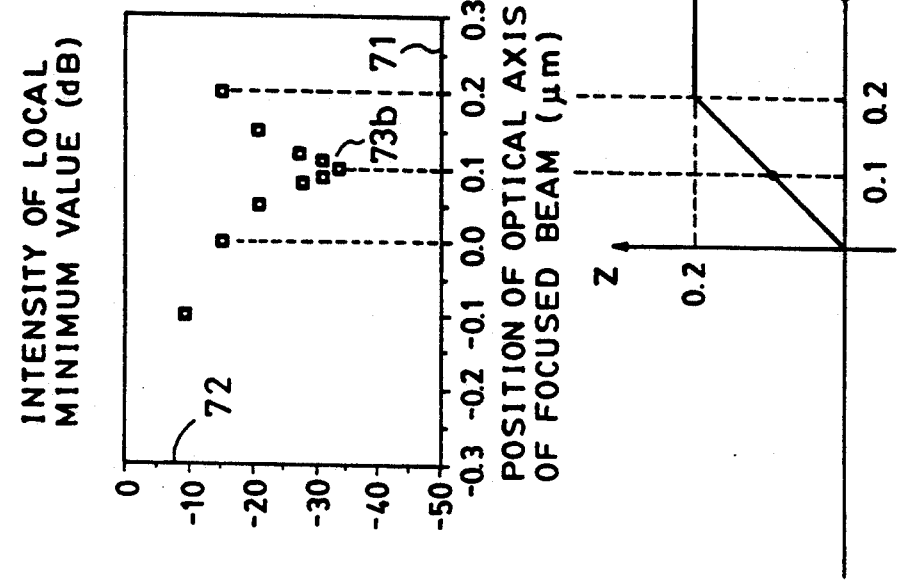
FIGS. 9(A) and 9(B) are diagrams illustrating changes in the intensities of the local minimum values in accordance with the scanning positions of edges.
Figure 9A:
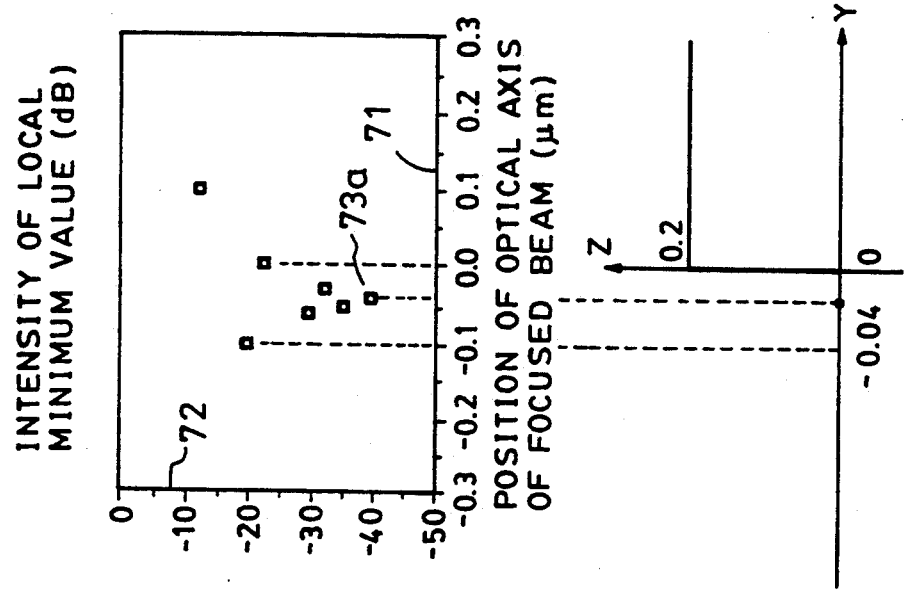

FIG. 7 illustrates the cross section of a fine edge on the object 2 in the same manner as in FIG. 3B. The height of the edge 51 is 0.2 μm. A Gaussian beam having a wavelength of 0.6328 μm and a beam spot diameter of 1.2 μm is used as the focused light beam, and the position of the beam waist is arranged to be on the y axis. The edge is scanned with the above-described focused light beam by means of the scanning system. Scattering distribution characteristics when the optical axis of the scanning system corresponds to positions "a", "b" and "c" shown in FIG. 7 become as shown in FIGS. 8(A) through 8(C), respectively. The following items hold with respect to the local minimum values 601, 602 and 603 in the scattering distribution characteristics in FIGS. 8(A) through 8(C), respectively:

(3-1) The position (the scattering angle) of the minimum value does not change in accordance with scanning of the focused light beam (the position of the optical axis in the y-axis direction), but only depends upon the edge height. Accordingly, if the conditions of the incident light are determined, the edge height can be obtained from the position of the local minimum value in the scattering distribution characteristics.

(3-2) The intensity of the local minimum value changes in accordance with the position of the optical axis of the scanning system relative to the edge, and has a smallest value near the edge. The position where the smallest value is obtained differs in accordance with the tilt angle and the height of the edge.

(3-3) The amount of change of the intensity of the local minimum value as a function of the amount of the movement of the optical axis of the scanning system depends upon the slope of the edge.

According to the above-described characteristics, in the present embodiment, the fine edge is evaluated by scanning the object with the focused light beam and analyzing information with respect to changes in the local minimum value in the scattering distribution characteristics. That is, the position of the edge is detected.

FIGS. 9(A), 9(B), 10(A) and 10(B) illustrate how the intensity of the local minimum value in the scattering distribution characteristics changes when the object is scanned with the focused light beam.

In FIGS. 9(A) through 10(B), the abscissa 71 represents the position of the optical axis of the focused light beam. The ordinate 72 represents the intensity of local the minimum value in the scattering distribution characteristics in units of a decibel. In each of FIGS. 9(A) through 10(B), the lower diagram illustrates the shape of the edge of the corresponding object. In comparing FIG. 9(A) with FIG. 9(B), it can be understood that positions 73a and 73b where the intensities have smallest values differ, and the way of change in the intensity differs because the tilt angle of the edge differs. The same holds for FIGS. 10(A) and 10(B). It also can be understood that if the edge height changes, positions 73a, 73b, 73c and 73d where the intensity of the local minimum value has a smallest value changes even between edges having the same tilt angle. In the present embodiment, by utilizing such a property, the slope of the edge is obtained from changes in the intensity of the local minimum value, and the position of the edge is also detected from the position of the local minimum value.

Figure 11A:
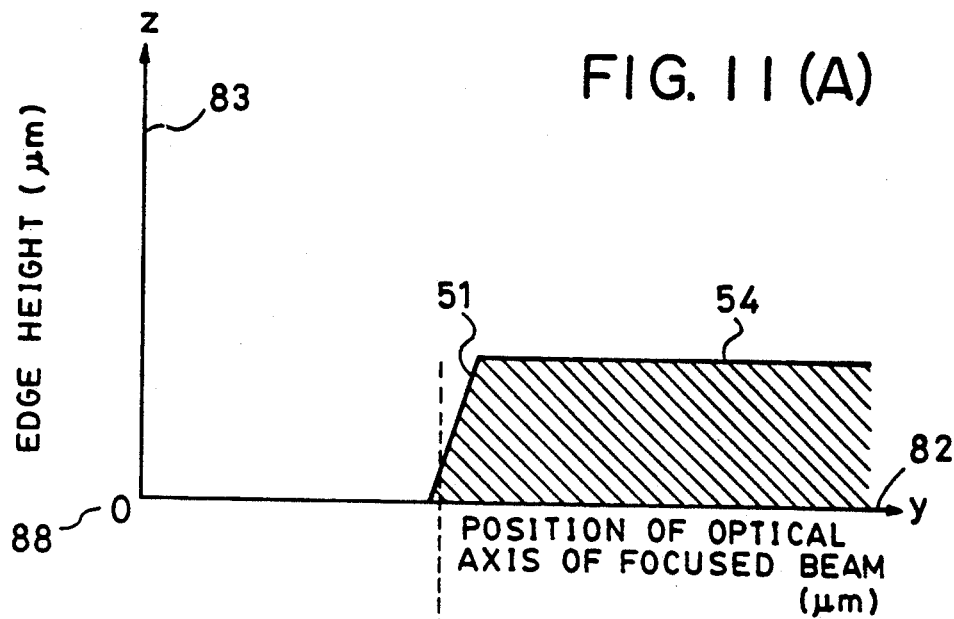
FIGS. 11(A) through 11(C) are diagrams illustrating the cross section of an edge and edge-position detection.

The method of evaluating the edge in the present embodiment will be further described in detail with reference to FIGS. 11(A) through 11(C). FIG. 11(A) is a cross-sectional view of the edge 51 on the object having the fine structure. For the sake of convenience, it is assumed that the edge 51 is uniform in the direction perpendicular to the plane of FIG. 11(A). The origin 88 is a reference point of the scanning system 6 of the apparatus. A point of the y axis 82 indicates the position of the optical axis of the focused light beam with respect to the edge 51. The z axis represents the direction of the height of the edge. The focused light beam is scanned with respect to the edge 51 in the direction of the y axis 82. When the edge portion is illuminated by the focused light beam, the scattering distribution characteristics change in accordance with the position of the optical axis, as shown in FIGS. 8(A) through 8(C). When a local minimum value is produced in the scattering distribution characteristics as a result of scanning of the focused light beam, the position (the scattering angle) of the local minimum value depends upon the height of the edge. Hence, in the present embodiment, the height of the edge is obtained by using a previously provided correspondence table or a previously provided relational expression between the edge height and the position of the local minimum value.

Figure 11B:
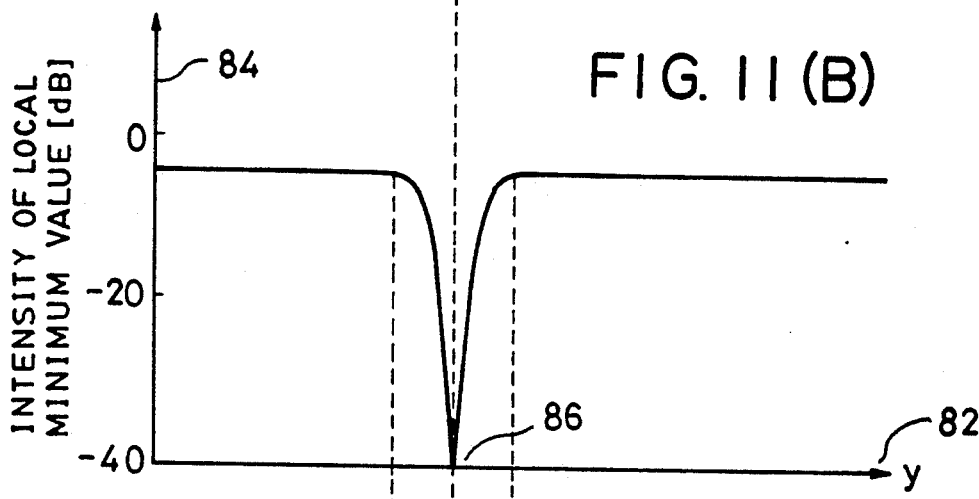

FIG. 11(B) shows how the intensity of the detected local minimum value changes as a result of scanning. In FIG. 11(B), the ordinate 84 represents the intensity of the extreme value in the scattering distribution characteristics. FIG. 11(C) shows the differential value of the intensity of the local minimum value. In FIG. 11(C), the ordinate 85 represents the differential value of the intensity of the local minimum value. In FIG. 11(B), a position 86 where the intensity of the local minimum value in the scattering distribution characteristics has a smallest value differs in accordance with the tilt angle and the height of the edge 51, as shown in FIGS. 9(A) through 10(B). The rate of change (the differential value) of the intensity of the local minimum value depends upon the tilt angle of the edge 51. The change is greater as the tilt angle is closer to 90 degrees.

Figure 11C:
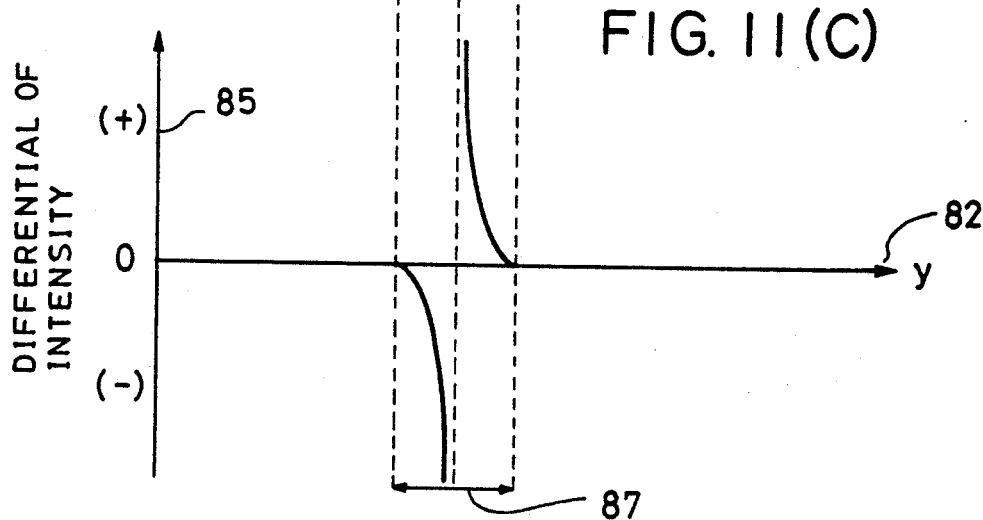

Accordingly, in the present embodiment, for example, as shown in FIG. 11(C), by obtaining the differential value of the intensity of the local minimum value and the value of a width 87, the tilt angle of the edge is obtained using a previously provided correspondence table. As described above, since the height of the edge can be obtained from the position of the local minimum value, the shape of the edge is evaluated according to the above-described analysis.

Figure 12:
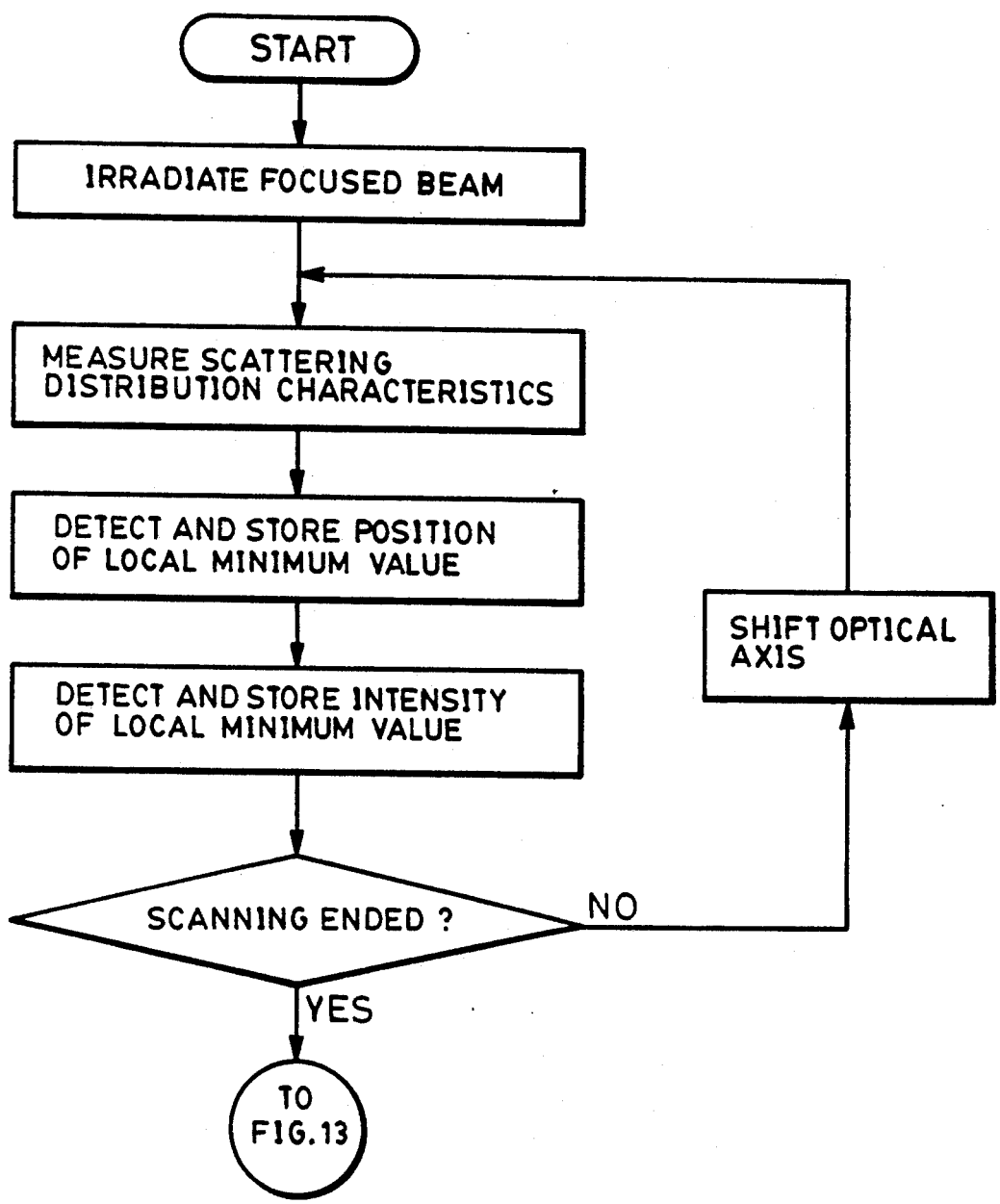
FIGS. 12 and 13 are flowcharts of the edge-position detection shown in FIGS. 11(B) and 11(C)
Figure 13:
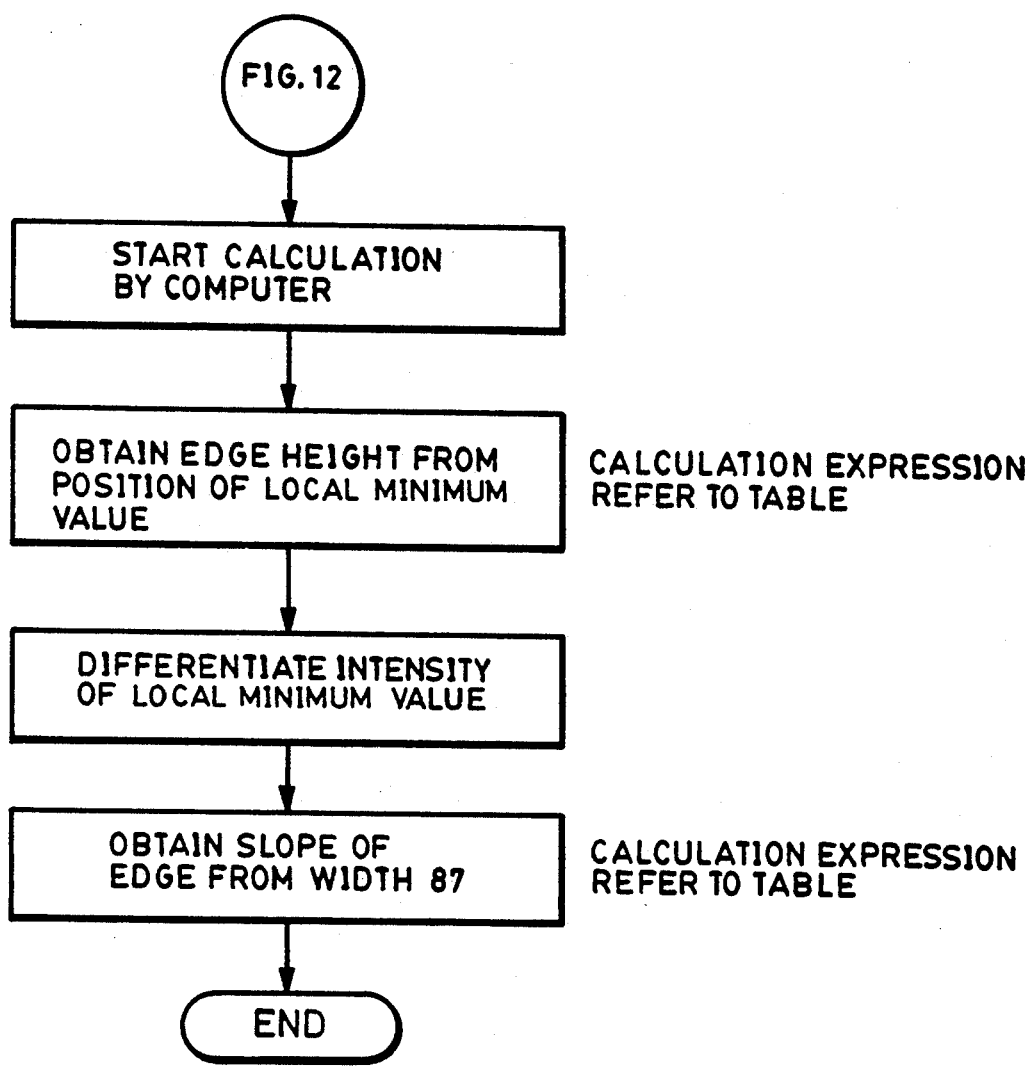

FIGS. 12 and 13 are flowcharts of the above-described processing.

Although, in the foregoing explanation, characteristics of one-dimensional spatial distribution of scattered light produced by a predetermined cross section of the object 2 have been shown, three-dimensional evaluation of a fine structure of the object 2 may be performed by detecting spatial distribution characteristics with respect to a plurality of different cross sections in place of spatial distribution characteristics with respect to one cross section, or detecting all spatical distribution characteristics of scattered light which is three dimensionally spread within a predetermined range of space.

Although in the present embodiment, the object 2 is scanned with the light beam while moving the object 2, a scanning system which is telecentric at the side of the object 2 may be used, light may be continuously deflected using a scanner, such as a polygon mirror, a rotating parallel plane or the like, and the object 2 may be scanned with a vertically incident light beam.

The apparatus of the present embodiment may be used not only for detecting the structure of a pattern formed on an object, but also for detecting scratches or foreign particles, such as dust particles or the like, present on an object, as will be described later. For example, in the production process of semiconductor devices, since the presence of foreign particles adhering to a reticle or a mask on which circuit patterns are formed causes a problem, apparatuses for detecting foreign particles are used. The apparatus of the present embodiment can detect foreign particles if the object 2 to be inspected comprises a reticle or a mask on which circuit patterns are formed. In such a case, a shading filter for shading diffracted light from the circuit patterns on the reticle or the mask from the photoelectric detector 43 may be provided, and light scattered by a foreign particle may be selectively received by the photoelectric detector 43 via the shading filter.

Figure 14:
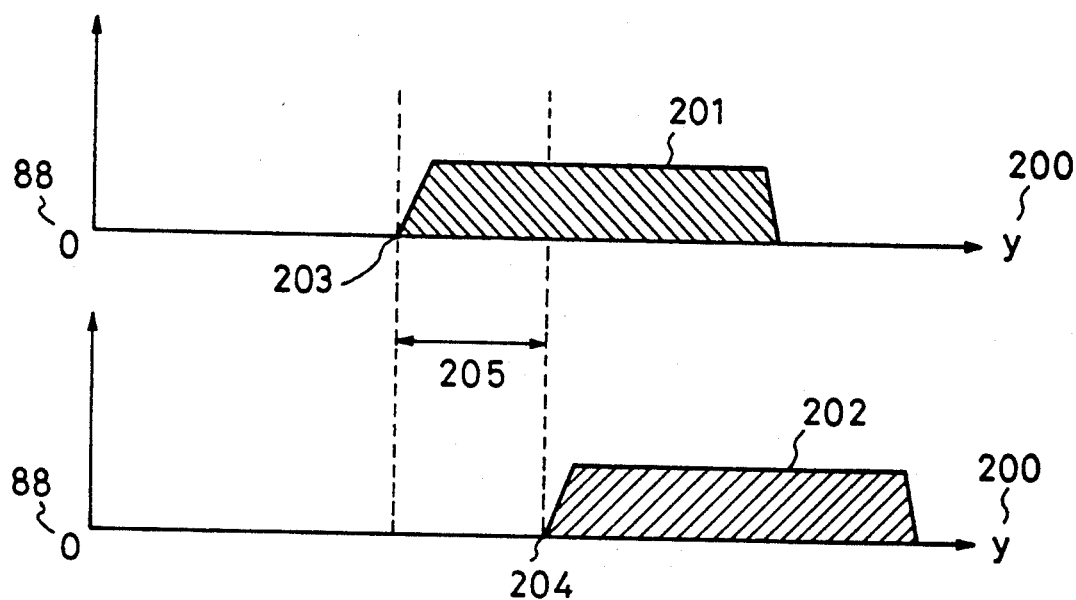
FIG. 14 is a diagram illustrating a positioning operation of edges according to a third embodiment of the present invention.

FIG. 14 is a diagram illustrating the cross sections of edges on two objects when the two objects are positioned using the fine structure evaluation apparatus shown in FIG. 6 according to a third embodiment of the present invention.

In FIG. 14, there are shown the cross section 201 of an edge on one object, serving as a reference for positioning processing, and the cross section 202 of an edge on another object which is to be positioned with respect to the reference object 201. The y axis 200 represents the scanning direction of the focused light beam 35 onto the object in the fine structure evaluation apparatus of the present embodiment. The origin 88 is a reference point of the scanning system 6 of the apparatus.

In positioning processing, the edge position 203 of the reference object 201 is first detected as a result of scanning of the focused light beam, and the computer 7 shown in FIG. 6 stores this position. Subsequently, the scanning is switched to the object 202, the edge position 204 is detected, and the object 202 is moved so that the edge position 204 coincides with the edge position 203 of the reference object 201 which has been positioned. Thus, the two objects are positioned with each other, that is, the position of the object 201 is made to coincide with the position of the reference object 201.

Next, the principle of the positioning processing will be explained. The edge position 203 of the reference object 201 is detected as a result of scanning of the focused light beam, and the computer 7 stores this position. Subsequently, the scanning is switched to the object 202, the edge position 204 is detected in the same manner as described above, and the computer 7 obtains the distance 205 between the two edges 203 and 204. By moving the position of the object 202 by the scanning system 6 including a driving means by a distance corresponding to the distance 205, positioning processing of the object 202 with the reference object 201 is performed.

Figure 15A:
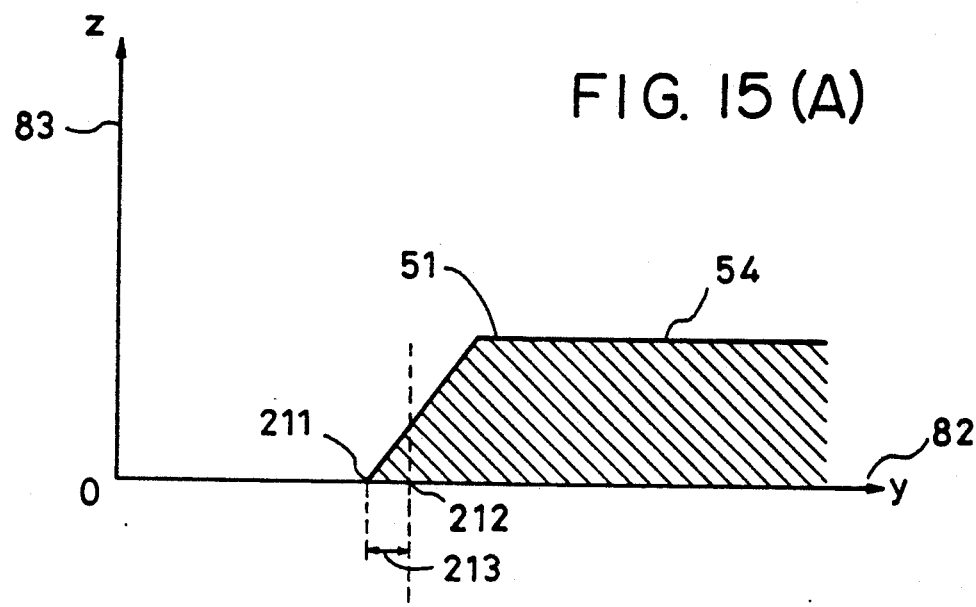
FIGS. 15(A) through 15(C) are diagrams illustrating the principle of the positioning operation shown in FIG. 14.
Figure 15B:
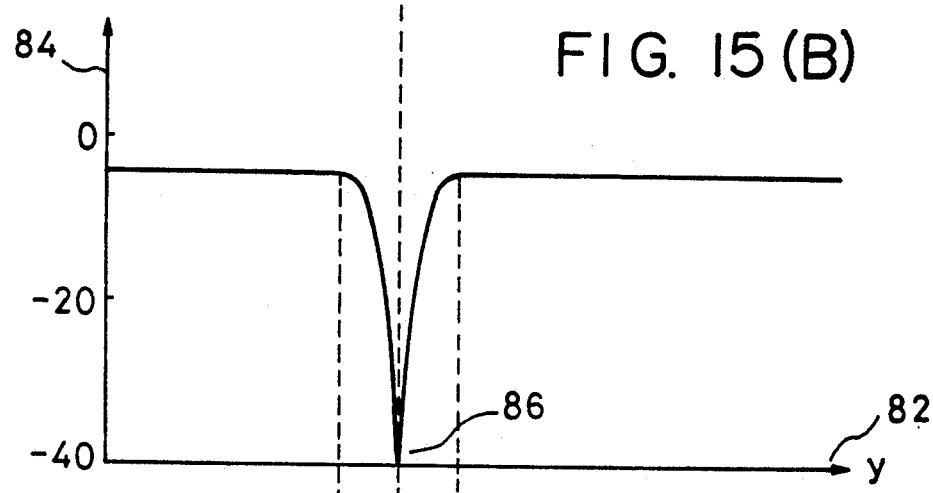
Figure 15C:
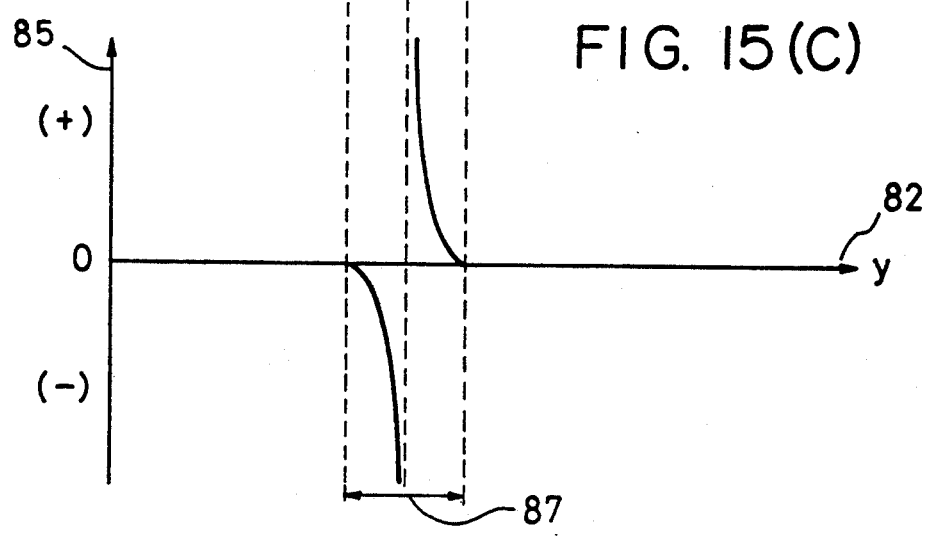

Next, an explanation will be provided of a method of detecting the edge position for positioning processing with reference to FIGS. 15(A) through 15(C). FIG. 15(A) is a cross-sectional view of an edge portion on an object having a fine structure which is similar to the objects 201 and 202 shown in FIG. 14. The edge 51 is assumed to be uniform in the direction perpendicular to the plane of FIG. 15(A). The y axis 82 represents the position of the optical axis of focused light beam with respect to the edge 51. The z axis 83 represents the direction of the height of the edge 51. The focused light beam is scanned with respect to the edge 51 in the direction of the y axis 82. When the edge 51 is illuminated by the focused light beam, the scattering distribution characteristics change in accordance with the position of the optical axis, as shown in FIGS. 7 and 8(A) through 8(C). When a local minimum value is produced in the scattering distribution characteristics as a result of scanning of the focused light beam, the position (the scattering angle) of the local minimum value depends upon the height of the edge. Hence, in the present embodiment, the height of the edge is obtained using a previously provided correspondence table or a previously provided relational expression between the edge height and the position of the local minimum value.

FIG. 15(B) shows how the intensity of the detected local minimum value changes as a result of scanning. In FIG. 15(B), the ordinate 84 represents the intensity of the local minimum value in the scattering distribution characteristics. FIG. 15(C) shows the differential value of the intensity of the local minimum value. In FIG. 15(C), the ordinate 85 represents the differential value of the intensity of the local minimum value. In FIG. 15(B), a position 212 where the intensity of the local minimum value in the scattering distribution characteristics has a smallest value depends upon the tilt angle and the height of the edge 51, as shown in FIGS. 9(A) through 10(B). Hence, the position 212 in general does not coincide with the end point 211 of the edge 51. However, as described above, it is possible to obtain the height of the edge 51.

In the present embodiment, the tilt angle of the edge 51 is obtained by the following method, whereby the distance 213 is obtained. That is, the rate of change (the differential value) of the intensity of the local minimum value depends upon the tilt angle of the edge 51. The change is greater as the tilt angle is closer to 90 degrees. Hence, in the present embodiment, for example, as shown in FIG. 15(C), by obtaining the differential value of the intensity of the local minimum value and the value of the width 87, the tilt angle of the edge 51 is obtained using a previously provided correspondence table or a relational expression. By obtaining the tilt angle and the height of the edge 51, the position 212 is obtained from a previously provided correspondence table or a relational expression. When the position 212 is obtained, since the height and the tilt angle of the edge 51 are known, the position of the end point 211 of the edge 51 and the distance 213 can be determined.

By performing the above-described operation for the reference object 201 and the object 202, and moving the object 202 by the scanning system 6 shown in FIG. 6 so that the edge position 204 of the object 202 coincides with the determined edge position 203 of the reference object 201, a positioning operation is performed.

FIGS. 16 and 17 are flowcharts of the above-described processing. In FIGS. 16 and 17, processing from a process 1001 of irradiating the focused light beam to a process 1002 of detecting the end point 211 is operation (A).

Figure 18:
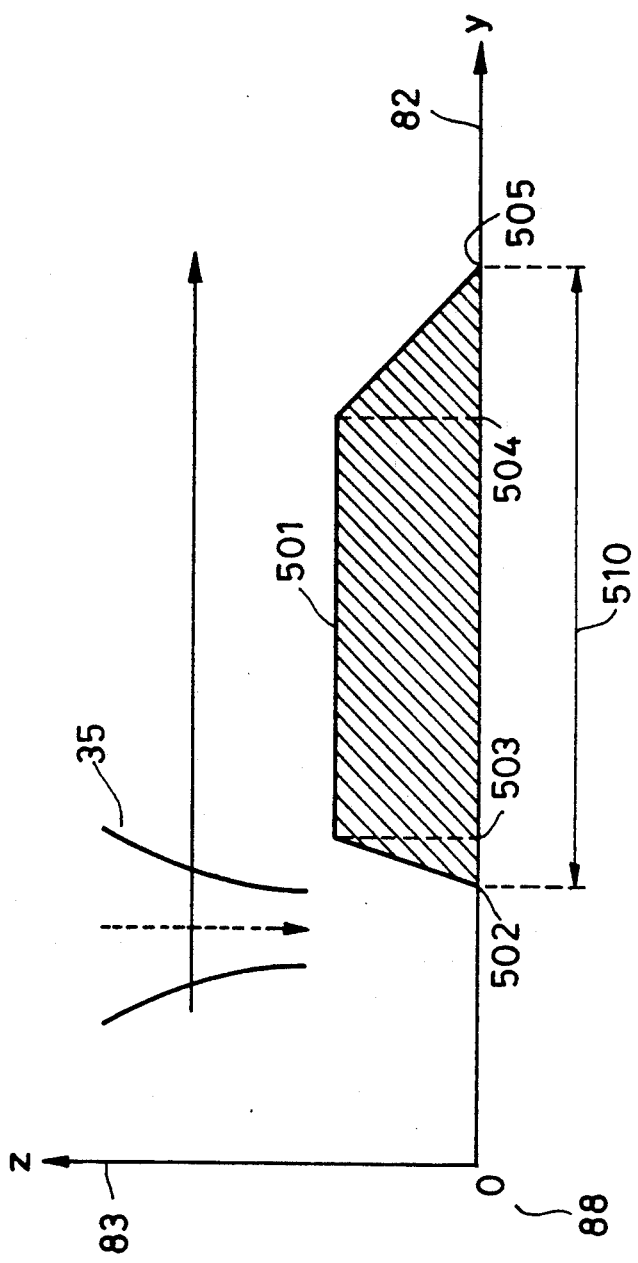
FIG. 18 is a diagram illustrating measurement of a line width of a pattern according to a fourth embodiment of the present invention.

FIG. 18 is a diagram illustrating the cross section of a pattern line to be measured in a fourth embodiment of the present invention, wherein the line width of a pattern on an object is measured using the fine structure evaluation apparatus shown in FIG. 6.

In FIG. 18, there is shown a vertical cross-sectional view of a pattern line 501 whose width is to be measured. The origin 88 is a reference point of the scanning system 6 of the apparatus. The y axis 82 represents the scanning direction of the focused light beam 35 with respect to the object in the apparatus. The z axis 83 represents the direction of the height of the pattern line 501. Reference numerals 502 and 505 represent lower end points of the pattern line 501, and reference numerals 503 and 504 represent upper end points of the pattern line 501.

It is assumed that the distance 510 between the end points 502 and 505 is measured as the width of the pattern line 501. The principle of measuring the width of the pattern line comprises detecting the lower end point 502 of the pattern line 501 as a result of scanning of the focused light beam, and storing this position in the computer 7. Subsequently, the lower end point 505 is detected in the same manner, and this position is also stored in the computer 7. By obtaining the positions of the lower end points 502 and 505, the computer 7 calculates the pattern line width 510.

Figure 19A:
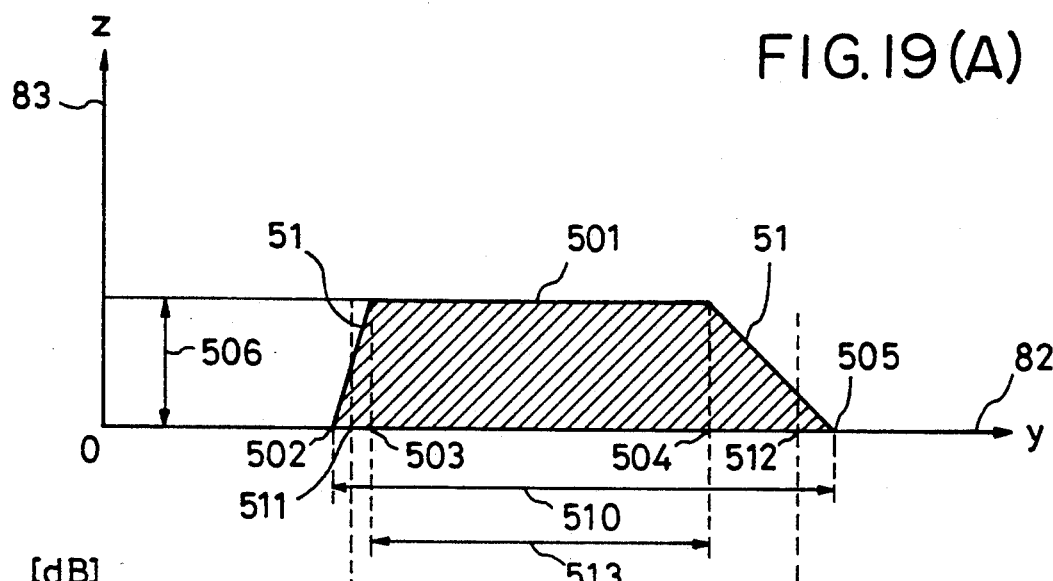
FIGS. 19(A) through 19(C) are diagrams illustrating the principle of the measurement of the line width of the pattern shown in FIG. 18.
Figure 19B:
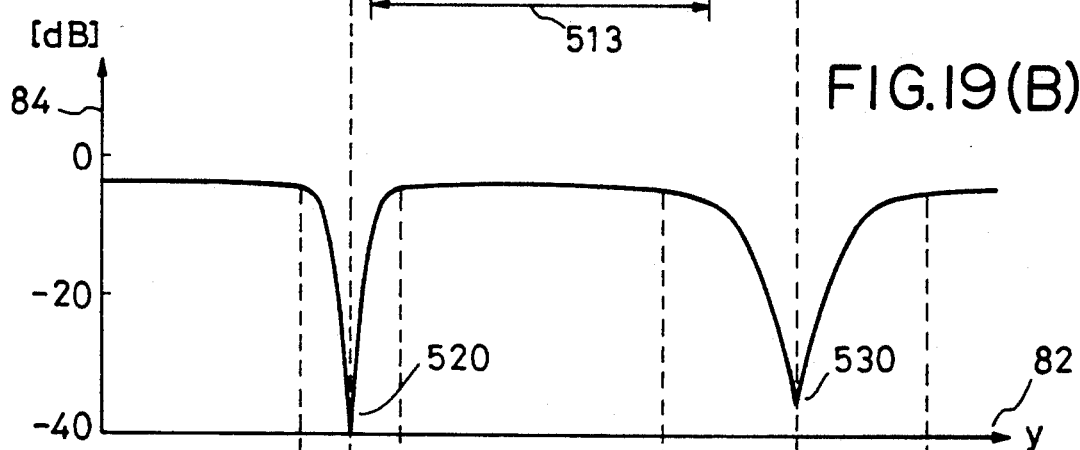
Figure 19C:
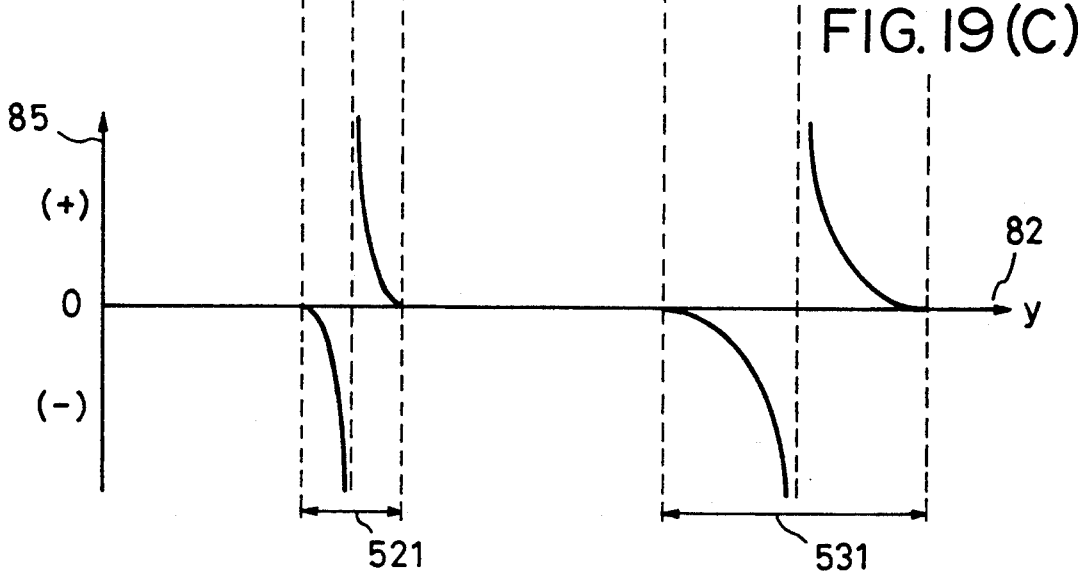

Next, an explanation will be provided of a method of detecting positions of respective end points for measuring the pattern line width with reference to FIGS. 19(A) through 19(C). FIG. 19(A) is a cross-sectional view of the fine pattern line 501 on the object. The pattern line 501 is assumed to be uniform in the direction perpendicular to the plane of FIG. 19(A). The y axis 82 represents the position of the optical axis of the focused light beam with respect to the edge 51. The z axis 83 represents the direction of the height of the pattern line 501. The focused light beam 35 is scanned with respect to the pattern line 501 in the direction of the y axis 82. When the edge portion is illuminated by the focused light beam, the scattering distribution characteristics change in accordance with the position of the optical axis, as shown in FIGS. 8(A) through 8(C). When a local minimum value is produced in the scattering distribution characteristics as a result of scanning of the focused light beam, the position (the scattering angle) of the local minimum value depends upon the height 506 of the pattern line. Hence, in the present embodiment, the height of the pattern line 506 is obtained using a previously provided correspondence table or a previously provided relational expression between the height and the position of the local minimum value.

FIG. 19(B) shows how the intensity of the detected local minimum value changes as a result of scanning. In FIG. 19(B), the ordinate 84 represents the intensity of the local minimum value in the scattering distribution characteristics. FIG. 19(C) shows the differential value of the intensity of the local minimum value. In FIG. 19(C), the ordinate 85 represents the differential value of the intensity of the local minimum value.

In FIG. 19(B), positions 511 and 512 of the smallest values 520 and 530 of the intensity of the local minimum value in the scattering distribution characteristics depend upon the tilt angle and the height of the edge portion of the pattern line 501, in the same manner as shown in FIGS. 9(A) through 10(B). Hence, the positions 511 and 512 in general do not coincide with the end points 502 and 505 of the edge 51. However, as described above, it is possible to obtain the height of the pattern line 501.

In the present embodiment, the tilt angle of the edge portion of the pattern line is obtained by the following method, whereby the positions 502 and 505 are obtained using information on the tilt angle and the height. That is, the rate of change (the differential value) of the intensity of the local minimum value depends upon the tilt angle of the edge portion of the pattern line 501. The change is greater as the tilt angle is closer to 90 degrees.

Hence, in the present embodiment, for example, as shown in FIG. 19(C), by obtaining the differential value of the intensity of the local minimum value and the values of the widths 521 and 531, the tilt angle of the edge portion is obtained using a previously provided correspondence table or a relational expression. That is, the tilt angle and the height of the edge portion of the pattern line 501 are obtained, and the positions 502 and 505 are determined from these values using a previously provided correspondence table or relational expression. Thus, the distance 510 corresponding to the width of the pattern line 501 is obtained.

Figure 20:
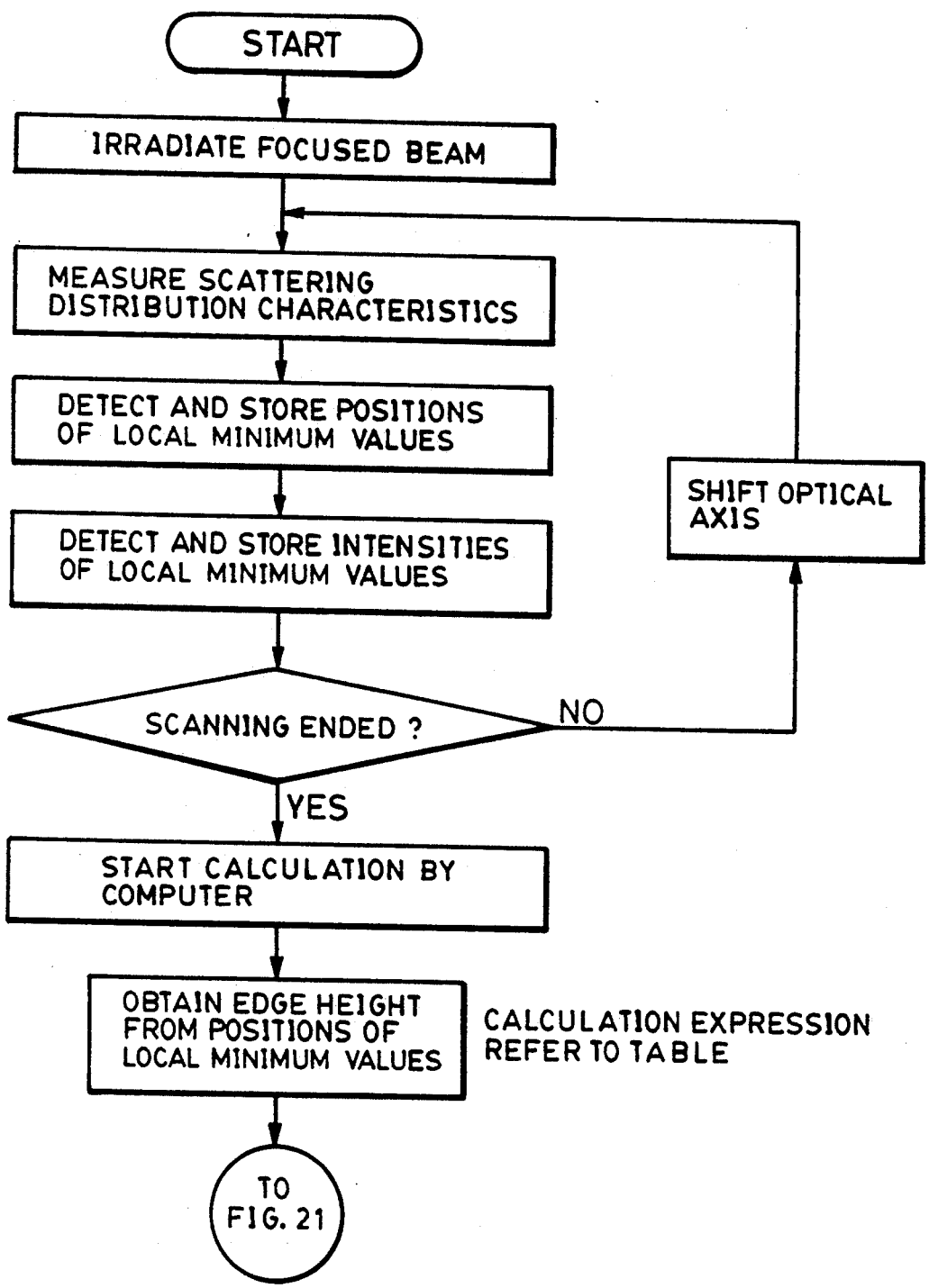
FIGS. 20 and 21 are flowcharts of the measurement of the line width of the pattern shown in FIGS. 19(A) through 19(C)
Figure 21:
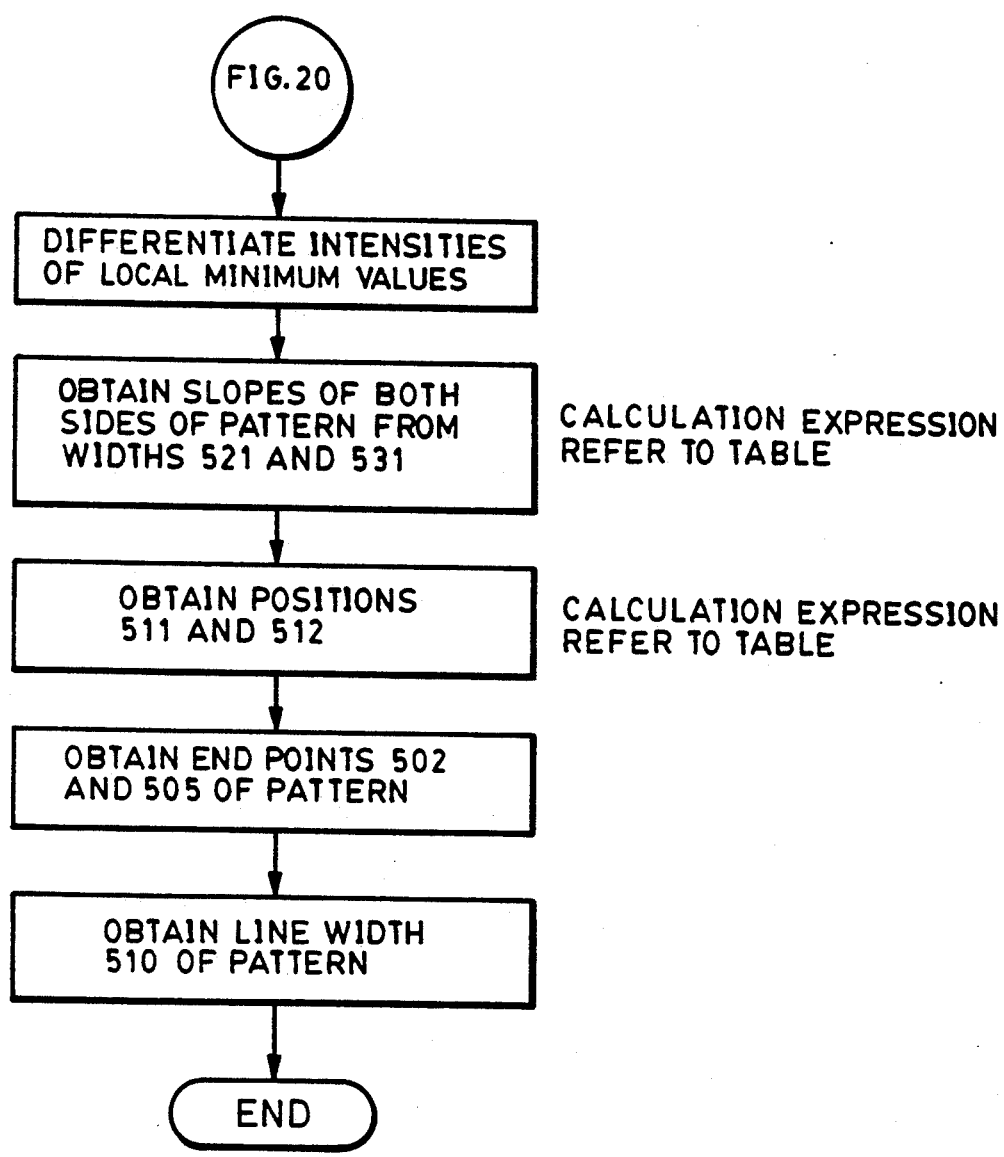

FIGS. 20 and 21 are flowcharts of the above-described processing.

In the present embodiment, the positions 503 and 504 can be obtained as well as the positions 502 and 505, whereby the width 513 of the upper portion of the pattern line 501 can be obtained in the same manner as described above.

Next, an explanation will be provided of a foreign particle inspection apparatus which detects foreign particles adhering to the surface of a reticle or a wafer while discriminating the foreign particles from a fine structure, such as a circuit pattern or the like.

Figure 22:
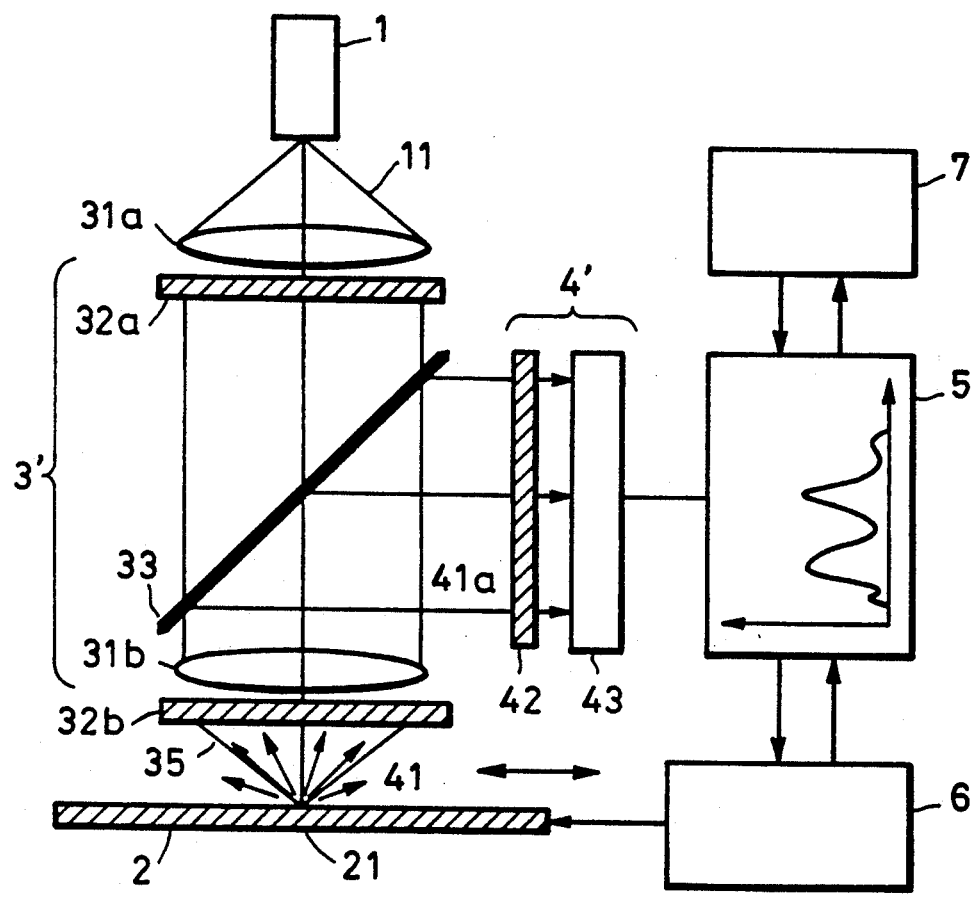
FIG. 22 is a schematic diagram of a principal part of a foreign particle inspection apparatus according to a fifth embodiment of the present invention.

FIG. 22 is a schematic diagram of a principal part of a foreign particle inspection apparatus according to a fifth embodiment of the present invention. The basic configuration of the apparatus is substantially the same as the edge evaluation apparatus shown in FIG. 6. Respective components in the present embodiment will be sequentially explained, although some components are the same as those shown in FIG. 6.

In FIG. 22, there are shown a light source means 1, and an object 2 to be inspected having a fine structure. An illuminating optical system 3' focuses light from the light source means 1 to illuminate a minute region 21 on the object 2. The illuminating optical system 3' includes a lens system 31a and a filter system 32a at the side of the light source means 1, a lens system 31b and a filter system 32b at the side of the object 2, and a beam splitter 33 for introducing scattered light from the object 2 to a detection system 4' between the filter system 32a and the lens system 31b.

The detection system 4' includes a filter system 42 for detecting scattering distribution characteristics of light 41 scattered by the fine structure of the object 2, and a photoelectric detector 43, such as a one-dimensional CCD, a two-dimensional CCD or the like. A signal processing system 5 analyzes the fine structure of the object 2 from signals representing the scattering distribution characteristics detected by the detection system 4'. A scanning system 6 relatively scans the object 2 with the focused light 35. A computer 7 performs calculation processing of data processed by the signal processing system 5 to detect the presence of fine particles on the object 2.

As in the edge evaluation apparatus shown in FIG. 6, in the present embodiment, for example, a semiconductor laser, a light source for emitting a coherent light beam, such as a He-Ne laser, an Ar laser or the like, a light source for emitting an incoherent light beam such as a light-emitting diode, a halogen lamp or the like may be used as the light source means 1. A light source which is suitable for a fine structure to be evaluated is selected on every occasion.

In the present embodiment, light 11 emitted from the light source means 1 is first focused onto the minute region 21 on the object 2 having the fine edge structure by means of the illuminating optical system 3'. The light beam focused on the object 2 is scattered with scattering distribution characteristics which depend upon the edge structure within the minute region 21. The scattered light 41 is reflected by the beam splitter 33 after passing through the filter system 32b and the lens system 31b provided at the side of the object 2 to be separated as scattered light 41a, which is introduced into the detection system 4'. An ND (neutral density) filter for absorbing a constant ratio of light intensity, a polarizing filter, a low-pass filter or the like which is most suitable for measuring the scattering distribution characteristics is selected as the filter used in the illuminating optical system 3' or the detection system 4'.

When the scattered light 41a is parallel light in the detection system 4', the minute region 21 and the detection surface of the detection system 4' are in the relationship of a Fourier transform. At that time, the detection system 4' measures the scattering distribution characteristics in a far-field region for the minute region 21 on the object 2. The scattering distribution characteristics of the scattered light 41a introduced in the detection system 4' are detected by the photoelectric detector 43 of the detection system 4' while being subjected to photoelectric conversion. The detected scattering distribution characteristics are analyzed by the signal processing system 5. The result of the analysis is processed by the computer 7, and the presence of foreign particles is checked by separating signals representing light scattered by the edge structure from signals representing light scattered by foreign particles.

At that time, by relatively scanning the object 2 with the focused light beam 35 by means of the scanning system 6, the position of the minute region 21 on the object 2 changes, whereby the scattering distribution characteristics change. The changes in the scattering distribution characteristics are sequentially analyzed and processed by the signal processing system 5 and the computer 7, whereby foreign particle inspection on the entire surface of the object 2 to be checked is performed.

Next, an explanation will be provided of a method of checking the presence of foreign particles on the surface of the object 2 by analyzing the scattering distribution characteristics caused by the object 2.

Figure 23:
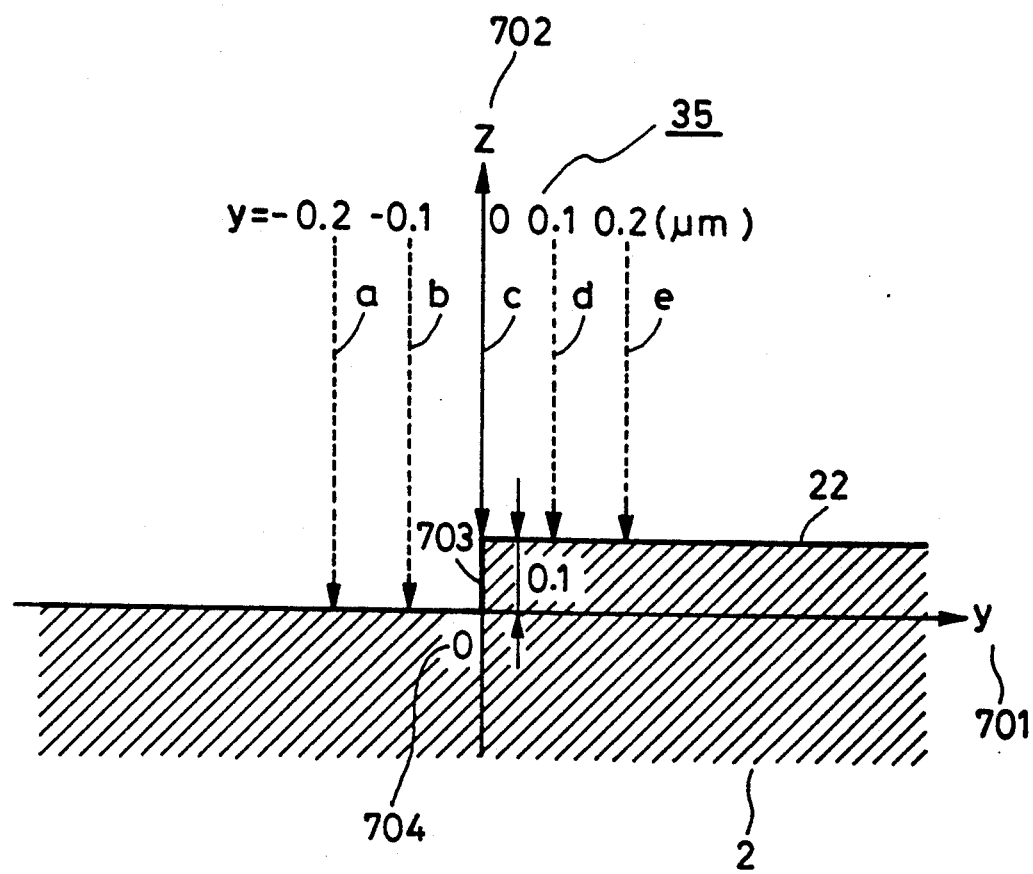
FIG. 23 is a diagram illustrating an edge portion of an object.
Figure 24A:
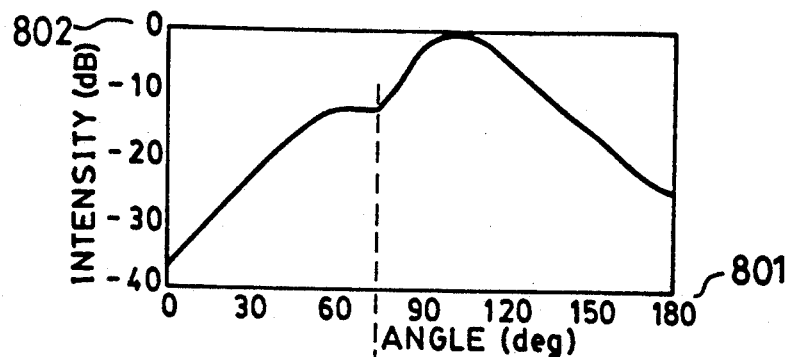
FIGS. 24A through 24E are diagrams illustrating scattering distribution characteristics when the edge is optically scanned.
Figure 24B:
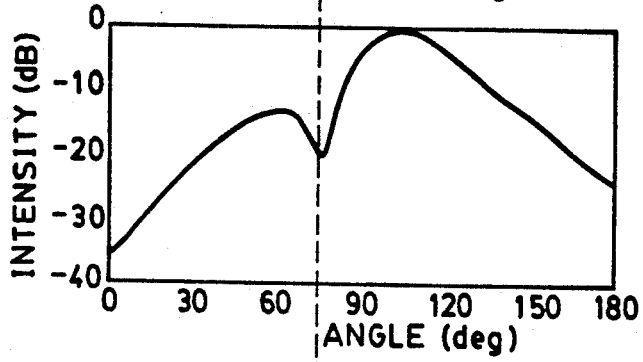
Figure 24C:
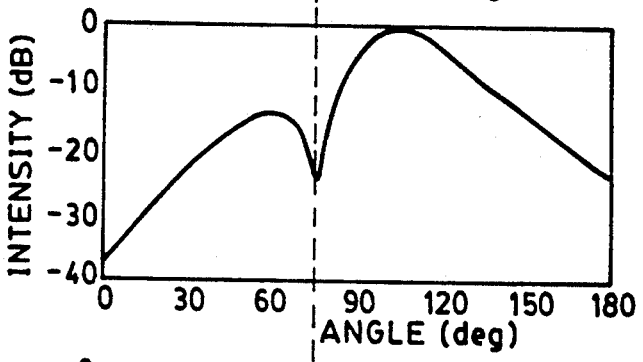
Figure 24D:
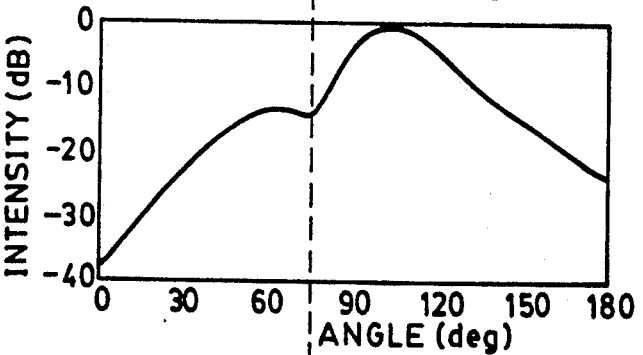
Figure 24E:
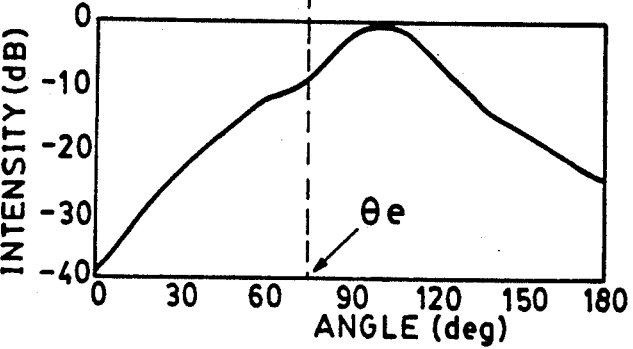

FIG. 23 is a cross-sectional view of the edge including the coordinate system when the focused light beam is projected onto the object 2 having the fine edge structure by means of the illuminating optical system 3'. A boundary-surface edge portion 703 of the object 2 is uniform in the direction perpendicular to the plane of FIG. 23, and comprises a perfect conductor. The origin 704, the y axis 701 and the z axis 702 are set as the coordinate system of the edge 703. If the focused light beam 35 is projected onto the edge 703 so that the optical axis of the focused light beam 35 is parallel to the z axis (that is, perpendicular to the boundary surface 22 of the object 2), the focused light beam 35 is scattered with certain scattering distribution characteristics.

The scattering distribution characteristics are measured by the detection system 4' in a far field region separated from the origin 704 by about 1,000 multiples of the wavelength of the light. The height of the edge 703 is about 0.1 $\mu$m. A Gaussian beam having a wavelength of 0.6328 $\mu$m and a beam spot diameter of 1.0 $\mu$m is used as the focused light beam 35, and the position of the beam waist is arranged to be on the y axis. The edge 703 is scanned with the above-described focused light beam 35 in the direction of the y axis by means of the scanning system. The scattering distribution characteristics measured when the optical axis of the focused light beam 35 is at positions "a", "b", "c", "d" and "e" shown in FIG. 23 become as shown in FIGS. 24A, 24B, 24C, 24D and 24E, respectively.

FIGS. 24A through 24E are diagrams showing the scattering distribution characteristics when the above-described edge 703 is optically scanned. In FIGS. 24A through 24E, the abscissa 801 represents the scattering direction of light scattered by the edge structure of the object, in which the counterclockwise direction from the positive direction of the y axis 201 around the origin 704 is assumed to be the positive direction. The ordinate 802 represents the intensity of the measured scattered light. The unit of the intensity is a decibel, and 0 dB corresponds to the maximum value of the intensity of measured scattered light when the focused light beam is projected onto the boundary surface 22 of the object 2 which comprises a perfect conductor. The following items hold from the scattering distribution characteristics shown in FIGS. 24A through 24E.

(4-1) The position $\theta e$ (the scattering angle) of the local minimum value does not change in accordance with scanning of the focused light beam (the position of the optical axis in the y-axis direction), but only depends upon the wavelength of the focused light beam and the height of the edge. Accordingly, when the wavelength of the focused light beam and the height of the edge of the object are previously known, it is possible to know at which position the local minimum value is produced as a result of optical scanning for the edge using a previously provided correspondence table or a previously provided relational expression between the height of the edge and the position of the local minimum value. Furthermore, in optical scanning for the edge, it is possible to know the height of the edge from the position of the local minimum value in the scattering distribution characteristics.

(4-2) When the step of the edge of the object is equal to or less than $\lambda/2$, only one local minimum value is produced at a position (scattering angle) $\theta e$ which depends upon the height in the scattering distribution characteristics.

(4-3) The intensity of the local minimum value changes in accordance with the position of the optical axis relative to the edge, and has a smallest value near the edge.

As described above, in the present embodiment, by utilizing the fact that the position of the local minimum value in the scattering distribution characteristics obtained as a result of scanning of the focused light beam for the edge is determined by the step of the edge if the conditions of the projected focused light beam are determined, a scattering signal from a dust particle is separated from changes of the local minimum value.

Next, an explanation will be provided of how scattering distribution characteristics change when a dust particle adheres to the surface of an object.

Figure 25:
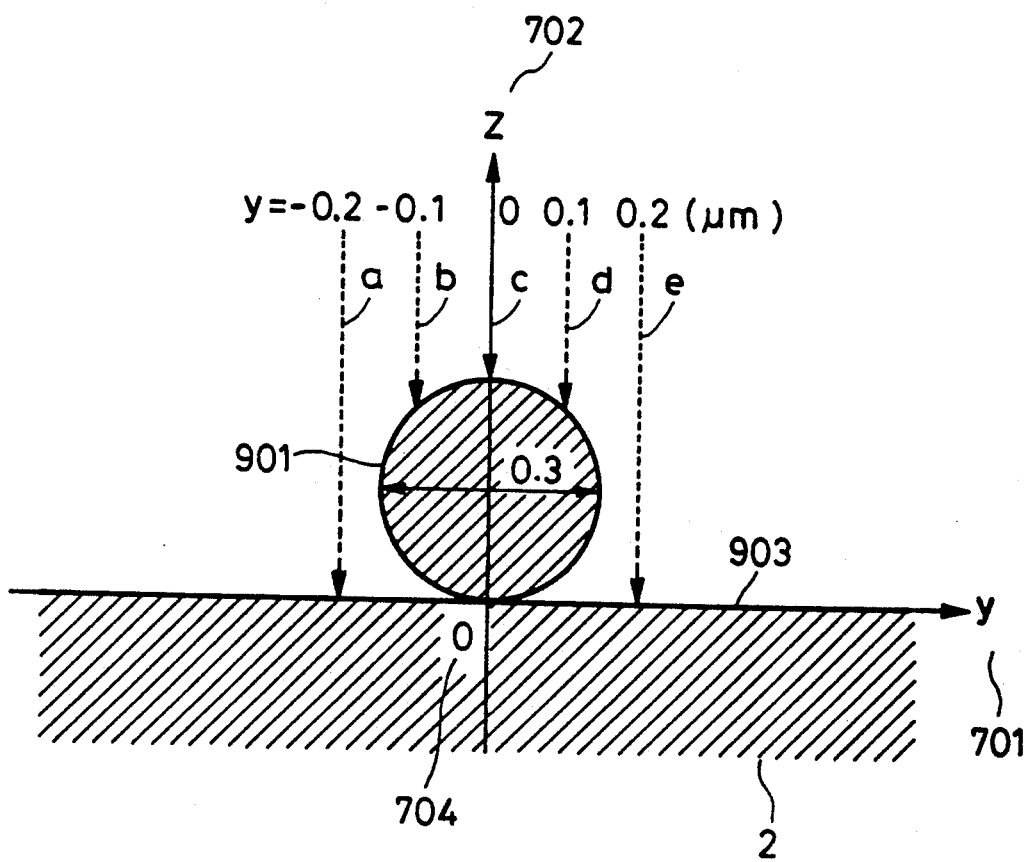
FIG. 25 is a diagram illustrating a dust particle adhering to the surface of the object.
Figure 26A:
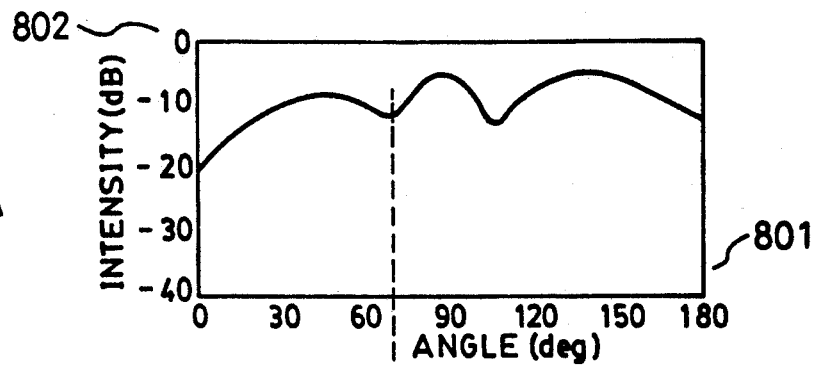
FIGS. 26A through 26E are diagrams illustrating scattering distribution characteristics when the dust particle shown in FIG. 25 is optically scanned.
Figure 26B:
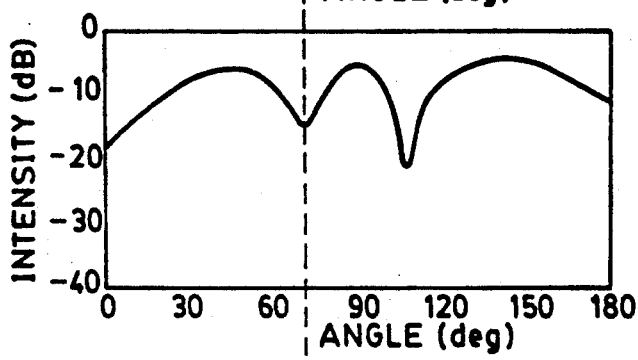
Figure 26C:
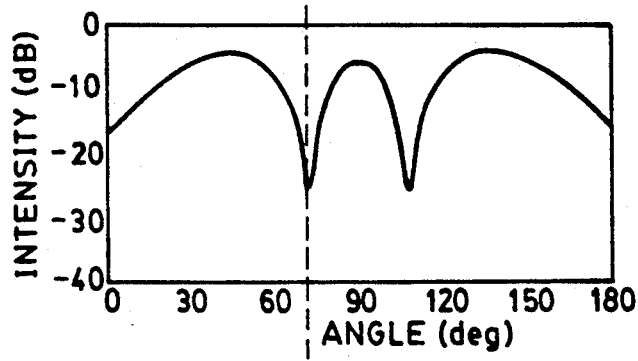
Figure 26D:
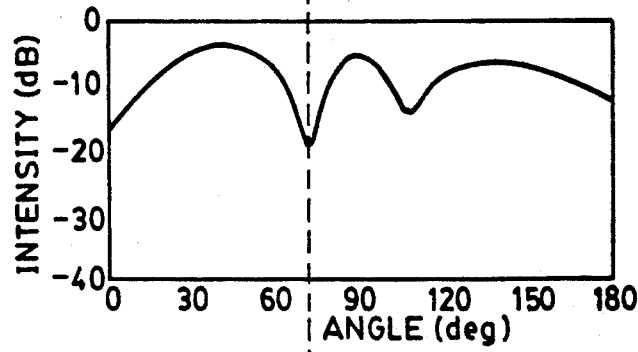
Figure 26E:
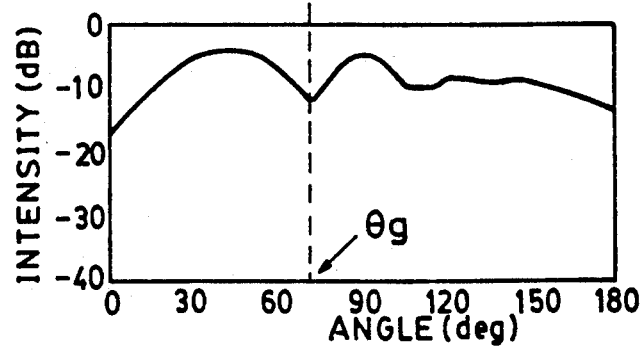

FIG. 25 is a cross-sectional view including the coordinate system when the focused light beam is projected onto the object 2, to whose surface a spherical dust particle adheres, from the illuminating optical system 3'. The dust particle 901 has the shape of a sphere having a diameter of 0.3 $\mu$m. A boundary surface 903 of the object 2 is uniform in the direction perpendicular to the plane of FIG. 25 (the x direction). The origin, the y axis and the z axis of the coordinate system are set as indicated by reference numerals 704, 701 and 702, respectively.

The scattering distribution characteristics of scattered light are measured in a far field region separated from the origin 704 by about 1,000 multiples of the wavelength of the light. As in the case of FIG. 23, a Gaussian beam having a wavelength of 0.6328 $\mu$m and a beam spot diameter of 1.0 $\mu$m is used as the projected focused light beam 35, and the position of the beam waist is arranged to be on the y axis. The dust particle 901 is scanned with the above-described focused light beam by means of the scanning system in the y-axis direction. The scattering distribution characteristics measured when the optical axis of the focused light beam corresponds to positions "a", "b", "c", "d" and "e" shown in FIG. 25 become as shown in FIGS. 26A, 26B, 26C, 26D and 26E, respectively.

FIGS. 26A through 26E show scattering distribution characteristics by the dust particle 901 shown in FIG. 25. The abscissa 801 and the ordinate 802 shown in FIGS. 26A through 26E are the same as those in FIGS. 24A through 24E. The following items hold from FIGS. 26A through 26E.

(5-1) Unlike the scattering distribution characteristics measured as a result of optical scanning for the edge, two local minimum values are produced in the scattering distribution characteristics by the dust-particle in the above-described conditions of the focused light beam.

(5-2) The position $\theta g$ where the local minimum value is produced is different from the position $\theta e$ of the local minimum value when the edge is optically scanned.

From these items and the items described with respect to FIGS. 24A through 24E, it can be said that if two local minimum values are present, or a local minimum value is present at a position different from the previously calculated position $\theta e$ of the local minimum value in the scattering distribution characteristics obtained as a result of optical scanning for the surface of the object 2, it is possible to determine that something different from the edge structure or a fine foreign particle is present within the minute region on the surface of the object 2 illuminated by the focused light beam.

Next, an explanation will be provided of a case in which a dust particle adheres in the neighborhood of the edge of the object 2.

Figure 27:
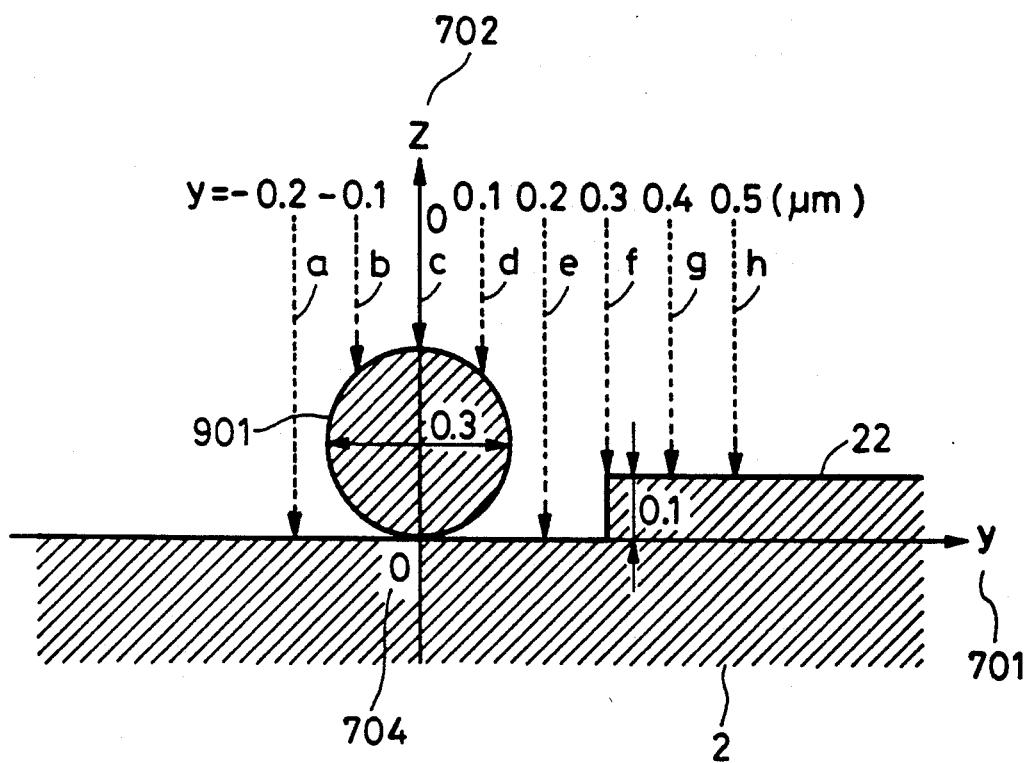
FIG. 27 is a diagram illustrating a dust particle adhering to the neighborhood of the edge of the object.
Figure 28:
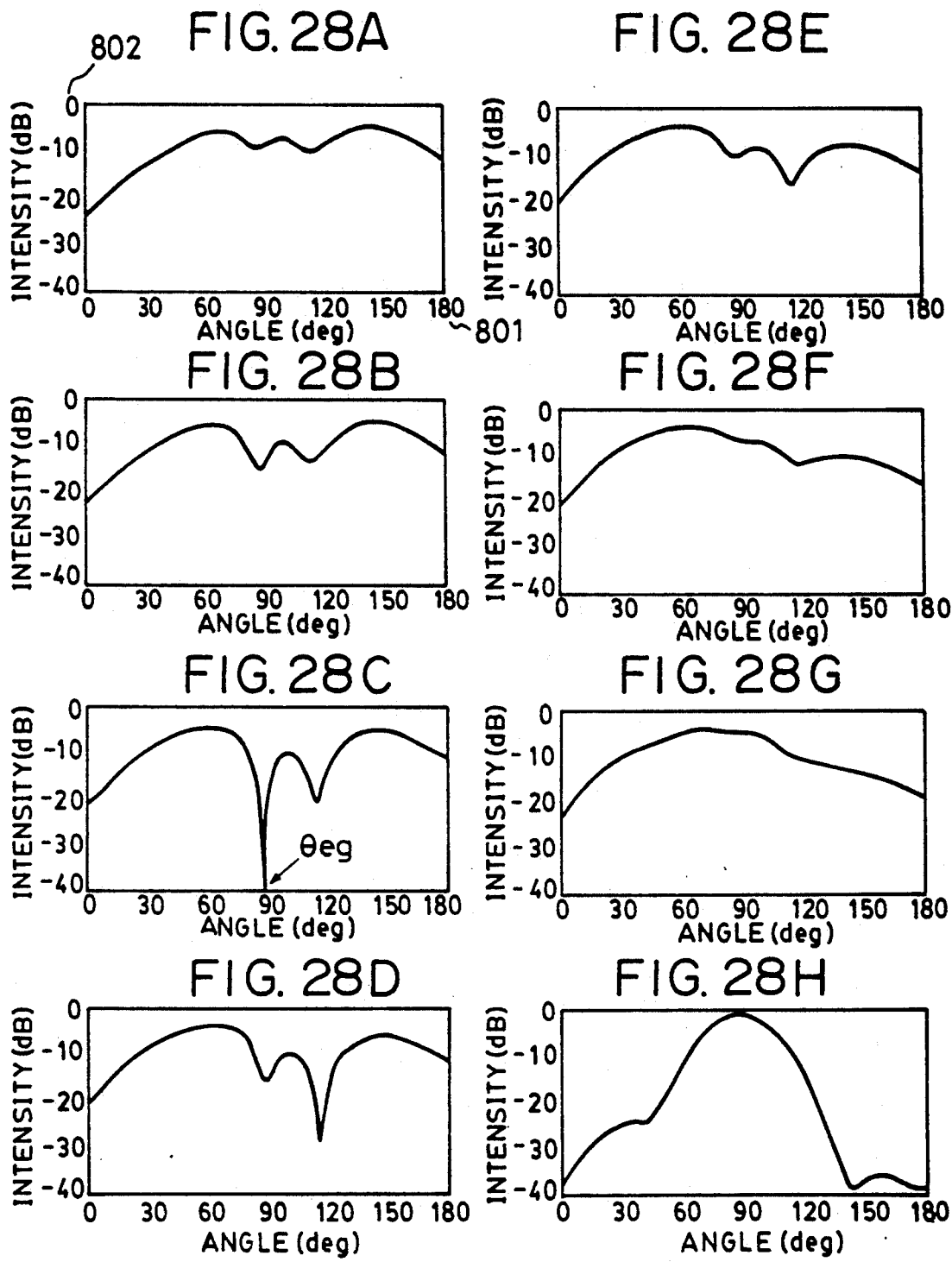
FIGS. 28A through 28H are diagrams illustrating scattering distribution characteristics when the edge to which the dust particle adheres is optically scanned.

FIG. 27 represents a model wherein a spherical dust particle adheres in the neighborhood of an edge (at a position separated from the edge of 0.3 $\mu$m). The edge is the same as that shown in FIG. 23, and the dust particle is the same as that shown in FIG. 25. The contact point between the spherical dust particle 901 and the boundary surface 22 of the object 2 is arranged to be the origin 704, and the y axis and the z axis are set as indicated by reference numerals 701 and 702, respectively.

The scattering distribution characteristics of the scattered light are measured in a far field region separated from the origin 704 by about 1,000 multiples of the wavelength of the light. As in the case of FIG. 23, a Gaussian beam having a wavelength of 0.6328 $\mu$m and a beam spot diameter of 1.0 $\mu$m is used as the projected focused light beam 35, and the position of the beam waist is arranged to be on the y axis. The edge in whose neighborhood the dust particle adheres is scanned with the above-described focused light beam by means of the scanning system in the y-axis direction. Scattering distribution characteristics measured when the optical axis of the focused light beam corresponds to positions "a", "b", "c", "d", "e", "f", "g" and "h" shown in FIG. 27 become as shown in FIGS. 28A, 28B, 28C, 28D, 28E, 28F, 28G and 28H.

FIGS. 28A through 28H show the scattering distribution characteristics for the edge in whose neighborhood the dust particle adheres. The following items hold from FIGS. 28A through 28H.

(6-1) While only one local minimum value is produced in the scattering distribution characteristics when an edge having a height of about 0.1 μm is optically scanned, two local minimum values are produced if a dust particle having a size of about 0.3 μm adheres in the neighborhood of the edge.

(6-2) The position $\theta eg$ of the local minimum value in general differs from the position $\theta e$ shown in FIGS. 24A through 24E, and the position $\theta g$ shown in FIGS. 26A through 26E.

Accordingly, by optically scanning a fine edge of an object, measuring scattering distribution characteristics of scattered light, and analyzing the number and the positions of the local minimum values in the scattering distribution characteristics, it is determined that:

(i) a foreign particle is present if two local minimum values are produced, and (ii) a foreign particle is present if the position of the local minimum value differs from the position $\theta e$. Thus, in the present embodiment, a foreign particle adhering to the object is detected.

For example, in detecting foreign particles adhering to a reticle or a mask on which circuit patterns are formed, the surface of the reticle or the mask is optically scanned with a focused light beam whose spot size is reduced to about 1.0 μm by an illuminating optical system, and the positions and the number of the local minimum values in the scattering distribution characteristics of the scattered light are measured by a signal processing system and a computer to determine whether a structure within a minute region illuminated by the focused light beam is an edge structure or a dust particle, whereby a foreign particle is detected.

In detecting foreign particles adhering to a reticle or a mask on which circuit patterns are formed, the circuit patterns are previously stored in a computer. When an object is optically scanned, the user knows which portion of the object is scanned by positioning processing or the like, and finds out a foreign particle by comparing the previously calculated positions and the number of the local minimum values in the scattering distribution characteristics of the scattered light with the actually measured positions and number of the local minimum values.

Although in the foregoing explanation, one-dimensional spatial distribution characteristics of light scattered by a predetermined cross section of the object 2 were utilized, it is also possible to three dimensionally detect dust particles adhering to the object 2 by detecting spatial distribution characteristics which three dimensionally expand.

Although in the above-described embodiments, the object 2 is optically scanned while moving the object 2, it is also possible to use an optical system which has a telecentric scanning system at the side of the object 2, and continuously deflect light by a scanner, such as a galvanomirror, a polygon mirror, a plane parallel plate or the like to scan the object 2 with a vertically incident light beam.

The following embodiment of the present invention is characterized in that light from a light source means is focused onto a minute region on an object as a spot light beam so as to inclusively illuminate a fine pattern line having a size smaller than the spot diameter of the focused light beam. After adjusting the optical axis of the focused light beam to the center of the pattern line, the spot size of the focused light beam is changed by a spot size changing unit, scattering distribution characteristics of light scattered by the structure of the fine pattern line are sequentially photoelectrically detected, and information regarding the fine structure included in the scattering distribution characteristics is extracted, whereby the width and the height of the pattern line are measured with a resolution exceeding the resolution of a conventional optical microscope. In extracting the information, evaluation is performed by analyzing how the positions and the number of the local minimum values in the scattering distribution characteristics detected by a detector change in accordance with changes in the spot size of the focused light beam.

A specific fine structure evaluation apparatus of the embodiment is characterized in that a light beam from a light source means is projected upon an object having a fine structure via an illuminating optical system including a spot size changing unit for changing the spot size of the illuminating light beam, scattering distribution characteristics of light scattered by the fine structure of the object are detected by a detection system, and scattering signals representing the positions, the number, changes, the intensities, and the like of the extreme values in the scattering distribution characteristics obtained by the detection system are processed by a signal processing system, whereby the fine structure is evaluated.

In particular, the apparatus of the present embodiment is characterized in that, for example, the fine structure comprises a fine pattern line, the position of the light beam incident on the fine pattern line is adjusted by a scanning system by utilizing signals obtained by the detection system, and the signal processing system evaluates information on the width and the height from a reference surface of the fine pattern line.

The following fine structure evaluation method of the present embodiment is characterized in that light beams having different spot sizes are sequentially projected onto an object having a fine structure from an illuminating optical system including a spot size changing unit for changing the spot size of the illuminating light beam, distribution characteristics of light scattered by the object are detected, and the fine structure is evaluated using at least one of the positions, the number, changes and the intensities of the extreme values in the distribution characteristics of the scattered light.

The following fine structure evaluation method of the present embodiment is characterized in that light beams having different spot sizes are sequentially projected onto an object having a fine structure from an illuminating optical system having a spot size changing unit for changing the spot size of the illuminating light beam, distribution characteristics of light scattered by the object are detected, and the fine structure is evaluated according to changes in at least one of the positions, the number, changes and the intensities of the extreme values in the distribution characteristics of the scattered light as a result of the scanning operation.

Figure 29:
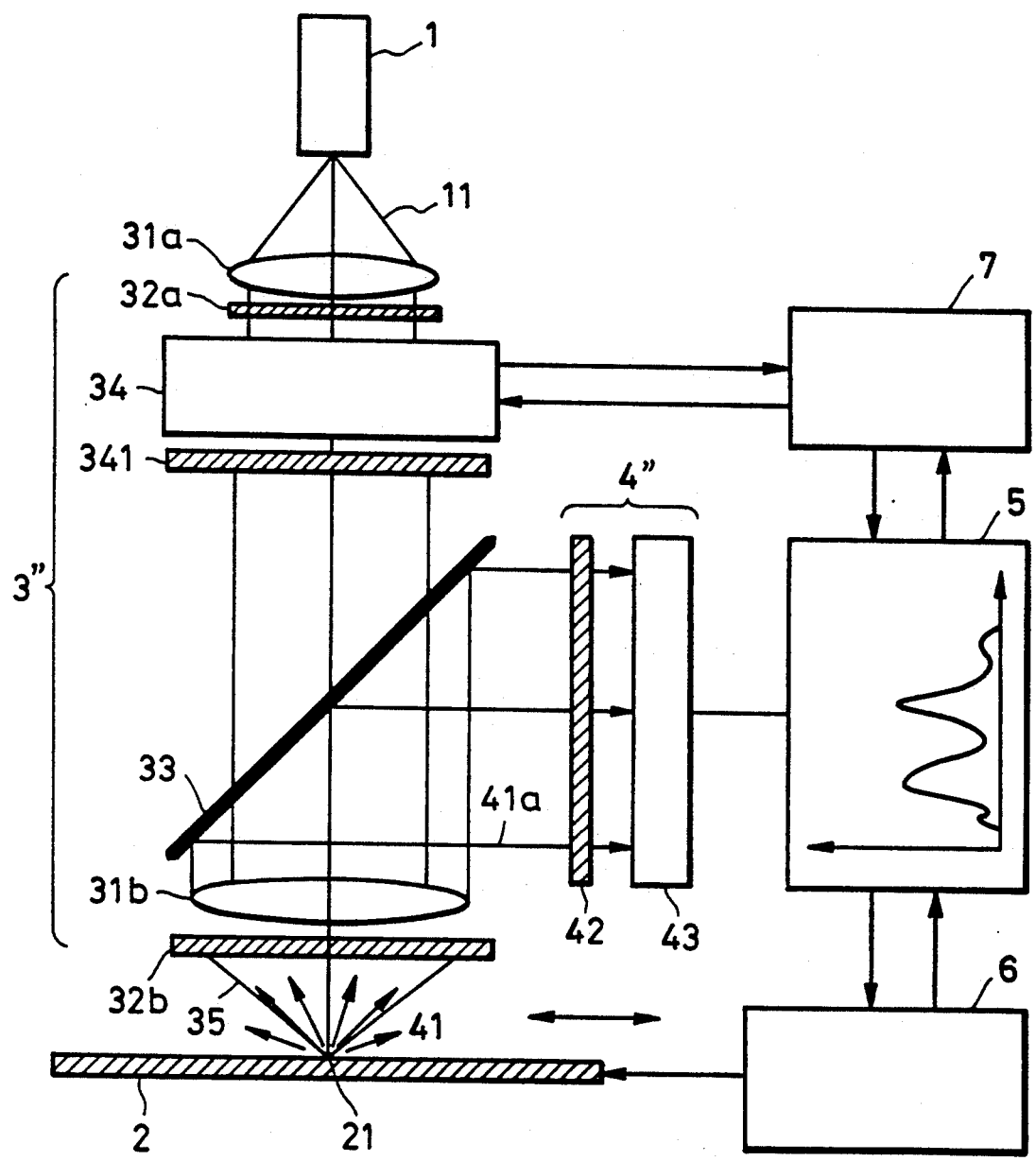
FIG. 29 is a schematic diagram of a principal part of a sixth embodiment of the present invention.

FIG. 29 is a schematic diagram of a principal part of a fine structure evaluation apparatus according to a sixth embodiment of the present invention.

In FIG. 29, there are shown a light source means 1, and an object 2 having a fine structure, such as a fine pattern line or the like. An illuminating optical system 3″ focuses light from the light source means 1 to provide a focused light beam 35 for illuminating a minute region 21 on the object 2. The illuminating optical system 3″ includes a lens system 31a, a filter system 32a, a spot size changing unit 34 for changing the spot size of the light beam illuminating the minute region 21 on the object 2, and a filter system 341 at the side of the light source means 1, and a lens system 31b and a filter system 32b at the side of the object 2, and a beam splitter 33 for introducing scattered light from the object 2 to a detection system 4" between the filter system 341 and the lens system 31b. The detection system 4" includes a filter system 42 for detecting scattering distribution characteristics of light 41 scattered by the fine structure of the object 2, and a photoelectric detector 43, such as a one-dimensional CCD, a two-dimensional CCD or the like. A signal processing system 5 analyzes the fine structure of the object 2 from signals representing the scattering distribution characteristics detected by the detection system 4". A scanning system 6 relatively scans the object 2 with the focused light beam 35, and makes the optical axis of the focused light beam 35 coincide with the center of the fine pattern line on the object 2. A computer 7 performs calculation processing of data processed by the signal processing system 5 to obtain information regarding the outer shape of the fine structure of the object 2, such as the width and the height of the pattern line.

Also in the present embodiment, for example, a semiconductor laser, a light source for emitting a coherent light beam, such as a He-Ne laser, an Ar laser or the like, a light source for emitting an incoherent light beam such as a light-emitting diode, a halogen lamp or the like may be used as the light source means 1. A light source which is suitable for a fine structure to be evaluated is selected on every occasion.

In the present embodiment, light 11 emitted from the light source means 1 is first focused onto the minute region 21 on the object 2 having the fine pattern-line structure by means of the illuminating optical system 3". Since the width of the pattern line to be measured has a size equal to or less than the spot size (equal to or less than the wavelength of the light) capable of being focused by a typical illuminating optical system, the focused light beam 35 is projected so as to include the pattern line within the spot of the focused light beam 35. The light beam 35 focused on the object 2 is scattered with scattering distribution characteristics which depend upon the structure of the pattern line in the minute region 21, and the position of the optical axis and the spot size of the focused light beam 35. The scattered light 41 is reflected by the beam splitter 33 after passing through the filter system 32b and the lens system 31b provided at the side of the object 2 to be separated as scattered light 41a, which is introduced into the detection system 4".

An ND filter for absorbing a constant ratio of light intensity, a polarizing filter, a low-pass filter or the like which is most suitable for measuring the scattering distribution characteristics is selected as the filter used in the illuminating optical system 3" or the detection system 4".

When the scattered light 41a is parallel light in the detection system 4", the minute region 21 and the detection surface of the detection system 4" are in the relationship of a Fourier transform. At that time, the detection system 4" measures the scattering distribution characteristics in a far-field region for the minute region 21 on the object 2. The scattering distribution characteristics of the scattered light 41a introduced in the detection system 4" are detected by the photoelectric detector 43 of the detection system 4" while being subjected to photoelectric conversion. The signals representing the detected scattering distribution characteristics are extracted by the signal processing system 5, where information on the positions and the number of the extreme values is analyzed by the computer 7. If asymmetry is present in the analyzed scattering distribution characteristics, the optical axis of the focused light beam 35 does not coincide with the center of the pattern line. In such a case, the position of the optical axis of the focused light beam 35 is adjusted to the center of the pattern line by performing a feedback operation so as to remove the asymmetry while relatively moving the optical axis of the focused light beam 35 and the position of the pattern line by means of the scanning system 6. When the optical axis of the focused light beam 35 illuminating the object 2 coincides with the center of the pattern line to be measured, the detected scattering distribution characteristics become symmetrical. The optical axis of the focused light beam 35 is fixed in this state, the scattering distribution characteristics are detected while suitably setting the spot size of the focused light beam 35 by the spot size changing unit 34 in accordance with a command from the computer 7, and the height of the pattern line is obtained by analyzing the result produced by the computer 7 according to a method to be described later. Subsequently, the spot size of the focused light beam 35 is changed by the spot size changing unit 34 (this operation will be hereinafter termed spot size scanning).

As the method of changing the spot size of the focused light beam 35 by the spot size changing unit 34, for example, a method in which a diaphragm is insertably provided and the apparent numerical aperture of the lens system 31b is changed by inserting the diaphragm in the light beam, or a method in which the size of the beam incident upon the lens system 31b is changed using a magnification-variable beam expander may be adopted. The scattering distribution characteristics are measured by the detection system 4" every time the spot size of the focused light beam 35 is changed, the signal processing system 5 extracts signals indicating how the positions and the number of the extreme values in the scattering distribution characteristics change in accordance with changes in the spot size with an excellent S/N ratio, and the computer 7 analyzes the result, whereby the width of the pattern line having a size equal to or less than the spot size is measured.

Figure 30:
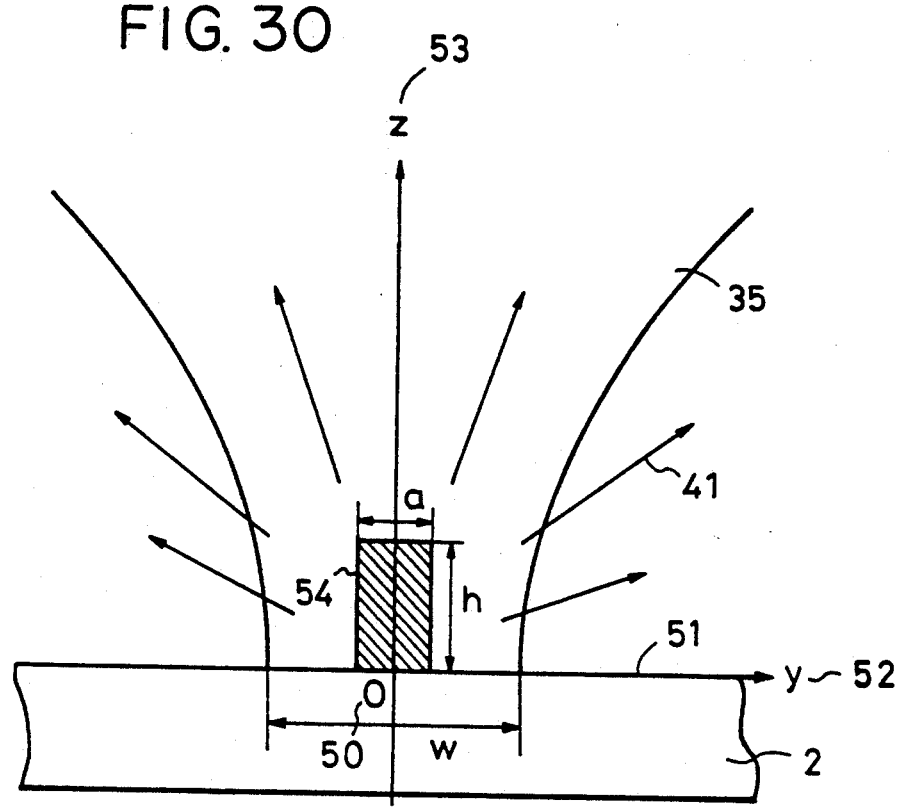
FIG. 30 is a diagram showing the coordinate system when a focused light beam is projected onto a pattern line.
Figure 31:
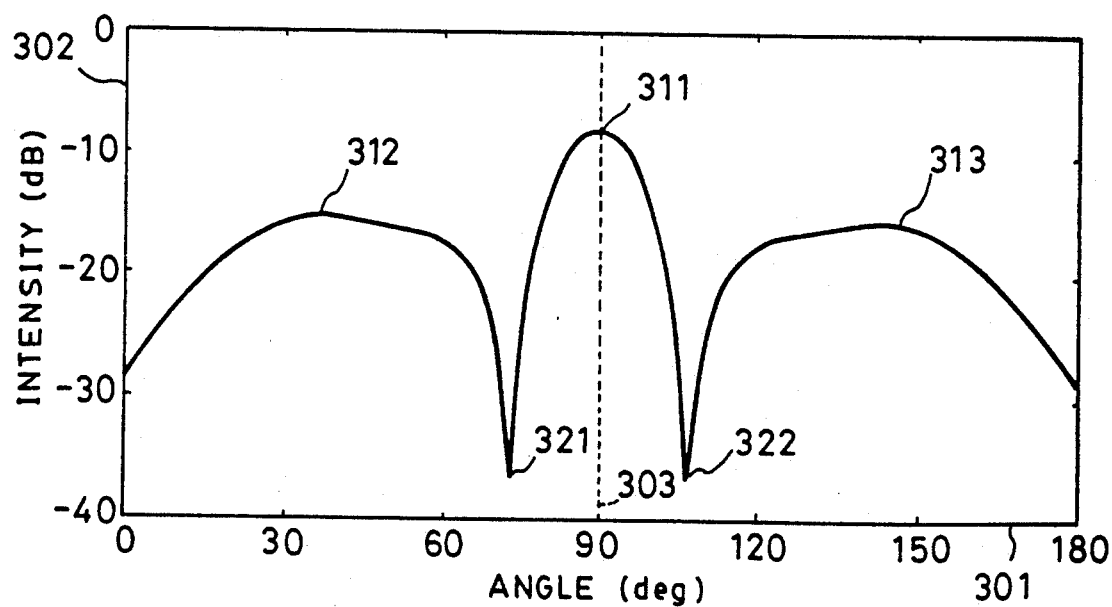
FIG. 31 is a diagram showing scattering distribution characteristics caused by the pattern line.

First, an explanation will be provided of a typical example of the present embodiment in which scattering distribution characteristics are detected by irradiating a focused light beam onto a pattern line. FIG. 30 shows the coordinate system when the focused light beam 35 is projected onto the object 2 having a pattern line having a size equal to or less than the spot size of the focused light beam 35. The boundary surface 51 of the object 2 is uniform in the direction perpendicular to the plane of FIG. 30 (the x direction), and comprises a perfect conductor. Reference numeral 54 represents the cross section of the pattern line provided on the object 2. The width of the pattern line is represented by "a" ($\mu$m), and the height of the pattern line is represented by h ($\mu$m). The spot size of the focused light beam 35 is represented by w ($\mu$m), as shown in FIG. 30. Accordingly, in the following description, the spot size indicates the diameter of the spot. In FIG. 30, the origin, the y axis and the z axis of the coordinate system of the pattern line are set as indicated by reference numerals 50, 52 and 53, respectively. When the focused light beam 35 is projected onto the pattern line 54 so that the optical axis of the focused light beam 35 coincides with the z axis 53, the light beam 35 is scattered as light 41 having certain scattering distribution characteristics. The scattering distribution characteristics are measured in a farfield region separated from the origin 50 by about 1,000 multiples of the wavelength of the light by the detection system 4". FIG. 31 shows an example of the scattering distribution characteristics detected in such a case.

The scattering distribution characteristics shown in FIG. 31 are obtained from the pattern line 54 having a width "a" of 0.2 μm and a height h of 0.3 μm when a Gaussian beam having a wavelength λ of 0.6328 μm and a diameter w of the beam spot of 1.6 μm with the focal plane arranged on the y axis 52 is used as the focused light beam.

Next, the coordinate system shown in FIG. 31 will be explained. The abscissa 301 represents the scattering direction of light scattered by the pattern line 54 on the object 2, in which the counterclockwise direction from the positive direction of the y axis 52 around the origin 50 is assumed to be the positive direction. The ordinate 302 represents the intensity of the measured scattered light 41. The unit of the intensity is a decibel, and 0 dB corresponds to the maximum value of the intensity of the scattered light when the focused light beam 35 is projected onto the boundary surface 51 of the object 2 which comprises a perfect conductor.

The following items hold from the scattering distribution characteristics shown in FIG. 31:

(i-1) The local maximum values 311, 312 and 313 are present.

(i-2) The local minimum values 321 and 322 are present.

(i-3) When the optical axis of the focused light beam 35 coincides with the center (the z axis) of the pattern line 54, the scattering distribution characteristics are symmetrical with respect to the scattering angle of 90 degrees.

If the position of the optical axis of the focused light beam 35 deviates from the center of the pattern line 54, asymmetry is produced in the detected scattering distribution characteristics. Next, an explanation will be provided of a method of making the optical axis of the focused light beam 35 coincide with the center of the pattern line 54 by utilizing the asymmetry.

Figure 32:
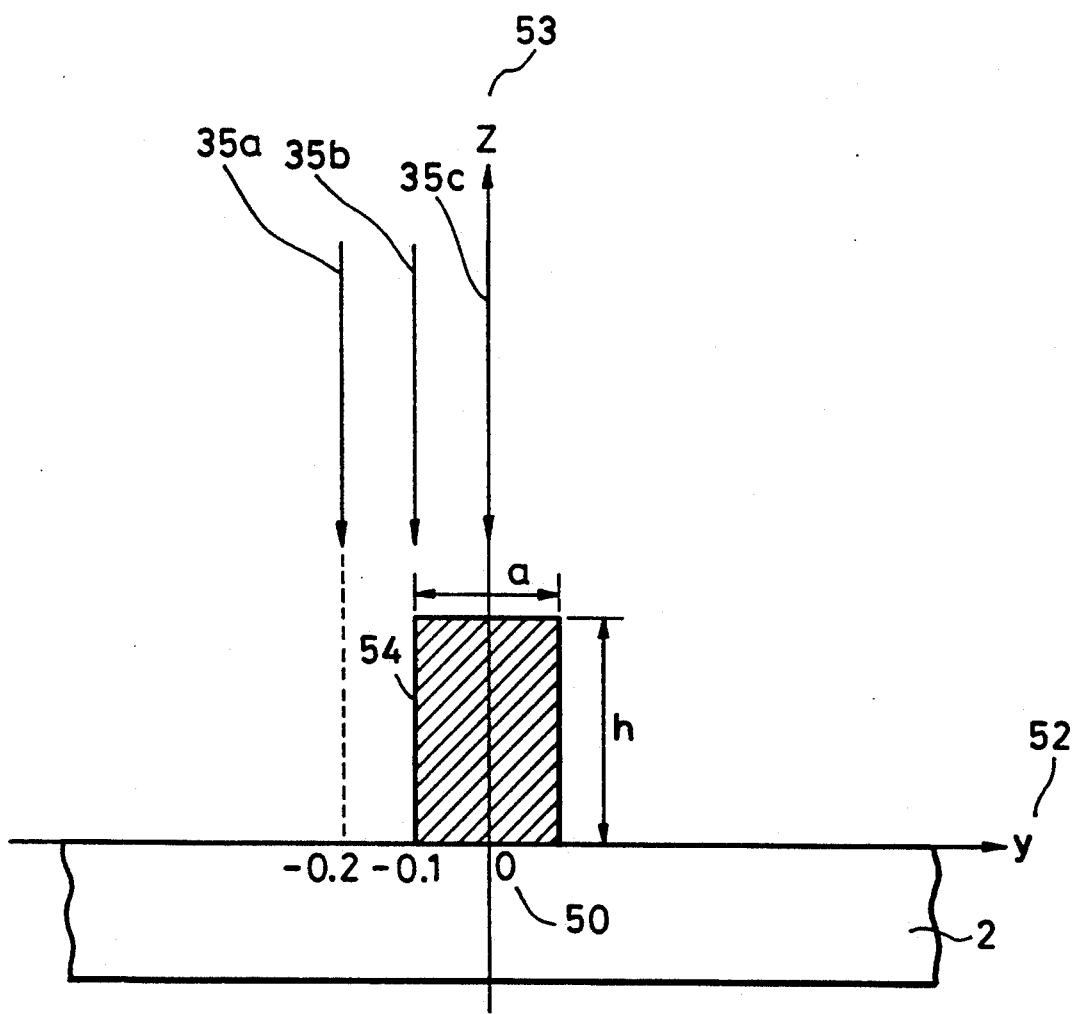
FIG. 32 is a diagram showing the positional relationship between the pattern line and the optical axis of the focused light beam.

FIG. 32 illustrates a model when the optical axis of the focused light beam 35 deviates from the center of the pattern line 54, which is the same line as that shown in FIG. 30. As in the case of FIG. 30, the pattern line 54 has a width "a" of 0.2 μm and a height h of 0.3 μm, and a Gaussian beam having a wavelength λ of 0.6328 μm and a diameter w of the beam spot of 1.6 μm with the focal plane arranged on the y axis 52 is used as the focused light beam. When the optical axis of the focused light beam 35 is at positions 35a, 35b and 35c, where the distance between the center of the pattern line 54 and the optical axis is 0.2 μm, 0.1 μm and 0 μm, respectively, the scattering distribution characteristics detected by the detection system 4 become as shown in FIGS. 33(A), 33(B) and 33(C), respectively.

Next, the coordinate system shown in FIGS. 33(A) through 33(C) will be explained. The abscissa 301 represents the scattering direction of light scattered by the pattern line 54 on the object 2, in which the counterclockwise direction from the positive direction of the y axis 52 around the origin 50 (shown in FIG. 32) is assumed to be the positive direction. The ordinate 302 represents the measured intensity of the scattered light. The unit of the intensity is a decibel, and 0 dB corresponds to the maximum value of the intensity of the scattered light measured when the focused light beam 35 is projected onto the boundary surface 51 of the object 2 which comprises a perfect conductor.

Figure 33A:
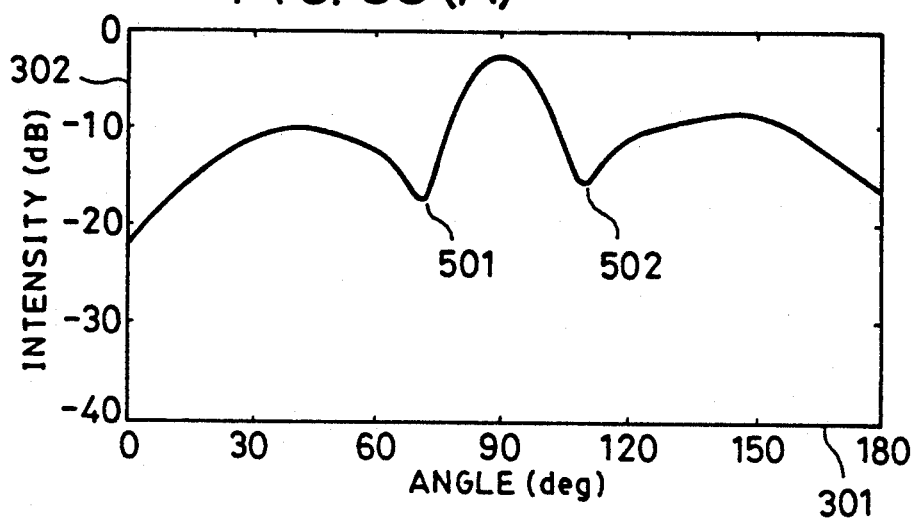
FIGS. 33(A) through 33(C) are diagrams showing scattering distribution characteristics when the optical axis of the focused light beam deviates from the center of the pattern line.
Figure 33B:
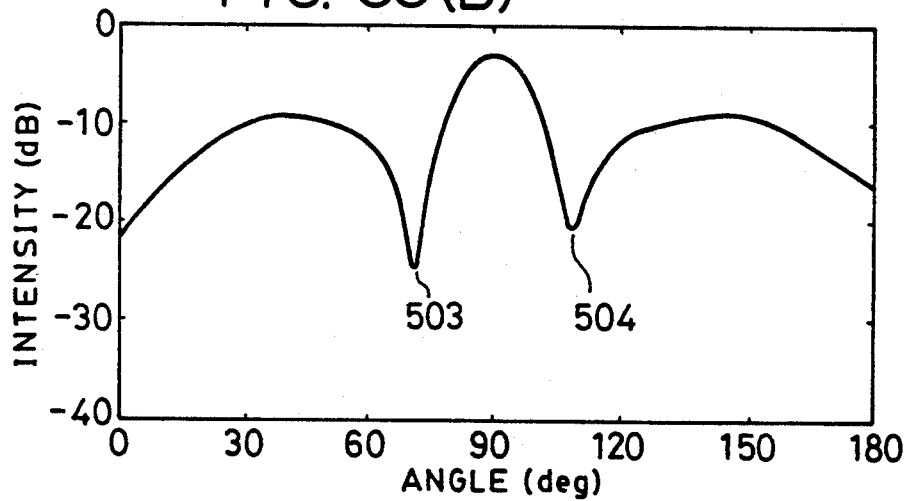
Figure 33C:
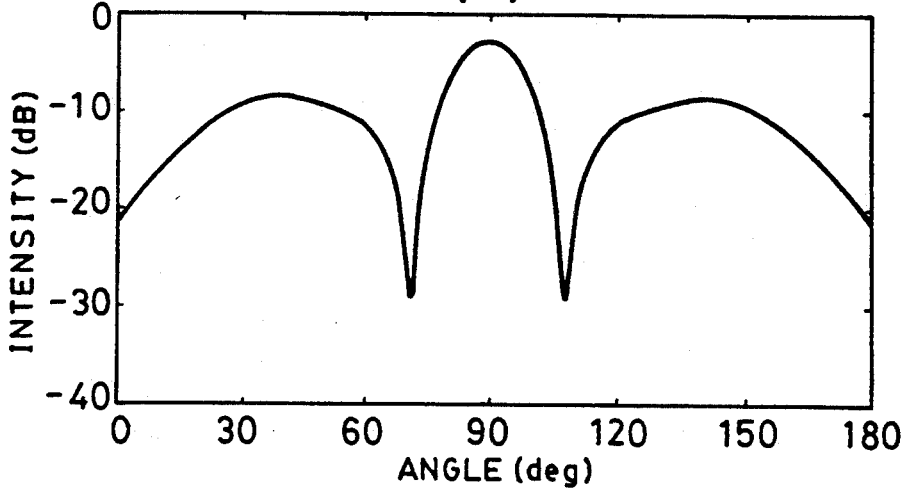

From FIGS. 33(A) and 33(B), it can be understood that when the optical axis of the focused light beam 35 is at a negative position of the y axis 52, the scattering distribution characteristics are asymmetrical with respect to the scattering angle of 90 degrees. From FIG. 33(C), it can be understood that when the optical axis of the focused light beam 35 coincides with the center of the pattern line 54, the scattering distribution characteristics are symmetrical with respect to the scattering angle of 90 degrees. Accordingly, if, for example, the intensity of the local minimum value present between the scattering angles of 0 degrees and 90 degrees is smaller, it is possible to make the optical axis of the focused light beam 35 coincide with the center of the pattern line 54 by moving the optical axis in the positive direction of the y axis 52. If the intensity of the local minimum value present between the scattering angles of 90 degrees and 180 degrees is smaller, the optical axis of the focused light beam 35 may be moved in the negative direction of the y axis 52 by the scanning system 6.

As described above, by extracting information on the local minimum values in the scattering distribution characteristics detected by the detection system 4 by the signal processing system 5, and analyzing the result produced by the computer 7, it is possible to move the optical axis of the focused light beam 35 to the center of the pattern line 54 by feeding back the information to the scanning system 6.

Figure 34:
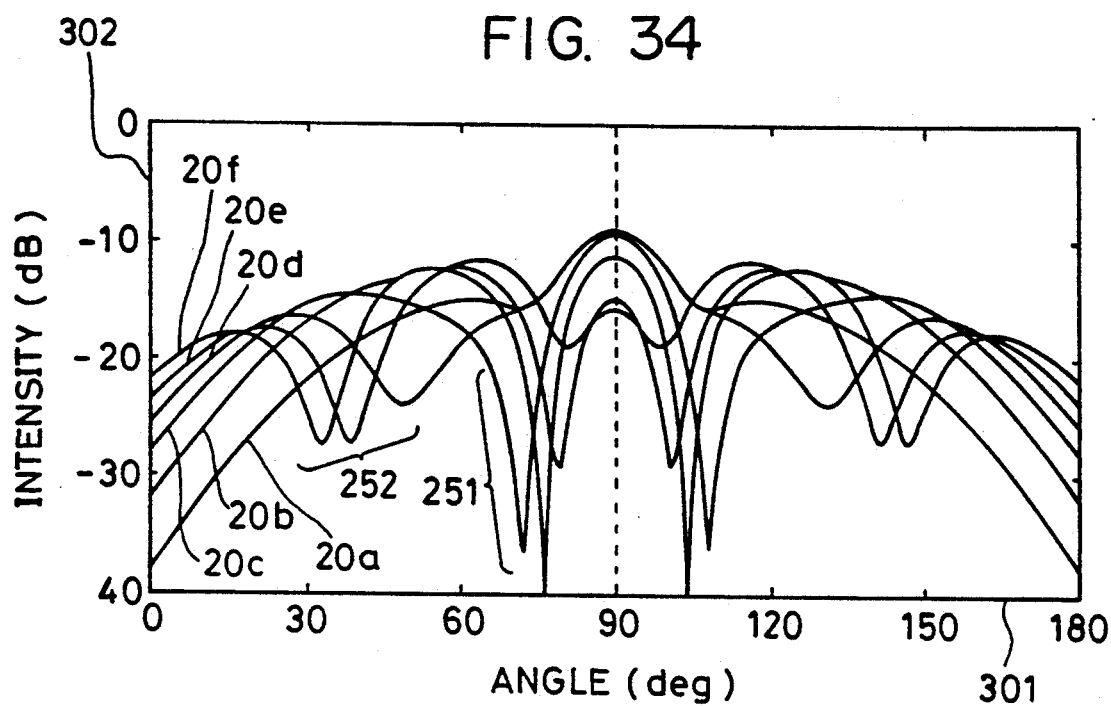
FIG. 34 is a diagram showing changes in the scattering distribution characteristics in accordance with changes in the height of the pattern line.

After positioning the optical axis of the focused light beam 35 with the center of the pattern line 54, the spot size w of the focused light beam 35 is set to an appropriately selected value by the spot size changing unit 34 while fixing the optical axis, and the scattering distribution characteristics from the pattern line 54 are detected. Subsequently, by analyzing the positions and the number of the local minimum values in the obtained scattering distribution characteristics, the height h of the pattern line 54 is obtained. FIG. 34 shows how the detected scattering distribution characteristics change in accordance with the height h of the pattern line 54. The width "a" of the pattern line 54 is set to 0.3 μm, and a Gaussian beam having a wavelength λ of 0.6328 μm and the diameter of the beam spot of 1.6 μm with the focal plane arranged on the y axis 52 is used as the focused light beam.

In FIG. 34, the abscissa 301 and the ordinate 302 are the same as those in FIG. 31. Curves 20a, 20b, . . . , 20f shown in FIG. 34 represent scattering distribution characteristics when the height h of the pattern line 54 changes by 0.1 μm from 0.1 μm to 0.6 μm. Since the characteristics in FIG. 34 are symmetrical with respect to the scattering angle of 90 degrees, an explanation will be provided for a range between 0 degree and 90 degrees. First, it can be understood that the scattering distribution characteristics greatly change in accordance with a minute change in the height h. It also can be understood that when the height h of the pattern line 54 exceeds λ/2 (~0.3 μm), local minimum values 252 are produced in addition to local minimum values 251, as represented by the curves 20d, 20e and 20f. The shape of such scattering distribution characteristics is substantially determined by the height h of the pattern line 54 if the wavelength λ and the spot size w of the focused light beam are determined, and does not so much depend upon the width "a" of the pattern line 54. Accordingly, it is possible to easily obtain the height h by, for example, providing a reference table within the computer 7 and comparing the table with the obtained scattering distribution characteristics.

Subsequently, the scattering distribution characteristics are measured while changing the spot size w of the focused light beam 35 by the spot size changing unit 34 (spot size scanning). The detected scattering distribution characteristics change in accordance with changes in the spot size. An explanation will now be provided of a method of obtaining the width "a" and the height h of the pattern line 54 from changes in the positions and the number of the extreme values in the scattering distribution characteristics.

Figure 35:
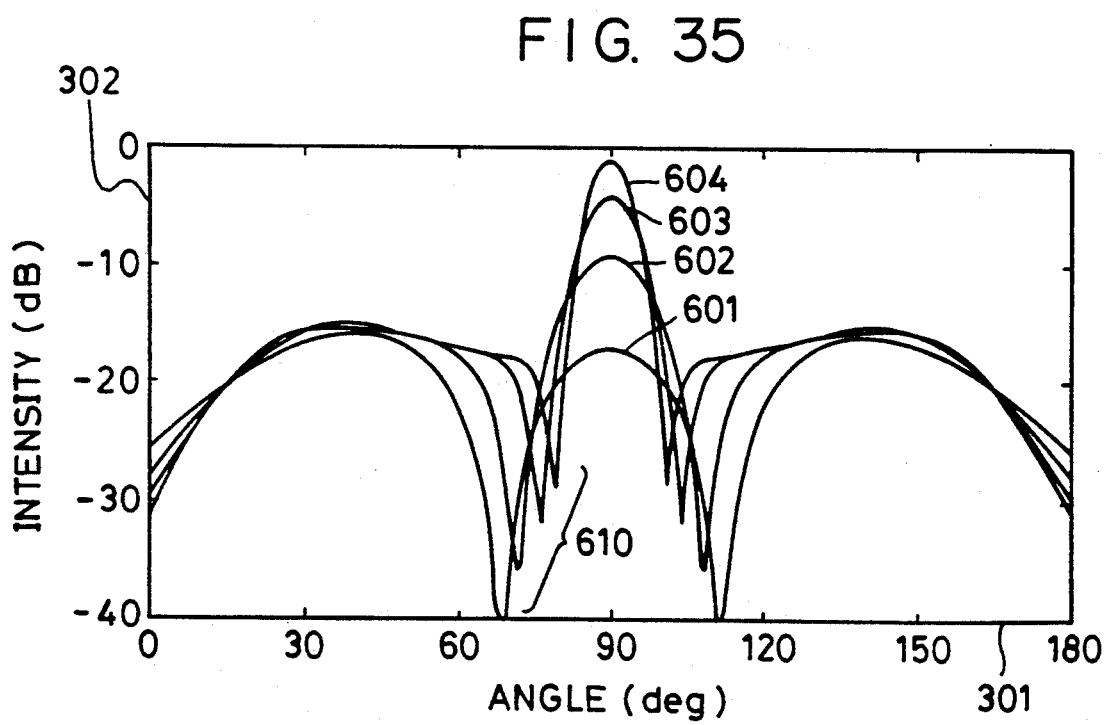
FIG. 35 is a diagram showing changes in the scattering distribution characteristics in accordance with changes in the spot size (a pattern width of 0.2 $\mu$m)

FIG. 35 shows how the scattering distribution characteristics change when the spot size w is changed as 0.8 µm, 1.4 µm, 2.2 µm and 3.0 µm for the pattern line 54 having a width "a" of 0.2 µm and a height h of 0.3 µm shown in FIG. 30. Scattering distribution characteristics 601, 602, 603 and 604 correspond to the spot sizes of 0.8 µm, 1.4 µm, 2.2 µm and 3.0 µm, respectively. From FIG. 35, it can be understood that the positions of the minimum values become closer to the scattering angle of 90 degrees, and the intensities of the local minimum values gradually increase as the spot size w increases.

Figure 36:
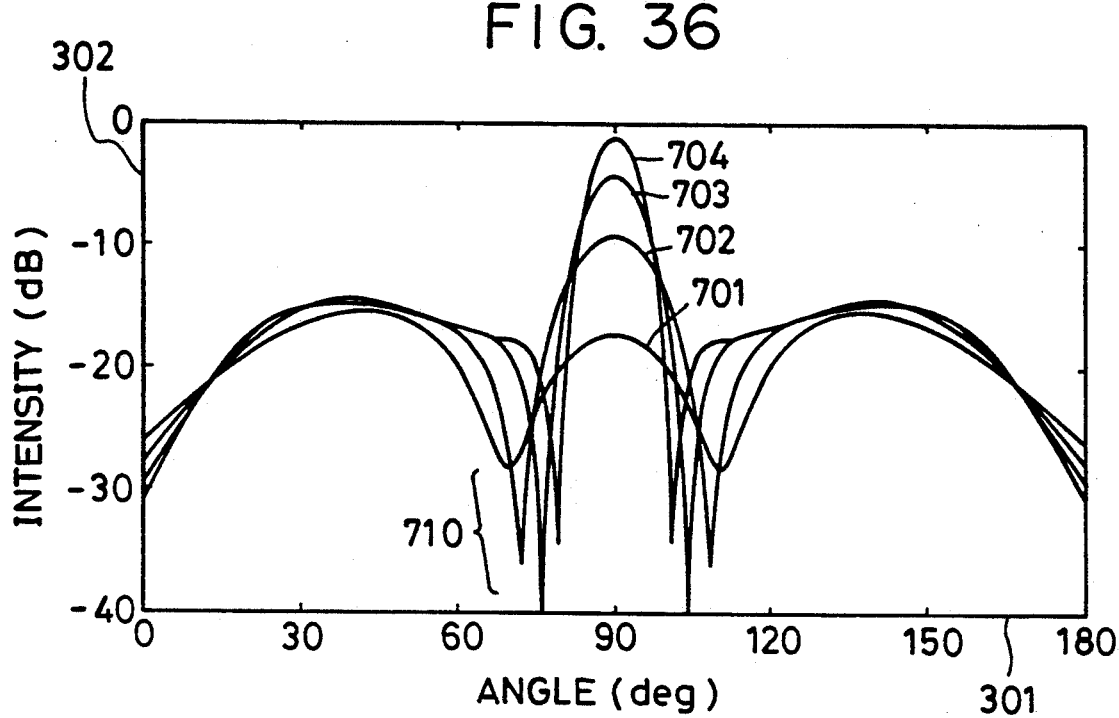
FIG. 36 is a diagram showing changes in the scattering distribution characteristics in accordance with changes in the spot size (a pattern width of 0.3 $\mu$m)
Figure 37:
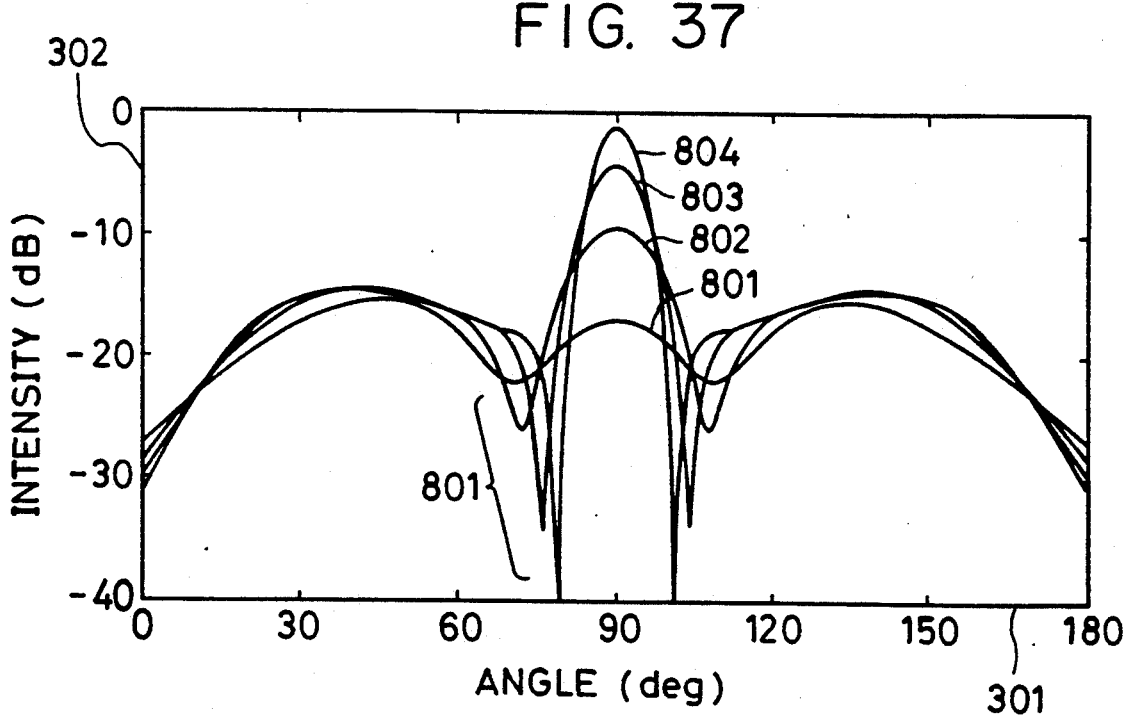
FIG. 37 is a diagram showing changes in the scattering distribution characteristics in accordance with changes in the spot size (a pattern width of 0.4 μm)

FIGS. 36 and 37 show how scattering distribution characteristics change when only the width "a" of the pattern line 54 is changed as 0.3 µm and 0.4 µm while leaving the height h of the pattern line 54 invariable.

Figure 38:
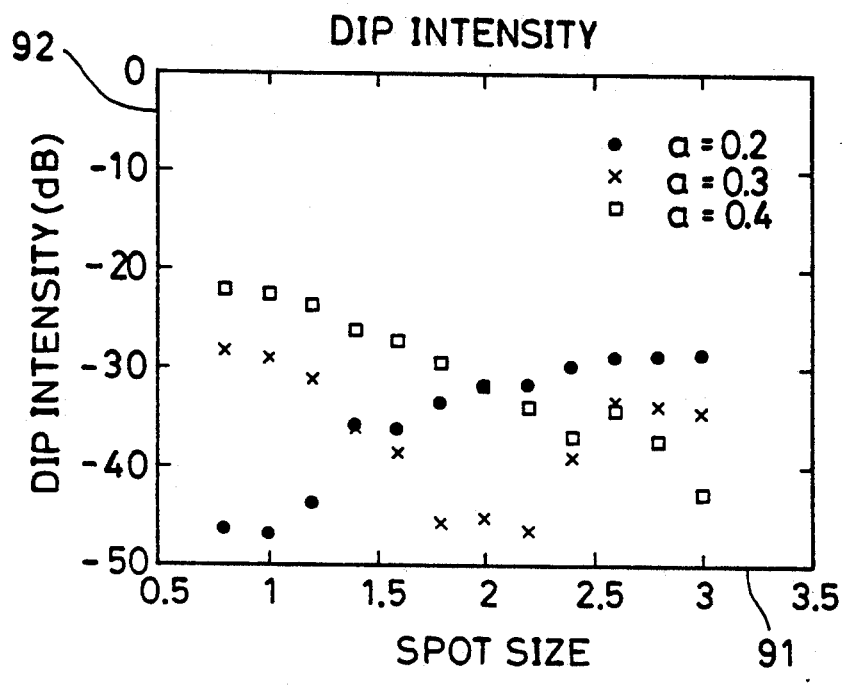
FIG. 38 is a graph showing the relationship between the spot size and the intensity of the local minimum value.
Figure 39:
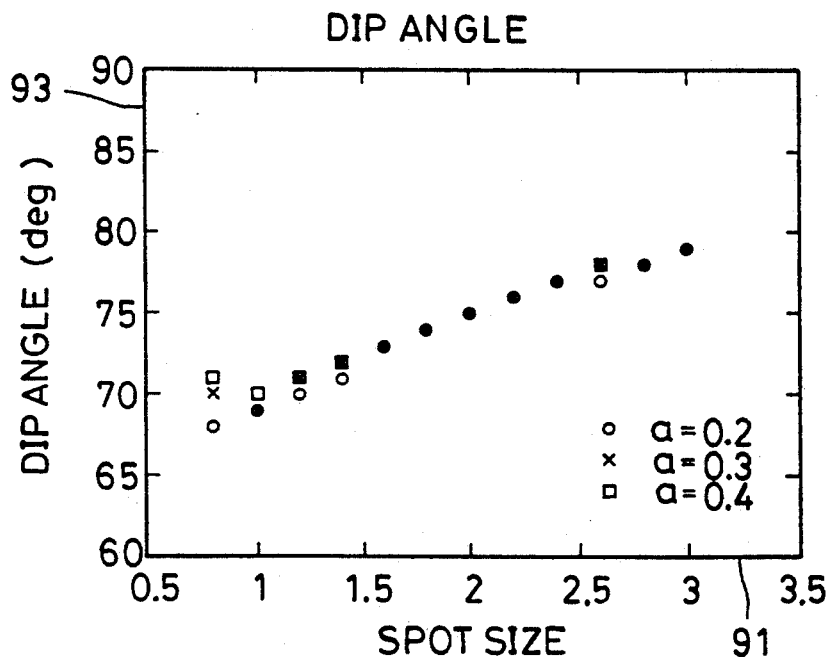
FIG. 39 is a graph showing the relationship between the spot size and the position of the local minimum value.

In comparing FIGS. 35, 36 and 37 with one another, it can be understood that while the shape of the scattering distribution characteristics do not change so much in accordance with changes in the spot size w, the intensities of the local minimum values change differently. FIGS. 38 and 39 show how the intensities of the local minimum values change.

FIG. 38 is a graph showing how the intensities of the local minimum values 610, 710 and 810 in the scattering distribution characteristics shown in FIGS. 35, 36 and 37, respectively, change in accordance with changes of the spot size w of the focused light beam illuminating the pattern line 54. In FIG. 38, the abscissa 91 represents the diameter of the spot of the focused light beam, and the ordinate 92 represents the intensities of the local minimum values in the detected scattering distribution characteristics. From FIG. 38, it can be understood that the intensities of the local minimum values change by changing the spot size w, and the manner of the change differs in accordance with the width "a" of the pattern line 54.

FIG. 39 is a graph showing how the scattering angles of the local minimum values 610, 710 and 810 in the scattering distribution characteristics shown in FIGS. 35, 36 and 37, respectively, change in accordance with changes in the spot size w of the focused light beam 35 illuminating the pattern line 54. In FIG. 39, the abscissa 91 represents the diameter of the spot of the focused light beam 35, and the ordinate 93 represents the scattering angles of the local minimum values in the detected scattering distribution characteristics. From FIG. 39, it can be understood that the scattering angles of the local minimum values change as the spot size w is changed, but the manner of the change is invariable even if the width "a" of the pattern line 54 changes. Since the changes in the scattering angles of the local minimum values depend upon the divergent angle $\theta = \lambda/\pi w_0$ of the incident Gaussian beam, information regarding the width "a" cannot be obtained from the manner of the changes.

From FIGS. 38 and 39, it can be said that differences due to differences in the width "a" of the pattern line 54 in accordance with changes in the spot size w of the focused light beam 35 appear in the intensities of the local minimum values in the scattering distribution characteristics, as shown in FIG. 38. Hence, the relationship between the spot size w and the intensity of the local minimum value is analyzed by the computer 7.

Figure 40:
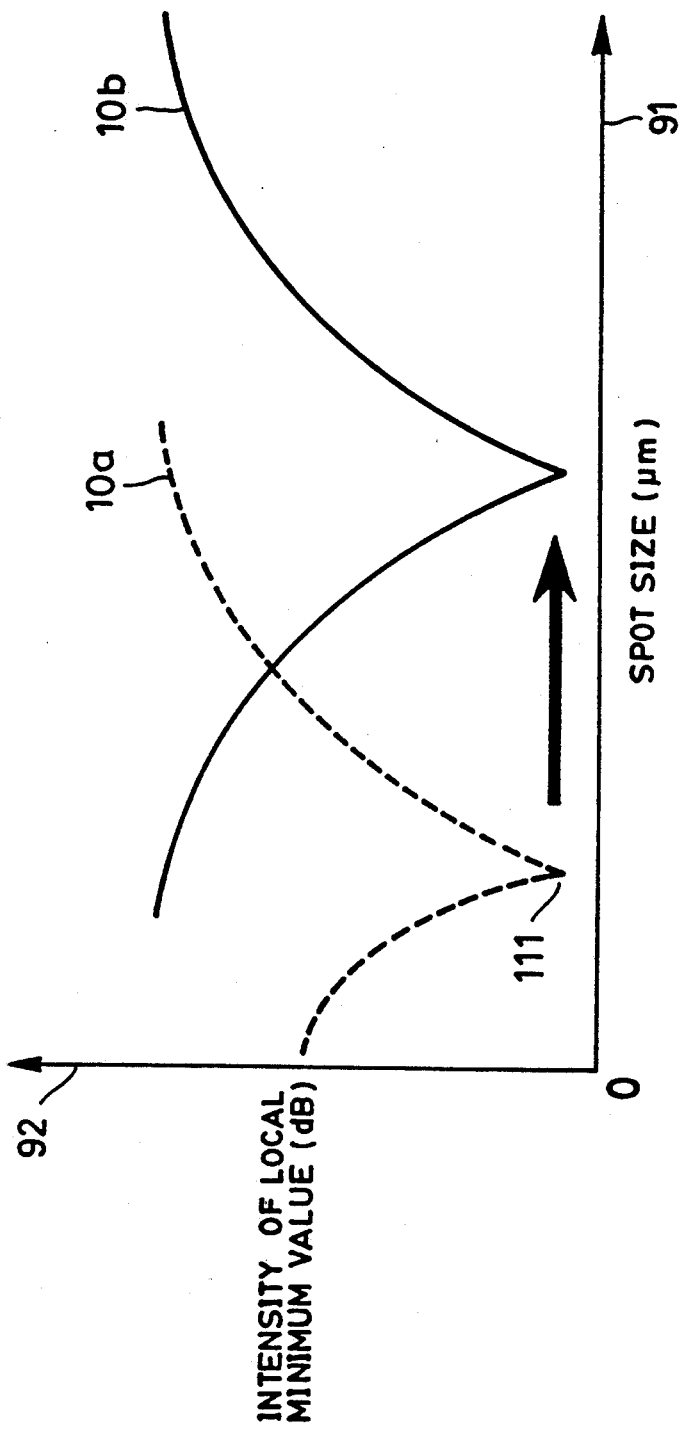
FIG. 40 is a diagram schematically showing the relationship between the spot size and the intensity of the local minimum value.

FIG. 40 is a diagram schematically illustrating the diagram shown in FIG. 38. In FIG. 40, the abscissa 91 and the ordinate 92 are the same as those shown in FIG. 38. When the focused light beam 35 is projected onto the center of the pattern line 54 while changing the spot size w, for example, a curve 10a is obtained when the width of the pattern line 54 is "a", and a curve 10b is obtained when the width of the pattern line 54 is "b". Accordingly, by detecting the scattering distribution characteristics and analyzing changes in the intensities of the local minimum values in the scattering distribution characteristics by the computer 7, it is possible to obtain the line width "a" of the pattern by, for example, finding out the position of the local minimum value 111 in the graph.

Figure 41:
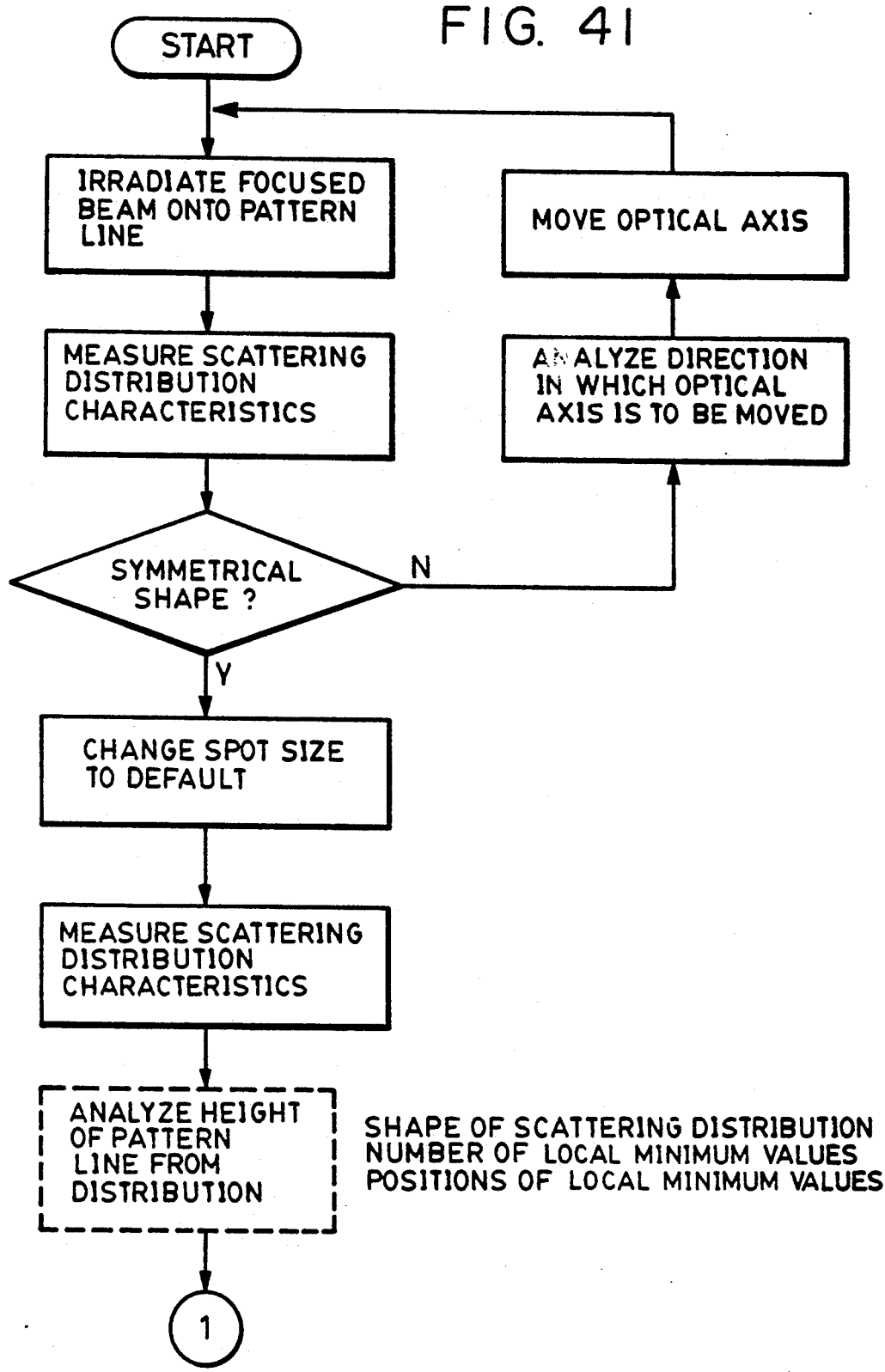
FIG. 41 is a flowchart for obtaining the height of a pattern line in the present invention.
Figure 42:
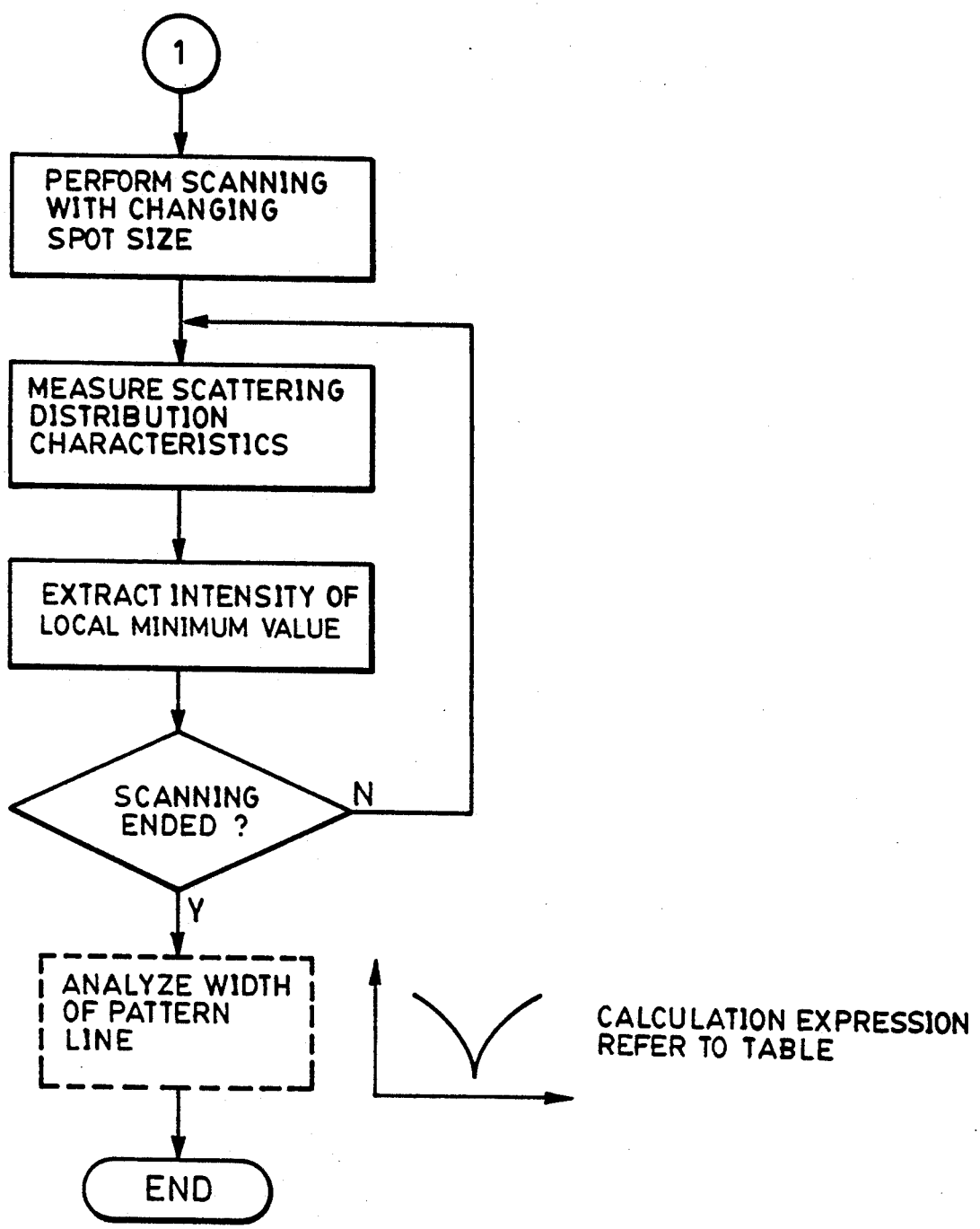
FIG. 42 is a flowchart for obtaining the width of a pattern line in the present invention.

FIG. 41 is a flowchart for obtaining the height h of the pattern line 54, and FIG. 42 is a flowchart for obtaining the width "a" of the pattern line 54.

Although in the present embodiment, the object 2 is optically scanned while moving the object 2, it is also possible to use an optical system which has a telecentric scanning system at the side of the object 2, and continuously deflecting light by a scanner, such as a galvanomirror, a polygon mirror, a plane parallel plate or the like, to scan the object 2 with a vertically incident light beam.

As described above, according to the present invention, it is possible to provide a fine structure evaluation apparatus and a fine structure evaluation method which can evaluate the outer shape, such as the height, the width or the like, of a fine structure, such as an edge or the like, on an object, or the presence of foreign particles on the object by detecting scattering distribution characteristics of light scattered by the fine structure or a foreign particle, and processing signals representing information on the scattered light in the scattering distribution characteristics.

Except as otherwise disclosed herein, the various components shown in outline or in block form in the Figures are individually well known and their internal construction and operation is not critical either to the making or using of this invention or to a description of the best mode of the invention.

While the present invention has been described with respect to what is at present considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded to the broadest interpretation so as to encompass all such modifications and equivalent structures and functions.

What is claimed is:

1. An apparatus for evaluating a fine structure of an object to be inspected, said apparatus comprising:

illumination means for irradiating the object with a light beam;

irradiating state changing means for changing an irradiating state of the light beam irradiating the object by said illumination means;

detection means for detecting those portions having extreme intensity values of light scattered by the illuminated object, and for producing a detection output; and calculation means for receiving the detection output from said detection means, and for evaluating the fine structure of the object according to changes in distribution characteristics of those portions having the extreme intensity values while changing the irradiating state of the light beam by said irradiating state changing means.

2. An apparatus according to claim 1, wherein said irradiating state changing means comprises means for scanning the object with the light beam from said illumination means to change the irradiating state of the light beam.

3. An apparatus according to claim 1, wherein said irradiating state changing means comprises means for changing the spot size of the light beam on the object to change the irradiating state of the light beam.

4. An apparatus according to claim 1, wherein said calculation means comprises means for evaluating the fine structure according to changes in at least one of the positions of the portions, the number of the portions and the intensity of scattered light at the portions having the extreme values.

5. An apparatus according to claim 1, wherein said calculation means comprises means for evaluating an outer shape of the fine structure of the object.

6. An apparatus according to claim 1, wherein said calculation means comprises means for detecting position information of the fine structure, and for producing a position signal, and wherein said apparatus further comprises positioning means for positioning the object according to the position signal produced by said calculation means.

7. An apparatus according to claim 1, wherein said calculation means comprises means for checking the presence of foreign particles on the object to evaluate the fine structure.

8. A method of evaluating a fine structure of an object to be inspected, said method comprising the steps of:
irradiating a light beam onto the object;
changing an irradiating state of the light beam;
detecting those portions of light scattered by the irradiated object having extreme intensity values; and
evaluating the fine structure of the object according to changes in distribution characteristics of those detected portions having the extreme values, while changing the irradiating state of the light beam.

9. A method according to claim 8, wherein said changing step comprises scanning the object with the light beam.

10. A method according to claim 8, wherein said changing step comprises changing the spot size of the light beam on the object.

11. A method according to claim 8, further comprising performing said evaluating step according to changes in at least one of the positions of the portions, the number of the portions and the intensity of scattered light at the portions having the extreme values.

12. A method according to claim 8, wherein an outer shape of the fine structure is evaluated as the evaluation of the fine structure.

13. A method according to claim 8, wherein said evaluating step comprises detecting position information of the fine structure on the object, and further comprising positioning the object according to the detection of the position information in said detecting step.

14. A method according to claim 8, wherein said evaluating step comprises checking for the presence of foreign particles on the object.

15. An apparatus for evaluating a fine structure of an object to be inspected, said apparatus comprising:
a light source for emitting a light beam;
an illuminating optical system for receiving the light beam emitted from said light source and for irradiating a light beam a predetermined position of the object, said illuminating optical system being capable of changing an irradiating state of the light beam onto the object;
a photoelectric transducer for detecting those portions of light scattered by the irradiated object having extreme intensity values; and
a signal processing system for evaluating the fine structure of the object according to changes in distribution characteristics of those detected portions having the extreme values, while changing the irradiating state of the light beam by said illuminating optical system.

16. An apparatus according to claim 15, wherein said illuminating optical system scans the object with the light beam to change the irradiating state of the light beam.

17. An apparatus according to claim 15, wherein said illuminating optical system changes the spot size of the light beam on the object to change the irradiating state of the light beam.

18. An apparatus according to claim 15, wherein said signal processing system evaluates the fine structure according to changes in at least one of the positions of the portions, the number of the portions and the intensity of scattered light at the portions having the extreme values.

19. An apparatus according to claim 15, wherein said signal processing system evaluates an outer shape of the fine structure.

20. An apparatus according to claim 15, wherein said signal processing system detects position information of the fine structure and produces a position signal, and wherein said apparatus further comprises a driving unit for positioning the object according to the position signal produced by said signal processing system.

21. An apparatus according to claim 15, wherein said signal processing system checks for the presence of foreign particles on the object to evaluate the fine structure.

* * * * *

UNITED STATES PATENT AND TRADEMARK OFFICE
CERTIFICATE OF CORRECTION

PATENT NO. : 5,270,794
DATED : December 14, 1993
INVENTOR(S) : TOSHIHIKO TSUJI, ET AL.

It is certified that error appears in the above-indentified patent and that said Letters Patent is hereby corrected as shown below:

ON THE COVER PAGE, item [30],

UNDER "FOREIGN APPLICATION PRIORITY DATA":

"May 15, 1992 [JP] Japan.....3-148569" should read
--May 15, 1992 [JP] Japan.....4-148569--.

COLUMN 10:

Line 39, "local" should read --the--; and
Line 40, "the" (first occurrence) should read --local--.

COLUMN 11:

Line 50, "spatical" should read --spatial--.

UNITED STATES PATENT AND TRADEMARK OFFICE
CERTIFICATE OF CORRECTION

PATENT NO. : 5,270,794
DATED : December 14, 1993
INVENTOR(S) : TOSHIHIKO TSUJI, ET AL.

It is certified that error appears in the above-indentified patent and that said Letters Patent is hereby corrected as shown below:

COLUMN 23:

Line 4, "farfield" should read --far-field--.

COLUMN 28:

Line 22, "beam a" should read --beam to a--.

Signed and Sealed this

Nineteenth Day of July, 1994

*Attest:*

BRUCE LEHMAN

*Attesting Officer*     *Commissioner of Patents and Trademarks*